US007906652B2

(12) United States Patent
Baker et al.

(10) Patent No.: US 7,906,652 B2
(45) Date of Patent: Mar. 15, 2011

(54) HETEROCYCLE-SUBSTITUTED 3-ALKYL AZETIDINE DERIVATIVES

(75) Inventors: Robert K. Baker, Cranford, NJ (US); Jeffrey J. Hale, Westfield, NJ (US); Shouwu Miao, Edison, NJ (US); Kathleen M. Rupprecht, Cranford, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 876 days.

(21) Appl. No.: 11/602,577

(22) Filed: Nov. 21, 2006

(65) Prior Publication Data

US 2007/0123505 A1 May 31, 2007

Related U.S. Application Data

(60) Provisional application No. 60/740,178, filed on Nov. 28, 2005.

(51) Int. Cl.
C07D 271/10 (2006.01)
C07D 205/04 (2006.01)

(52) U.S. Cl. .......................... 548/144; 548/950

(58) Field of Classification Search .................. 548/144, 548/950
See application file for complete search history.

(56) References Cited

U.S. PATENT DOCUMENTS

| | | | |
|---|---|---|---|
| 4,052,383 | A | 10/1977 | Gold et al. |
| 4,133,881 | A | 1/1979 | Cale et al. |
| 4,242,261 | A | 12/1980 | Cale |
| 6,355,631 | B1 | 3/2002 | Achard et al. |
| 6,479,479 | B2 | 11/2002 | Achard et al. |
| 6,518,264 | B2 | 2/2003 | Achard et al. |
| 6,858,603 | B2 | 2/2005 | Achard et al. |
| 6,872,717 | B2 | 3/2005 | Achard et al. |
| 7,132,414 | B2 | 11/2006 | Achard et al. |
| 2002/0016337 | A1 | 2/2002 | Cuny et al. |
| 2003/0055033 | A1 | 3/2003 | Achard et al. |
| 2006/0270650 | A1 | 11/2006 | MacNeil et al. |
| 2006/0293299 | A1 | 12/2006 | Baker et al. |
| 2007/0066587 | A1 | 3/2007 | Altisen et al. |

FOREIGN PATENT DOCUMENTS

| | | |
|---|---|---|
| EP | 1328269 | 5/2004 |
| WO | WO 97/46511 | 12/1997 |
| WO | WO 99/04794 | 2/1999 |
| WO | WO 00/15609 | 3/2000 |
| WO | WO 00/71518 | 11/2000 |
| WO | WO 01/64632 | 9/2001 |
| WO | WO 01/64633 | 9/2001 |
| WO | WO 01/64634 | 9/2001 |
| WO | WO 01/64676 | 9/2001 |
| WO | WO 02/12187 | 2/2002 |
| WO | WO 03/007939 | 1/2003 |
| WO | WO 03/018060 | 3/2003 |
| WO | WO 03/020314 | 3/2003 |
| WO | WO 2004/056800 | 7/2004 |
| WO | WO 2004/096763 | 11/2004 |
| WO | WO 2004/096794 | 11/2004 |
| WO | WO 2005/000809 | 1/2005 |
| WO | WO 2005/077897 | 8/2005 |
| WO | WO 2006/119260 | 11/2006 |
| WO | WO 2007/062193 | 5/2007 |
| WO | 2007067617 | 6/2007 |
| WO | 2007142217 | 12/2007 |

OTHER PUBLICATIONS

Kubinyi (3D QSAR in Drug Design: Ligand-Protein Interactions and Molecular Similarity, vol. 2-3, Springer, 1998, 800 pages). TOC and pp. 243-244 provided.*
Byrn et al., Pharm. Res., v. 12, n. 7, p. 945-54, 1995.*
Land and Kruse (Drug Discovery Today, (2005), v. 10, n. 10, p. 693-702).*
Wiley et al. (J. Pharmacology and Exper. Therap., (2001), v. 296, n. 3, p. 1013-1022).*
Adam et al., Exp. Opin. Ther. Patents, vol. 12 (2002), pp. 1475-1489, "Recent advances in the cannabinoids".
Lange et al., Drug Discovery Today, vol. 10 (2005), p. 693-702, "Medicinal chemistry strategies to CB1 cannabinoid receptor antagonists".
Hillier, "A one-pot preparation of 1,3-disubstituted azetidines", J. Org. Chem. (2006), 7885-7887, vol. 71.

* cited by examiner

*Primary Examiner* — Robert Havlin
(74) *Attorney, Agent, or Firm* — Baerbel R. Brown; John C. Todaro

(57) ABSTRACT

Novel compounds of the structural formula (I) are antagonists and/or inverse agonists of the Cannabinoid-1 (CB1) receptor and are useful in the treatment, prevention and suppression of diseases mediated by the CB1 receptor. The compounds of the present invention are useful as centrally acting drugs in the treatment of psychosis, memory deficits, cognitive disorders, Alzheimer's disease, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, the treatment of obesity or eating disorders, as well as the treatment of asthma, constipation, chronic intestinal pseudo-obstruction, cirrhosis of the liver, non-alcoholic fatty liver disease (NAFLD), and non-alcoholic steatohepatitis (NASH).

9 Claims, No Drawings

HETEROCYCLE-SUBSTITUTED 3-ALKYL AZETIDINE DERIVATIVES

CROSS-REFERENCE TO RELATED APPLICATIONS

This is a non-provisional application, which claims priority under 35 U.S.C. §119 from U.S. provisional application No. 60/740,178, filed Nov. 28, 2005.

BACKGROUND OF THE INVENTION

Marijuana (*Cannabis sativa* L.) and its derivatives have been used for centuries for medicinal and recreational purposes. A major active ingredient in marijuana and hashish has been determined to be $\Delta^9$-tetrahydrocannabinol ($\Delta^9$-THC). Detailed research has revealed that the biological action of $\Delta^9$-THC and other members of the cannabinoid family occurs through two G-protein coupled receptors termed CB1 and CB2. The CB1 receptor is primarily found in the central and peripheral nervous systems and to a lesser extent in several peripheral organs. The CB2 receptor is found primarily in lymphoid tissues and cells. Three endogenous ligands for the cannabinoid receptors derived from arachidonic acid have been identified (anandamide, 2-arachidonoyl glycerol, and 2-arachidonyl glycerol ether). Each is an agonist with activities similar to $\Delta^9$-THC, including sedation, hypothermia, intestinal immobility, antinociception, analgesia, catalepsy, anti-emesis, and appetite stimulation.

There are at least two CB1 modulators characterized as an inverse agonista or an antagonists, N-(1-piperidinyl)-5-(4-chlorophenyl)-1-(2,4-dichlorophenyl)-4-methylpyrazole-3-caboxamide (SR141716A), and 3-(4-chlorophenyl-N'-4-chlorophenyl)sulfonyl-N-methyl-4-phenyl-4,5-dihydro-1H-pyrazole-1-carboxarmide (SLV-319), in clinical trials for treatment of eating disorders and/or smoking cessation at this time. There still remains a need for potent low molecular weight CB1 modulators that have pharmacokinetic and pharmacodynamic properties suitable for use as human pharmaceuticals.

U.S. Pat. Nos. 6,355,631, 6,479,479 and PCT publications WO 01/64632, 01/64633, 01/64634, and 05/000809 are directed to azetidine derivatives as cannabinoid antagonists.

SUMMARY OF THE INVENTION

The present invention is concerned with heterocycle-substituted azetidine derivatives of general formula I:

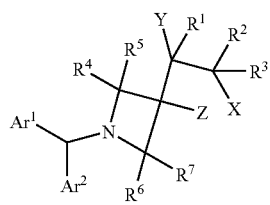

(I)

and pharmaceutically acceptable salts thereof which are modulators of and, in particular, antagonists and/or inverse agonists of the Cannabinoid-1 (CB1) receptor and are useful in the treatment, prevention or suppression of diseases mediated by the Cannabinoid-1 (CB1) receptor. In one aspect, the invention is concerned with the use of these novel compounds to selectively antagonize the Cannabinoid-1 (CB1) receptor. As such, compounds of the present invention are useful as centrally acting drugs in the treatment of psychosis, memory deficits, cognitive disorders, Alzheimer's disease, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, particularly abuse and/or addiction to opiates, alcohol, marijuana, and nicotine, including smoking cessation. The compounds are also useful for the treatment of obesity or eating disorders associated with excessive food intake and complications associated therewith, including left ventricular hypertrophy. The compounds are also useful for the treatment of constipation and chronic intestinal pseudo-obstruction. The compounds are also useful for the treatment of cirrhosis of the liver, non-alcoholic fatty liver disease (NAFLD) and non-alcoholic steatohepatitis (NASH). The compounds are also useful for the treatment of asthma.

The present invention is also concerned with treatment of these conditions, and the use of compounds of the present invention for manufacture of a medicament useful in treating these conditions. The present invention is also concerned with treatment of these conditions through a combination of compounds of formula I and other currently available pharmaceuticals.

The invention is also concerned with pharmaceutical formulations comprising one of the compounds as an active ingredient.

The invention is further concerned with processes for preparing the compounds of this invention.

DETAILED DESCRIPTION OF THE INVENTION

The compounds of the present invention are represented by structural formula I:

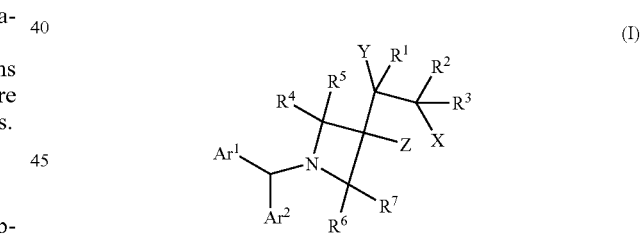

(I)

wherein:
$Ar^1$ is selected from:

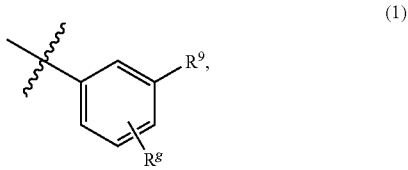

(1)

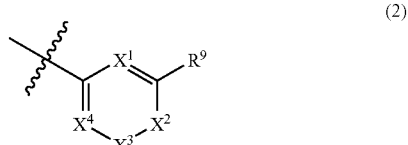

(2)

wherein one of $X^1$, $X^2$, $X^3$, and $X^4$ is —N—, and the others are each selected from —CH—, and —C($R^c$)—, provided that only one of $X^1$, $X^2$, $X^3$ and $X^4$ is —C($R^c$)—,

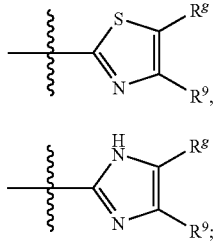  (3)

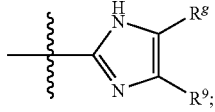  (4)

$Ar^2$ is selected from:

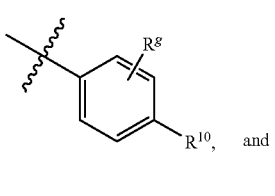  (1)

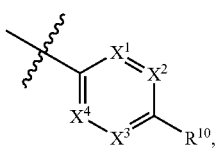  (2)

wherein one of $X^1$, $X^2$, $X^3$, and $X^4$ is —N—, and the others are each selected from —CH—, and —C($R^c$)—, provided that only one of $X^1$, $X^2$, $X^3$ and $X^4$ is —C($R^c$)—, X is selected from:
(1) hydroxy,
(2) $C_{1-6}$alkyl, straight chain or branched, unsubstituted or substituted with one to two $R^b$ substituents,
(3) perfluoro $C_{1-6}$alkyl,
(4) $C_{2-6}$alkenyl, straight chain or branched, unsubstituted or substituted with one to two $R^b$ substituents,
(5) $C_{2-6}$alkynyl, straight chain or branched, unsubstituted or substituted with one to two $R^b$ substituents,
(6) cyano,
(7) —C(O)$R^{11}$,
(8) —C(O)O$R^{12}$,
(9) —C(O)N($R^{12}$)($R^{13}$),
(10) —N($R^{14}$)S(O)$_n R^{11}$,
(11) —N$R^{14}$C(O)$R^{11}$,
(12) —N$R^{14}$C(O)O$R^{11}$,
(13) —N($R^{12}$)($R^{13}$),
(14) —S(O)$_n R^{11}$,
(15) —O$R^{11}$,
(16) —OC(O)$R^{11}$, and
(17) —OC(O)N($R^{12}$)($R^{13}$);

Y is selected from:
(1) hydrogen,
(2) hydroxy,
(3) $C_{1-3}$ alkyloxy,
(4) fluoro,
(5) $C_{1-3}$ alkyl,
(6) trifluoromethyl, and
(7) —N($R^{12}$)($R^{13}$);

Z is selected from hydrogen, hydroxy, methoxy, fluoro, methyl and —N($R^{12}$)($R^{13}$);

$R^1$ is selected from:

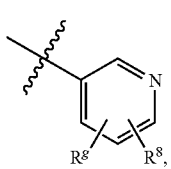  (1)

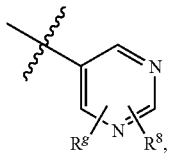  (2)

wherein $R^8$ and $R^g$ are bonded to a carbon atom of the ring,

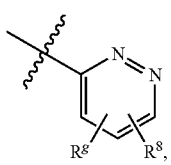  (3)

wherein $R^8$ and $R^g$ are bonded to a carbon atom of the ring,

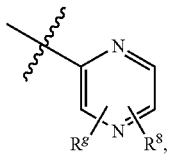  (4)

wherein $R^8$ and $R^g$ are bonded to a carbon atom of the ring, (5)

wherein R⁸ and R⁸ are bonded to a carbon atom of the ring,

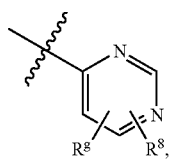
(6)

wherein R⁸ and R⁸ are bonded to a carbon atom of the ring,

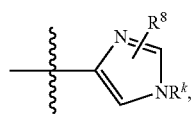
(7)

wherein R⁸ is bonded to a carbon atom of the ring,

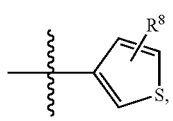
(8)

wherein R⁸ is bonded to a carbon atom of the ring, and

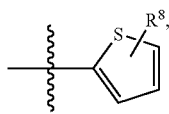
(9)

wherein R⁸ is bonded to a carbon atom of the ring;

$R^2$ is selected from:
(1) hydrogen,
(2) $C_{1-6}$alkyl, straight chain or branched, unsubstituted or substituted with one or two $R^b$ substituents,
(3) fluoro,
(4) hydroxyl,
(5) perfluoro $C_{1-6}$alkyl, straight chain or branched; and $R^3$ is selected from:
(1) hydrogen,
(2) $C_{1-6}$alkyl, straight chain or branched, unsubstituted or substituted with one or two $R^b$ substituents,
(3) fluoro,
(4) hydroxy,
(5) perfluoro $C_{1-6}$alkyl, straight chain or branched;
or $R^2$ and $R^3$, together with the carbon atom to which they are attached, form a carbonyl group, or a 3 to 7 membered carbocyclic ring;
provided that when X is hydroxy, $-NR^{14}C(O)R^{11}$, $-NR^{14}C(O)OR^{11}$, $-N(R^{12})(R^{13})$, or $-OR^{11}$, then:
(1) $R^2$ and $R^3$ are not both hydrogen, and
(2) $R^2$ and $R^3$ do not form a carbonyl group together with the carbon to which they are attached;

$R^4$, $R^5$, $R^6$, and $R^7$ are each independently selected from: hydrogen, $C_{1-6}$ alkyl, unsubstituted or substituted with $R^b$, and $C_{2-6}$ alkenyl, unsubstituted or substituted with $R^b$;

$R^8$ is selected from:
(1) $R^{15}$,
(2) hydrogen,
(3) halogen,
(4) $-OR^{11}$,
(5) $-CF_3$,
(6) aryl,
(7) heteroaryl,
(8) cyano,
(9) $-C(O)R^{11}$,
(10) $-C(O)OR^{11}$,
(11) $-C(O)N(R^{12})(R^{13})$,
(12) $-N(R^{14})S(O)nR^{11}$,
(13) $-NR^{14}C(O)R^{11}$,
(14) $-NR^{14}C(O)OR^{11}$,
(15) $-N(R^{12})(R^{13})$,
(16) $-S(O)nR^{11}$,
(17) $-S(O)_2OR^{11}$,
(18) $-OC(O)R^{11}$,
(19) $-OC(O)N(R^{12})(R^{13})$,
(20) $-NO_2$,
(21) $C_{3-7}$ cycloalkyl,
(22) cycloheteroalkyl,
(23) $C_{1-6}$ alkyl,
(24) $C_{2-6}$ alkenyl,
(25) $C_{2-6}$ alkynyl, and
(26) aryl-$C_{1-6}$ alkyl;
wherein alkyl, alkenyl, alkynyl are straight chain or branched; alkyl, alkenyl, alkynyl, cycloalkyl, cycloheteroalkyl and aryl are optionally substituted with one to four substituents selected from a group independently selected from $R^d$;

$R^9$ is selected from:
(1) $R^{15}$,
(2) hydrogen,
(3) halogen,
(4) $-OR^{11}$,
(5) $-CF_3$,
(6) aryl,
(7) heteroaryl,
(8) cyano,
(9) $-C(O)R^{11}$,
(10) $-C(O)OR^{11}$,
(11) $-C(O)N(R^{12})(R^{13})$,
(12) $-N(R^{14})S(O)nR^{11}$,
(13) $-NR^{14}C(O)R^{11}$,
(14) $-NR^{14}C(O)OR^{11}$,
(15) $-N(R^{12})(R^{13})$,
(16) $-S(O)nR^{11}$,
(17) $-S(O)_2OR^{11}$,
(18) $-OC(O)R^{11}$,
(19) $-OC(O)N(R^{12})(R^{13})$,
(20) $-NO_2$,
(21) $C_{3-7}$ cycloalkyl,
(22) cycloheteroalkyl,
(23) $C_{1-6}$ alkyl,
(24) $C_{2-6}$ alkenyl,
(25) $C_{2-6}$ alkynyl, and
(26) aryl-$C_{1-6}$ alkyl;
wherein alkyl, alkenyl, alkynyl are straight chain or branched; alkyl, alkenyl, alkynyl, cycloalkyl, cycloheteroalkyl and aryl are optionally substituted with one to four substituents selected from a group independently selected from $R^d$;

$R^{10}$ is selected from:
(1) $R^{15}$,
(2) hydrogen,
(3) halogen,
(4) $-OR^{11}$, (5) —CF₃,
(6) aryl,
(7) heteroaryl,
(8) cyano,
(9) —C(O)R¹¹,
(10) —C(O)OR¹¹,
(11) —C(O)N(R¹²)(R¹³),
(12) —N(R¹⁴)S(O)nR¹¹,
(13) —NR¹⁴C(O)R¹¹,
(14) —NR¹⁴C(O)OR¹¹,
(15) —N(R¹²)(R¹³),
(16) —S(O)nR¹¹,
(17) —S(O)₂OR¹¹,
(18) —OC(O)R¹¹,
(19) —OC(O)N(R¹²)(R¹³),
(20) —NO₂,
(21) C₃₋₇ cycloalkyl,
(22) cycloheteroalkyl,
(23) C₁₋₆ alkyl,
(24) C₂₋₆ alkenyl,
(25) C₂₋₆ alkynyl, and
(26) aryl-C₁₋₆ alkyl;
wherein alkyl, alkenyl, alkynyl are straight chain or branched; alkyl, alkenyl, alkynyl, cycloalkyl, cycloheteroalkyl and aryl are optionally substituted with one to four substituents selected from a group independently selected from $R^d$;

PROVIDED THAT at least one of $R^8$, $R^9$, and $R^{10}$ is $R^{15}$;

$R^{11}$ is selected from:
(1) C₁₋₄alkyl, straight chain or branched, unsubstituted or substituted with one to three $R^a$ substituents,
(2) aryl, unsubstituted or substituted with one to three $R^a$ substituents,
(3) aryl C₁₋₄alkyl, wherein alkyl is straight or branched chain, unsubstituted or substituted on one, two or three carbon atoms with one to three $R^a$ substituents, and
(4) —CF₃;

$R^{12}$ and $R^{13}$ are each independently selected from:
(1) hydrogen,
(2) C₁₋₈ alkyl, straight chain or branched, unsubstituted or substituted with one to three substituents selected from $R^a$,
(3) C₂₋₈ alkenyl, straight chain or branched,
(4) perfluoro C₁₋₆ alkyl, straight chain or branched,
(5) C₃₋₇cycloalkyl, unsubstituted or substituted with one to three substituents selected from $R^a$,
(6) cycloalkyl-C₁₋₆alkyl, wherein alkyl is straight chain or branched,
(7) cycloheteroalkyl,
(8) aryl, unsubstituted or substituted with one to three substituents selected from $R^a$,
(9) heteroaryl, unsubstituted or substituted on a carbon or nitrogen atom with one to three substituents selected from $R^a$,
(10) aryl C₁₋₆alkyl, wherein alkyl is straight chain or branched,
(11) heteroaryl C₁₋₆alkyl, wherein alkyl is straight chain or branched, or $R^{12}$ and $R^{13}$ together with the atom(s) to which they are attached form a heterocyclic ring of 4 to 7 members containing 0-2 additional heteroatoms independently selected from oxygen, sulfur and N-R¹⁴;

$R^{14}$ is selected from: hydrogen, C₁₋₆alkyl, and C₂₋₆alkenyl, straight chain or branched, unsubstituted or substituted with one to three halogen atoms;

each $R^{15}$ is a 5-membered unsaturated heterocyclic ring selected from:

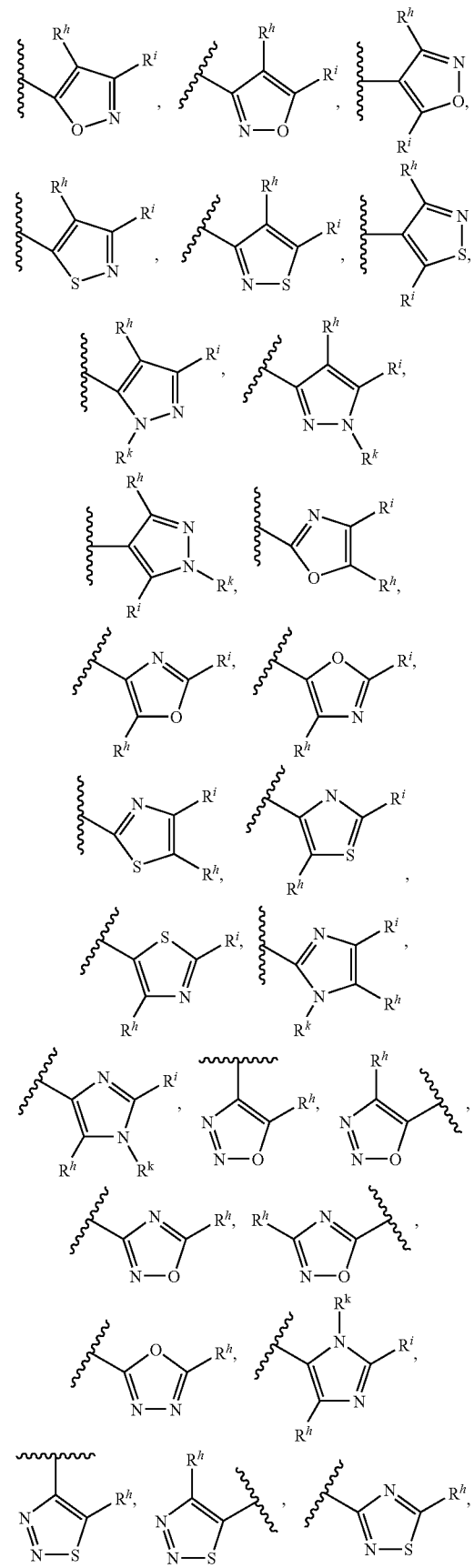

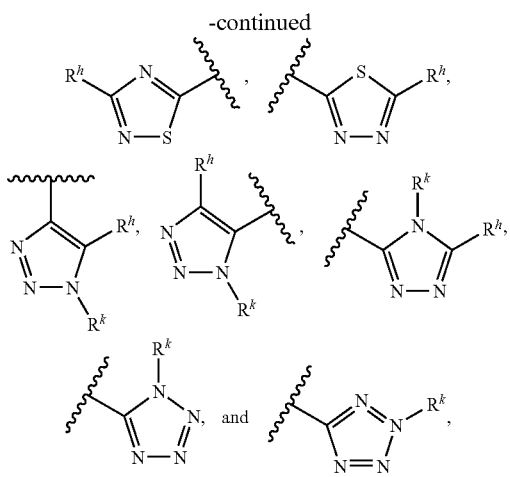

each $R^a$ is independently selected from:
(1) halogen,
(2) $N(R^e)(R^f)$,
(3) carboxy,
(4) $C_{1-4}$alkyl,
(5) $C_{1-4}$alkoxy,
(6) aryl,
(7) aryl $C_{1-4}$alkyl,
(8) hydroxy,
(9) $CF_3$,
(10) —$OC(O)C_{1-4}$alkyl, and
(11) aryloxy,
wherein alkyl is straight chain or branched;
each $R^b$ is independently selected from:
(1) halogen,
(2) —$R^{11}$,
(3) $CF_3$,
(4) aryl,
(5) heteroaryl,
(6) cyano,
(7) —$C(O)R^{11}$,
(8) —$C(O)OR^{11}$,
(9) —$C(O)N(R^e)(R^f)$,
(10) —$N(R^{14})S(O)_nR^{11}$,
(11) —$NR^{14}C(O)R^{11}$,
(12) —$NR^{14}C(O)OR^{11}$,
(13) —$N(R^e)(R^f)$,
(14) —$S(O)_nR^{11}$,
(15) —$S(O)_2OR^{11}$,
(16) —$OC(O)R^{11}$,
(17) —$OC(O)N(R^e)(R^f)$,
(18) —$NO_2$,
(19) $C_{3-7}$ cycloalkyl, and
(20) cycloheteroalkyl;
wherein cycloalkyl, cycloheteroalkyl, heteroaryl and aryl are optionally substituted with one to four substituents independently selected from $R^d$;
each $R^c$ is independently selected from:
(1) halogen,
(2) —$R^{11}$,
(3) —$CF_3$,
(4) aryl,
(5) heteroaryl,
(6) cyano,
(7) —$C(O)R^{11}$,
(8) —$C(O)OR^{11}$,
(9) —$C(O)N(R^{12})(R^{13})$,
(10) —$N(R^{14})S(O)nR^{11}$,
(11) —$NR^{14}C(O)R^{11}$,
(12) —$NR^{14}C(O)OR^{11}$,
(13) —$N(R^{12})(R^{13})$,
(14) —$S(O)nR^{11}$,
(15) —$S(O)_2OR^{11}$,
(16) —$OC(O)R^{11}$,
(17) —$OC(O)N(R^{12})(R^{13})$,
(18) —$NO_{12}$,
(19) $C_{3-7}$ cycloalkyl,
(20) cycloheteroalkyl,
(21) $C_{1-6}$ alkyl,
(22) $C_{2-6}$ alkenyl,
(23) $C_{2-6}$ alkynyl, and
(24) aryl-$C_{1-6}$ alkyl;
wherein alkyl, alkenyl, alkynyl are straight chain or branched; alkyl, alkenyl, alkynyl, cycloalkyl, cycloheteroalkyl and aryl are optionally substituted with one to four substituents independently selected from $R^d$;
each $R^d$ is independently selected from:
(1) halogen,
(2) —$NR^{12}R^{13}$
(3) $C_{1-4}$alkyl,
(4) $C_{1-4}$alkoxy,
(5) aryl,
(6) aryl $C_{1-4}$alkyl,
(7) hydroxy,
(8) $CF_3$,
(9) —$OCF_3$,
(10) —$C(O)R^{11}$,
(11) —$CO_2R^{11}$,
(12) —$C(O)NR^{12}R^{13}$,
(13) —$OC(O)C_{1-4}$alkyl,
(14) —$NR^{14}C(O)R^{11}$,
(15) —$OC(O)NR^{12}R^{13}$,
(16) —$NR^{14}C(O)OR^{11}$,
(17) —$NR^{14}C(O)NR^{12}R^{13}$,
(18) —$OC(O)NR^{12}R^{13}$, and
(19) aryloxy,
wherein alkyl is straight chain or branched;
$R^e$ and $R^f$ are each independently selected from:
(1) hydrogen,
(2) $C_{1-8}$ alkyl, straight chain or branched, unsubstituted or substituted with one to three substituents selected from halogen, hydroxyl, and $C_{1-6}$alkyloxy-,
(3) $C_{2-8}$ alkenyl, straight chain or branched,
(4) perfluoro $C_{1-6}$ alkyl, straight chain or branched,
(5) $C_{1-8}$ alkylcarbonyl-, straight chain or branched, unsubstituted or substituted on a carbon atom with one to three substituents selected from halogen, hydroxyl, and $C_{1-6}$alkyloxy-,
(6) $C_{1-8}$ alkylcarbonyloxy-, straight chain or branched, unsubstituted or substituted on a carbon atom with one to three substituents selected from halogen, hydroxyl, and $C_{1-6}$alkyloxy-,
(7) $C_{3-7}$cycloalkyl,
(8) cycloalkyl-$C_{1-6}$alkyl, wherein alkyl is straight chain or branched,
(9) cycloheteroalkyl,
(10) aryl, unsubstituted or substituted with one to three substituents selected from halogen, amino, carboxy, methyl, methoxy, hydroxy, trifluoromethyl, and methylcarbonyloxy,
(11) arylcarbonyl-, unsubstituted or substituted on a carbon atom with one to three substituents selected from halogen, amino, carboxy, methyl, methoxy, hydroxy, trifluoromethyl, and methylcarbonyloxy,

(12) arylcarbonyloxy-, unsubstituted or substituted on a carbon atom with one to three substituents selected from halogen, amino, carboxy, methyl, methoxy, hydroxy, trifluoromethyl, and methylcarbonyloxy,
(13) heteroaryl, unsubstituted or substituted on a carbon or nitrogen atom with one to three substituents selected from halogen, amino, carboxy, methyl, methoxy, hydroxy, trifluoromethyl, and methylcarbonyloxy,
(14) aryl $C_{1-6}$alkyl, wherein alkyl is straight chain or branched, and
(15) heteroaryl $C_{1-6}$alkyl, wherein alkyl is straight chain or branched, or $R^e$ and $R^f$ together with the atom(s) to which they are attached form a heterocyclic ring of 4 to 7 members containing 0-2 additional heteroatoms independently selected from oxygen, sulfur and N-$R^{14}$;

each $R^g$ is independently selected from:
(1) hydrogen,
(2) halogen,
(3) $R^{11}$,
(4) —$CF_3$,
(5) aryl,
(6) heteroaryl,
(7) cyano,
(8) —$C(O)R^{11}$,
(9) —$C(O)OR^{11}$,
(10) —$C(O)N(R^{12})(R^{13})$,
(11) —$N(R^{14})S(O)nR^{11}$,
(12) —$NR^{14}C(O)R^{11}$,
(13) —$NR^{14}C(O)OR^{11}$,
(14) —$N(R^{12})(R^{13})$,
(15) —$S(O)nR^{11}$,
(16) —$S(O)_2OR^{11}$,
(17) —$OC(O)R^{11}$,
(18) —$OC(O)N(R^{12})(R^{13})$,
(19) —$NO_2$,
(20) $C_{3-7}$ cycloalkyl,
(21) cycloheteroalkyl,
(22) $C_{1-6}$ alkyl,
(23) $C_{2-6}$ alkenyl,
(24) $C_{2-6}$ alkynyl, and
(25) aryl-$C_{1-6}$ alkyl;
wherein alkyl, alkenyl, alkynyl are straight chain or branched; alkyl, alkenyl, alkynyl, cycloalkyl, cycloheteroalkyl and aryl are optionally substituted with one to four substituents independently selected from $R^d$;

each $R^h$ is independently selected from:
(1) —H,
(2) —OH,
(3) —SH,
(4) —$NH_2$,
(5) $C_{1-3}$ alkyl, and
(6) —$CF_3$;

each $R^i$ is independently selected from:
(1) —H,
(2) —OH,
(3) —SH,
(4) —$NH_2$,
(5) $C_{1-3}$ alkyl, and
(6) —$CF_3$;

each $R^k$ is independently selected from:
(1) —H, and
(2) $C_{1-3}$ alkyl;

n is selected from 0, 1, and 2;
or a pharmaceutically acceptable salt or solvate thereof.

In one embodiment of the present invention, $Ar^1$ is selected from:

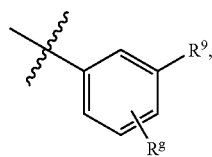

(1)

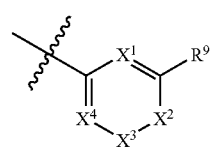

(2)

wherein one of $X^1$, $X^2$, $X^3$, and $X^4$ is —N—, and the others are each selected from —H—, and —C($R^c$)—, provided that only one of $X^1$, $X^2$, $X^3$ and $X^4$ is —C($R^c$)—,

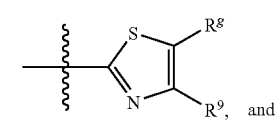

(3)

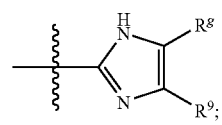

(4)

In one class, $Ar^1$ is selected from:

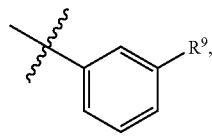

(1)

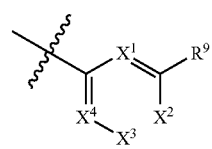

(2)

wherein one of $X^1$, $X^2$, $X^3$, and $X^4$ is N, and the others are each —CH—,

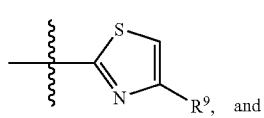

(3)

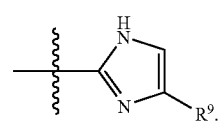

(4)

In one class of this embodiment, $Ar^1$ is selected from:

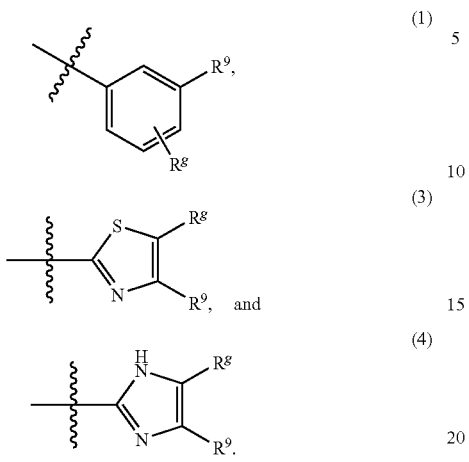

In a subclass of this class, $Ar^1$ is:

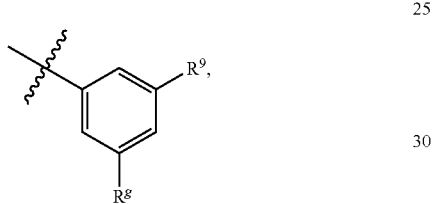

wherein $R^g$ is selected from hydrogen, halogen, methyl, trifluoromethyl, cyano, —S(O)$_n$R$^{11}$, and —NHSO$_2$CH$_3$, and $R^9$ is selected from $R^{15}$, hydrogen, halogen, methyl, trifluoromethyl, cyano, —S(O)$_n$R$^{11}$, and —NHSO$_2$CH$_3$.

In a subclass of this class, $Ar^1$ is:

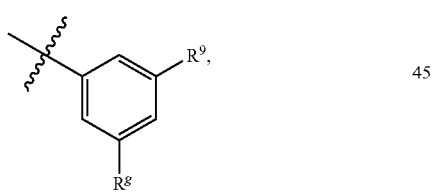

wherein $R^g$ is hydrogen, and $R^9$ is selected from $R^{15}$, hydrogen, and cyano.

In another subclass of this class, $Ar^1$ is:

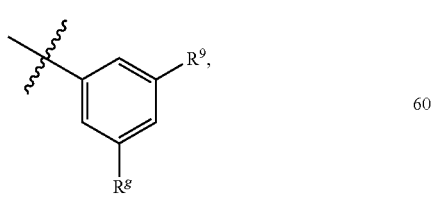

wherein $R^g$ is hydrogen, and $R^9$ is selected from $R^{15}$, hydrogen, and cyano.

In yet another subclass of this class, $AR^1$ is:

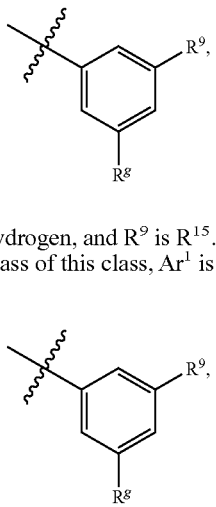

wherein $R^g$ is hydrogen, and $R^9$ is $R^{15}$.
In another subclass of this class, $Ar^1$ is:

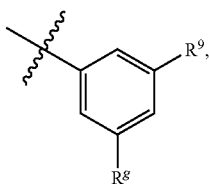

wherein $R^g$ is hydrogen, and $R^9$ is selected from hydrogen, and cyano.

In yet another subclass, $Ar^1$ is selected from:
(1) phenyl,
(2) 3-cyano-phenyl,
(3) 3-(5-oxo-4,5-dihydro-1,3,4-oxadiazol-2-yl)-phenyl,
(4) 3-(1,3,4-oxadiazol-2-yl)-phenyl,
(5) 3-(5-amino-1,3,4-oxadiazol-2-yl)-phenyl, and
(6) 3-(1,2,4-oxadiazoly-3-yl)-phenyl.

In one embodiment of the present application, $Ar^2$ is selected from:

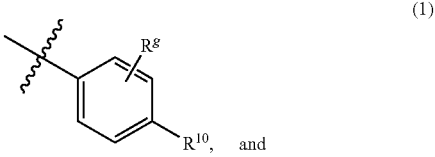

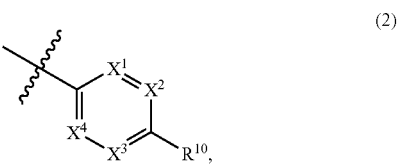

wherein one of $X^1$, $X^2$, $X^3$, and $X^4$ is —N—, and the others are each selected from —CH—, and —C(R$^c$)—, provided that only one of $X^1$, $X^2$, $X^3$ and $X^4$ is —C(R$^c$)—.

In another embodiment of the present invention, $AR^2$ is selected from:

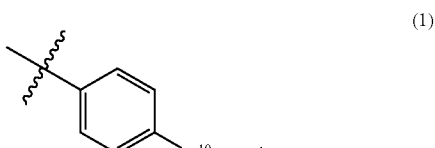

-continued

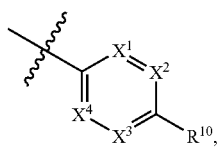
(2)

wherein one of $X^1$, $X^2$, $X^3$, and $X^4$ is —N—, and the others are each —CH—.

In one class of the present invention, $Ar^2$ is:

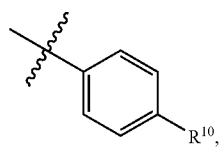

wherein $R^{10}$ is selected from: $R^{15}$, hydrogen, halogen, $C_{1-3}$ alkyl, trifluoromethyl, cyano, —S(O)$_n R^{10}$, and —NHSO$_2$CH$_3$.

In another class of the present invention, $Ar^2$ is:

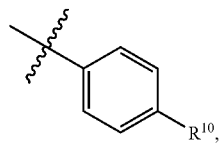

wherein $R^{10}$ is selected from: $R^{15}$, hydrogen, halogen, and cyano.

In another class of the present invention, $Ar^2$ is:

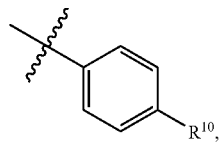

wherein $R^{10}$ is selected from: $R^{15}$, hydrogen, chloro, and cyano.

In another class of the present invention, $Ar^2$ is:

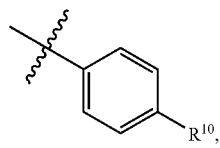

wherein $R^{10}$ is $R^{15}$.

In another class of the present invention, $Ar^2$ is:

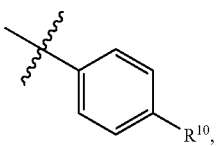

wherein $R^{10}$ is selected from: hydrogen, chloro, and cyano.
In another class of the present invention, $Ar^2$ is:

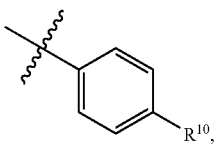

wherein $R^{10}$ is chloro.
In a subclass, $Ar^2$ is selected from:
(1) phenyl,
(2) 4-cyano-phenyl,
(3) 4-chloro-phenyl,
(4) 4-(5-oxo-4,5-dihydro-1,3,4-oxadiazol-2-yl)-phenyl,
(5) 4-(1,3,4-oxadiazol-2-yl)-phenyl,
(6) 4-(5-amino-1,3,4-oxadiazol-2-yl)-phenyl, and
(7) 4-(1,2,4-oxadiazoly-3-yl)-phenyl.
In another subclass, $Ar^2$ is 4-chlorophenyl.
In one embodiment of the present invention, X is selected from:
(1) hydroxy,
(2) $C_{1-6}$alkyl, straight chain or branched, unsubstituted or substituted with one to two $R^b$ substituents,
(3) perfluoro $C_{1-6}$alkyl,
(4) $C_{2-6}$alkenyl, straight chain or branched, unsubstituted or substituted with one to two $R^b$ substituents,
(5) $C_{2-6}$alkynyl, straight chain or branched, unsubstituted or substituted with one to two $R^b$ substituents,
(6) cyano,
(7) —C(O)$R^{11}$,
(8) —C(O)O$R^{12}$,
(9) —C(O)N($R^{12}$)($R^{13}$),
(10) —N($R^{14}$)S(O)$_n R^{11}$,
(11) —N$R^{14}$C(O)$R^{11}$,
(12) —N$R^{14}$C(O)O$R^{11}$,
(13) —N($R^{12}$)($R^{13}$),
(14) —S(O)$_n R^{11}$,
(15) —O$R^{11}$,
(16) —OC(O)$R^{11}$, and
(17) —OC(O)N($R^{12}$)($R^{13}$).
In one class of this embodiment, X is selected from:
(1) hydroxy,
(2) $C_{1-6}$alkyl, straight chain or branched, unsubstituted or substituted with one or two $R^b$ substituents,
(3) trifluoromethyl,
(4) $C_{2-6}$alkenyl, straight chain or branched, unsubstituted or substituted with one to two $R^b$ substituents,
(5) cyano,
(6) —C(O)R 1,
(7) —C(O)O$R^{11}$,
(8) —C(O)N($R^{12}$)($R^{13}$),
(9) —N($R^{14}$)S(O)$_n R^{11}$,
(10) —N$R^{14}$C(O)$R^{11}$,
(11) —N$R^{14}$C(O)O$R^{11}$,
(12) —N($R^{12}$)($R^{13}$),
(13) —S(O)$_2 R^{11}$,

(14) —OR$^{11}$,
(15) —OC(O)R$^{11}$, and
(16) —OC(O)N(R$^{12}$)(R$^{13}$).

In one subclass of this class, X is selected from:
(1) hydroxy,
(2) C$_{1-4}$alkyl, straight chain or branched, unsubstituted or substituted with a substituent selected from halogen, hydroxy, and methoxy,
(3) trifluoromethyl,
(4) C$_{2-4}$alkenyl, straight chain or branched,
(5) cyano,
(6) —C(O)CH$_3$,
(7) —C(O)OH,
(8) —C(O)OCH$_3$,
(9) —C(O)N(R$^{12}$)(R$^{13}$),
(10) —NHS(O)$_2$R$^{11}$,
(11) —NHC(O)R$^{11}$,
(12) —NHC(O)OR$^{11}$,
(13) —N(R$^{12}$)(R$^{13}$),
(14) —S(O)$_2$R$^{11}$,
(15) —OR$^{11}$,
(16) —OC(O)R$^{11}$, and
(17) —OC(O)N(R$^{12}$)(R$^{13}$).

In another subclass of this class, X is selected from:
(1) hydroxy,
(2) methyl,
(3) ethyl,
(4) isopropyl,
(5) t-butyl,
(6) sec-butyl,
(7) n-butyl,
(8) hydroxymethyl—
(9) trifluoromethyl,
(10) allyl,
(11) cyano,
(12) —C(O)CH$_3$,
(13) —C(O)OH,
(14) —C(O)OCH$_3$,
(15) —C(O)N(CH$_3$)$_2$,
(16) —C(O)NH—CH(CH$_3$)$_2$,
(17) —NHS(O)$_2$C(CH$_3$)$_3$,
(18) —N(CH$_3$)$_2$,
(19) —NH$_2$,
(20) —NH—CH(CH$_3$)$_2$
(21) —OC(O)CH$_3$,
(22) —OC(O) N(CH$_3$)$_2$, and
(23) —OC(O)NH—CH(CH$_3$)$_2$.

In yet another subclass of this class, X is selected from:
(1) hydroxy,
(2) NH$_2$,
(3) methyl, and
(4) methoxy.

In yet another subclass of this class, X is methyl.

In one embodiment of the present invention, Y is selected from:
(1) hydrogen,
(2) hydroxy,
(3) C$_{1-3}$ alkyloxy,
(4) fluoro,
(5) C$_{1-3}$ alkyl,
(6) trifluoromethyl, and
(7) —N(R$^{12}$)(R$^{13}$).

In one class of this embodiment, Y is selected from:
(1) hydrogen,
(2) hydroxy,
(3) methoxy,
(4) fluoro,
(5) methyl,
(6) trifluoromethyl, and
(7) —NH$_2$.

In one subclass of this class, Y is selected from:
(1) hydrogen,
(2) hydroxy,
(3) fluoro, and
(4) methoxy.

In another subclass of this class, Y is selected from:
(1) hydrogen,
(2) hydroxy, and
(3) fluoro.

In another subclass of this class, Y is hydrogen.

In one embodiment of the present invention, Z is selected from hydrogen, hydroxy, methoxy, fluoro, methyl, and —N(R$^{12}$)(R$^{13}$).

In one class of this embodiment, Z is selected from hydrogen, hydroxy, fluoro, methyl, and —NH$_2$.

In one subclass of this class, Z is selected from hydrogen and hydroxy.

In still another subclass of this class, Z is hydrogen.

In one embodiment of the present invention, R$^1$ is selected from:

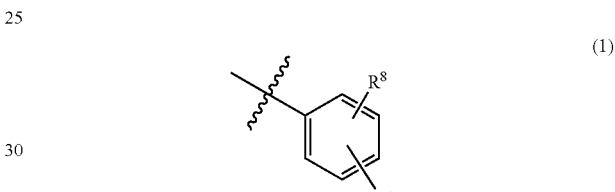

(1)

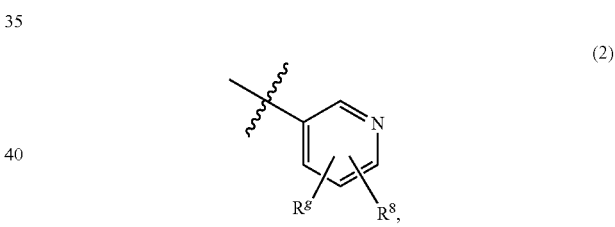

(2)

wherein R$^8$ and R$^g$ are bonded to a carbon atom of the ring,

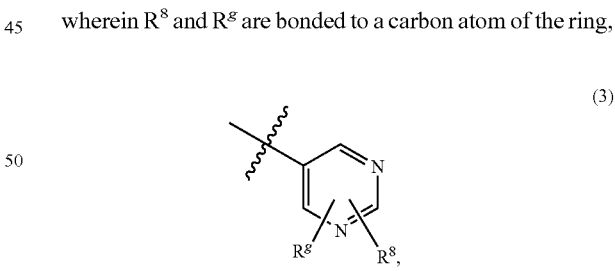

(3)

wherein R$^8$ and R$^g$ are bonded to a carbon atom of the ring,

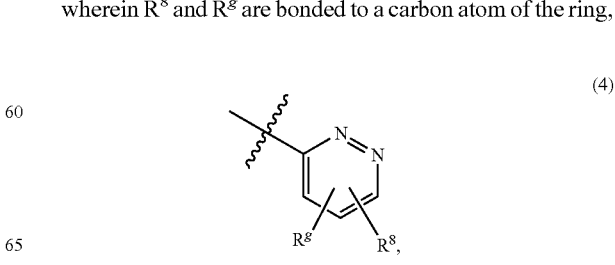

(4)

wherein $R^8$ and $R^g$ are bonded to a carbon atom of the ring, (5)

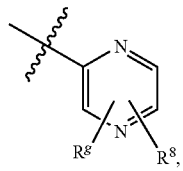

wherein $R^8$ and $R^g$ are bonded to a carbon atom of the ring, (6)

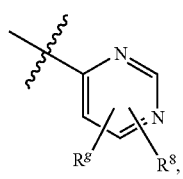

wherein $R^8$ and $R^g$ are bonded to a carbon atom of the ring, (7)

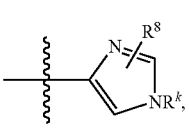

wherein $R^8$ is bonded to a carbon atom of the ring, (8)

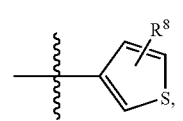

wherein $R^8$ is bonded to a carbon atom of the ring, and (9)

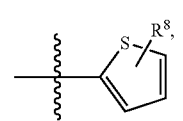

wherein $R^8$ is bonded to a carbon atom of the ring.

In one class of this embodiment, $R^1$ is selected from:

(1)

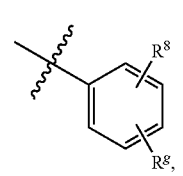

-continued (2)

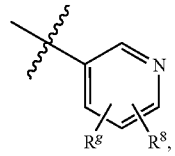

wherein $R^8$ and $R^g$ are bonded to a carbon atom of the ring, (3)

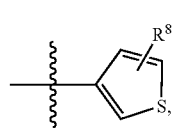

wherein $R^8$ is bonded to a carbon atom of the ring, (4)

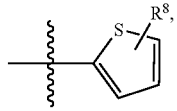

wherein $R^8$ is bonded to a carbon atom of the ring, and (5)

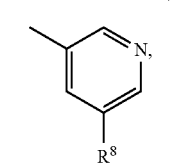

wherein $R^8$ is bonded to a carbon atom of the ring.

In one class of this embodiment, $R^1$ is selected from:

(1)

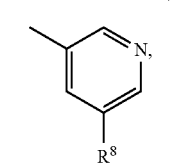

(2)

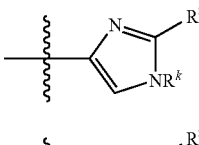

(3)

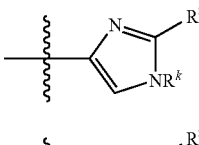

(4)

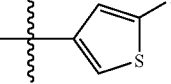

-continued (5)
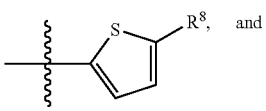 and (6)
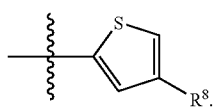

In another class of this embodiment, $R^1$ is:

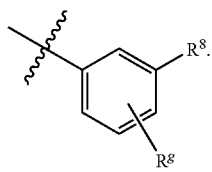

In another class of this embodiment, $R^1$ is:

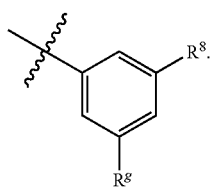

In a subclass of this class, $R^1$ is:

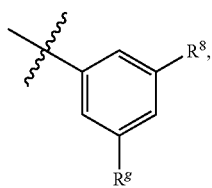

wherein $R^8$ is selected from $R^{15}$, fluoro, and cyano, and $R^g$ is halogen.

In another subclass of this class, $R^1$ is:

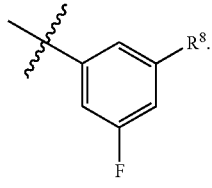

In a subclass of this class, $R^1$ is:

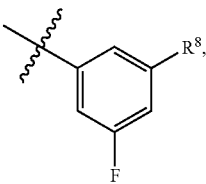

wherein $R^8$ is selected from $R^{15}$, fluoro, and cyano.
In a subclass of this class, $R^1$ is:

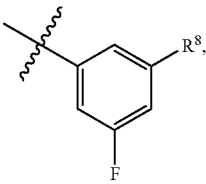

wherein $R^8$ is selected from fluoro, and cyano.
In still another subclass of this class, $R^1$ is:

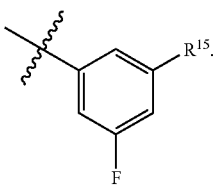

In still another subclass of this class, $R^1$ is:

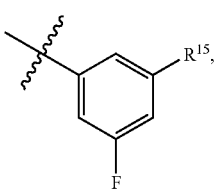

wherein $R^{15}$ is selected from:

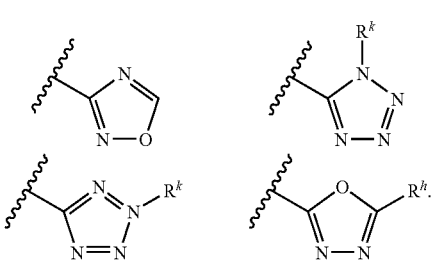

In one embodiment of the present invention, $R^2$ is selected from:
(1) hydrogen,
(2) $C_{1-6}$alkyl, straight chain or branched, unsubstituted or substituted with one or two $R^b$ substituents,
(3) fluoro, (4) hydroxyl,
(5) perfluoro $C_{1-6}$alkyl, straight chain or branched; and
$R^3$ is selected from:
(1) hydrogen,
(2) $C_{1-6}$alkyl, straight chain or branched, unsubstituted or substituted with one or two $R^b$ substituents,
(3) fluoro,
(4) hydroxy,
(5) perfluoro $C_{1-6}$alkyl, straight chain or branched;
or $R^2$ and $R^3$, together with the carbon atom to which they are attached, form a carbonyl group, or a 3 to 7 membered carbocyclic ring;
provided that when X is hydroxy, —$NR^{14}C(O)R^{11}$, —$NR^{14}C(O)OR^{11}$, —$N(R^{12})(R^{13})$, or $OR^{11}$, then:
(1) $R^2$ and $R^3$ are not both hydrogen, and
(2) $R^2$ and $R^3$ do not form a carbonyl group together with the carbon to which they are attached.

In one embodiment of the present invention, $R^2$ and $R^3$, together with the carbon atom to which they are attached, form a carbonyl group, provided that X is not selected from the group consisting of: hydroxy, —$NR^{14}C(O)R^{11}$, —$NR^{14}C(O)OR^{11}$, —$N(R^{12})(R^{13})$, or $OR^{11}$.

In another embodiment of the present invention, $R^2$ and $R^3$, together with the carbon atom to which they are attached, form a 3 to 7 membered carbocyclic ring system.

In one class of this embodiment, $R^2$ and $R^3$, together with the carbon atom to which they are attached, form a 3, 4, or 5-membered carbocyclic ring.

In one subclass of this class, $R^2$ and $R^3$, together with the carbon atom to which they are attached, form a 4-membered carbocyclic ring.

In another embodiment of the present invention, $R^2$ and $R^3$ are each independently selected from:
(1) hydrogen,
(2) $C_{1-6}$alkyl, straight chain or branched, unsubstituted or substituted with one or two $R^b$ substituents,
(3) fluoro,
(4) hydroxyl, and
(5) perfluoro $C_{1-6}$alkyl, straight chain or branched,
provided that $R^2$ and $R^3$ are not both hydrogen when X is hydroxy, —$NR^{14}C(O)R^{11}$, —$NR^{14}C(O)OR^{11}$, —$N(R^{12})(R^{13})$, or $OR^{11}$.

In a class of this embodiment, $R^2$ and $R^3$ are each independently selected from:
(1) hydrogen,
(2) methyl,
(3) fluoro,
(4) hydroxyl, and
(5) trifluoromethyl,
provided that $R^2$ and $R^3$ are not both hydrogen when X is hydroxy, —$NR^{14}C(O)R^{11}$, —$NR^{14}C(O)OR^{11}$. —$N(R^{12})(R^{13})$, or $OR^{11}$.

In a subclass of this class, $R^2$ is selected from:
(1) hydrogen,
(2) methyl, and
(3) hydroxyl, and
$R^3$ is selected from:
(1) methyl, and
(2) hydroxyl.

In another subclass, $R^2$ is selected from:
(1) hydrogen,
(2) fluoro,
(3) methyl, and
(4) hydroxyl, and
$R^3$ is selected from methyl, and hydroxyl.

In another subclass of the present invention, $R^2$ and $R^3$ are each fluoro.

In still another subclass of the present invention, $R^2$ is fluoro and $R^3$ is methyl.

In one embodiment of the present invention, $R^4$, $R^5$, $R^6$, and $R^7$ are each independently selected from: hydrogen, $C_{1-6}$ alkyl, unsubstituted or substituted with $R^b$, and $C_{2-6}$ alkenyl, unsubstituted or substituted with $R^b$.

In one class of this embodiment, $R^4$, $R^5$, $R^6$, and $R^7$ are each independently selected from: hydrogen, methyl and $C_2$ alkenyl.

In one subclass of this class, one of $R^4$, $R^5$, $R^6$, and $R^7$ is methyl and the other three are each hydrogen.

In another subclass of this class, $R^4$, $R^5$, $R^6$, and $R^7$ are each hydrogen.

In one embodiment of the present invention, $R^8$ is selected from:
(1) $R^{15}$,
(2) hydrogen,
(3) halogen,
(4) —$OR^{11}$,
(5) —$CF_3$,
(6) aryl,
(7) heteroaryl,
(8) cyano,
(9) —$C(O)R^{11}$,
(10) —$C(O)OR^{11}$,
(11) —$C(O)N(R^{12})(R^{13})$,
(12) —$N(R^{14})S(O)nR^{11}$,
(13) —$NR^{14}C(O)R^{11}$,
(14) —$NR^{14}C(O)OR^{11}$,
(15) —$N(R^{12})(R^{13})$,
(16) —$S(O)nR^{11}$,
(17) —$S(O)_2OR^{11}$,
(18) —$OC(O)R^{11}$,
(19) —$OC(O)N(R^{12})(R^{13})$,
(20) —$NO_2$,
(21) $C_{3-7}$ cycloalkyl,
(22) cycloheteroalkyl,
(23) $C_{1-6}$alkyl,
(24) $C_{2-6}$ alkenyl,
(25) $C_{2-6}$ alkynyl, and
(26) aryl-$C_{1-6}$ alkyl;
wherein alkyl, alkenyl, alkynyl are straight chain or branched; alkyl, alkenyl, alkynyl, cycloalkyl, cycloheteroalkyl and aryl are optionally substituted with one to four substituents selected from a group independently selected from $R^d$.

In one class, $R^8$ is selected from:
(1) $R^{15}$,
(2) hydrogen,
(3) halogen,
(4) methyl,
(5) —$CF_3$,
(6) cyano, and
(7) $SO_2CH_3$.

In one subclass, $R^8$ is selected from:
(1) $R^{15}$,
(2) hydrogen,
(3) halogen,
(4) chloro,
(5) fluoro, and
(6) cyano.

In another subclass, $R^8$ is selected from:
(1) $R^{15}$,
(2) hydrogen,
(3) chloro,
(4) fluoro, and
(5) cyano.

In another subclass, $R^8$ is selected from:
(1) $R^{15}$,
(2) fluoro, and
(3) cyano.
In another subclass, $R^8$ is $R^{15}$.
In another subclass, $R^8$ is selected from:

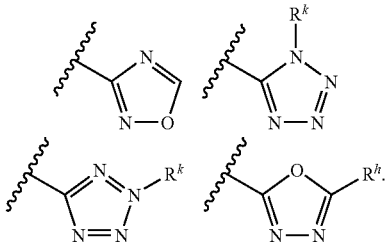

In another subclass, $R^8$ is selected from:
(1) fluoro, and
(2) cyano.
In another embodiment of the present invention, $R^9$ is selected from:
(1) $R^{15}$,
(2) hydrogen,
(3) halogen,
(4) —$OR^{11}$,
(5) —$CF_3$,
(6) aryl,
(7) heteroaryl,
(8) cyano,
(9) —$C(O)R^{11}$,
(10) —$C(O)OR^{11}$,
(11) —$C(O)N(R^{12})(R^{13})$,
(12) —$N(R^{14})S(O)nR^{11}$,
(13) —$NR^{14}C(O)R^{11}$,
(14) —$NR^{14}C(O)OR^{11}$,
(15) —$N(R^{12})(R^{13})$,
(16) —$S(O)nR^{11}$,
(17) —$S(O)_2OR^{11}$,
(18) —$OC(O)R^{11}$,
(19) —$OC(O)N(R^{12})(R^{13})$,
(20) —$NO_2$,
(21) $C_{3-7}$ cycloalkyl,
(22) cycloheteroalkyl,
(23) $C_{1-6}$ alkyl,
(24) $C_{2-6}$ alkenyl,
(25) $C_{2-6}$ alkynyl, and
(26) aryl-$C_{1-6}$alkyl;
wherein alkyl, alkenyl, alkynyl are straight chain or branched; alkyl, alkenyl, alkynyl, cycloalkyl, cycloheteroalkyl and aryl are optionally substituted with one to four substituents selected from a group independently selected from $R^d$;
In a class of this embodiment, $R^9$ is selected from:
(1) $R^{15}$,
(2) hydrogen,
(3) halogen,
(4) cyano,
(5) —$CF_3$,
(6) $C_{1-3}$ alkyl,
(7) —$S(O)_nR^{11}$, and
(8) —$NHSO_2CH_3$.
In another class, $R^9$ is selected from:
(1) $R^{15}$,
(2) hydrogen,
(3) halogen,
(4) cyano,
(5) —$CF_3$,
(6) methyl, and
(7) —$S(O)_nR^{11}$.
In still another class, $R^9$ is selected from:
(1) $R^{15}$,
(2) hydrogen,
(3) halogen,
(4) cyano, and
(5) —$S(O)_nR^{11}$.
In yet another class, $R^9$ is selected from:
(1) $R^{15}$,
(2) hydrogen,
(3) fluoro
(4) chloro, and
(5) cyano.
In one subclass, $R^9$ is selected from:
(1) $R^{15}$,
(2) hydrogen, and
(3) cyano.
In another subclass, $R^9$ is $R^{15}$.
In still another subclass, $R^9$ is selected from:

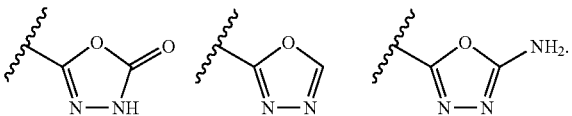

In still another subclass, $R^9$ is:

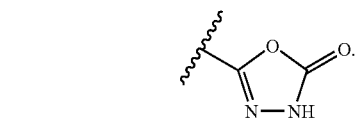

In another subclass, $R^9$ is selected from:
(1) hydrogen, and
(2) cyano.
In one embodiment of the present invention, $R^{10}$ is selected from:
(1) $R^{15}$,
(2) hydrogen,
(3) halogen,
(4) —$OR^{11}$,
(5) —$CF_3$,
(6) aryl,
(7) heteroaryl,
(8) cyano,
(9) —$C(O)R^{11}$,
(10) —$C(O)OR^{11}$,
(11) —$C(O)N(R^{12})(R^{13})$,
(12) —$N(R^{14})S(O)nR^{11}$,
(13) —$NR^{14}C(O)R^{11}$,
(14) —$NR^{14}C(O)OR^{11}$,
(15) —$N(R^{12})(R^{13})$,
(16) —$S(O)nR^{11}$,
(17) —$S(O)_2OR^{11}$,
(18) —$OC(O)R^{11}$,
(19) —$OC(O)N(R^{12})(R^{13})$,
(20) —$NO_2$,
(21) $C_{3-7}$ cycloalkyl,
(22) cycloheteroalkyl,

(23) $C_{1-6}$ alkyl,
(24) $C_{2-6}$ alkenyl,
(25) $C_{2-6}$ alkynyl, and
(26) aryl-$C_{1-6}$ alkyl;
wherein alkyl, alkenyl, alkynyl are straight chain or branched; alkyl, alkenyl, alkynyl, cycloalkyl, cycloheteroalkyl and aryl are optionally substituted with one to four substituents selected from a group independently selected from $R^a$.

In one class of this embodiment, $R^{10}$ is selected from:
(1) $R^{15}$,
(2) hydrogen,
(3) halogen,
(4) —$CF_3$,
(5) cyano,
(6) $C_{1-3}$ alkyl,
(7) —$S(O)_nR^{10}$, and
(8) —$NHSO_2CH_3$.

In another class of this embodiment, $R^{10}$ is selected from:
(1) $R^{15}$,
(2) hydrogen,
(3) fluoro,
(4) chloro,
(5) —$CF_3$,
(6) cyano, and
(7) methyl.

In another class of this embodiment, $R^{10}$ is selected from:
(1) $R^{15}$,
(2) hydrogen,
(3) halogen, and
(4) cyano.

In another class of this embodiment, $R^{10}$ is selected from:
(1) $R^{15}$,
(2) hydrogen,
(3) chloro, and
(4) cyano.

In a subclass, $R^{10}$ is $R^{15}$.
In another subclass, $R^{10}$ is:

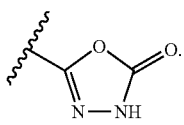

In another subclass, $R^{10}$ is selected from:
(1) hydrogen,
(2) chloro, and
(3) cyano.

In yet another subclass, $R^{10}$ is chloro.

In one embodiment of the present invention, $R^{11}$ is selected from:
(1) $C_{1-4}$alkyl, straight chain or branched, unsubstituted or substituted with one to three $R^a$ substituents,
(2) aryl, unsubstituted or substituted with one to three $R^a$ substituents,
(3) aryl $C_{1-4}$alkyl, wherein alkyl is straight or branched chain, unsubstituted or substituted on one, two or three carbon atoms with one to three $R^a$ substituents, and
(4) —$CF_3$.

In one class of this embodiment, $R^{11}$ is selected from:
(1) $C_{1-4}$alkyl, straight chain or branched, unsubstituted or substituted with one to three $R^a$ substituents,
(2) phenyl, unsubstituted or substituted with one to three $R^a$ substituents,
(3) benzyl, wherein the phenyl group is substituted with one to three $R^a$ substituents, and
(4) —$CF_3$.

In one subclass of this class, $R^{11}$ is selected from:
(1) $C_{1-4}$alkyl, straight chain or branched,
(2) phenyl, unsubstituted or substituted with one or two $R^a$ substituents, and
(3) —$CF_3$.

In one embodiment of the present invention, $R^{12}$ and $R^{13}$ are each independently selected from:
(1) hydrogen,
(2) $C_{1-8}$ alkyl, straight chain or branched, unsubstituted or substituted with one to three substituents selected from $R^a$,
(3) $C_{2-8}$ alkenyl, straight chain or branched,
(4) perfluoro $C_{1-6}$ alkyl, straight chain or branched,
(5) $C_{3-7}$cycloalkyl, unsubstituted or substituted with one to three substituents selected from $R^a$,
(6) cycloalkyl-$C_{1-6}$alkyl, wherein alkyl is straight chain or branched,
(7) cycloheteroalkyl,
(8) aryl, unsubstituted or substituted with one to three substituents selected from $R^a$,
(9) heteroaryl, unsubstituted or substituted on a carbon or nitrogen atom with one to three substituents selected from $R^a$,
(10) aryl $C^{1-6}$alkyl, wherein alkyl is straight chain or branched,
(11) heteroaryl $C^{1-6}$alkyl, wherein alkyl is straight chain or branched, or $R^{12}$ and $R^{13}$ together with the atom(s) to which they are attached form a heterocyclic ring of 4 to 7 members containing 0-2 additional heteroatoms independently selected from oxygen, sulfur and N-$R^{14}$;

In one embodiment of the present invention, $R^{12}$ and $R^{13}$ together with the atom(s) to which they are attached form a heterocyclic ring of 4 to 7 members containing 0-2 additional heteroatoms independently selected from oxygen, sulfur and N-$R^{14}$.

In one class of this embodiment, $R^{12}$ and $R^{13}$ together with the atom(s) to which they are attached form a heterocyclic ring of 5 to 6 members.

In another embodiment of the present invention, $R^{12}$ and $R^{13}$ are each independently selected from:
(1) hydrogen,
(2) $C_{1-8}$ alkyl, straight chain or branched, unsubstituted or substituted with one to three substituents selected from $R^a$,
(3) $C_{2-8}$ alkenyl, straight chain or branched,
(4) perfluoro $C_{1-6}$ alkyl, straight chain or branched,
(5) $C_{3-7}$cycloalkyl, unsubstituted or substituted with one to three substituents selected from $R^a$,
(6) cycloalkyl-$C_{1-6}$alkyl, wherein alkyl is straight chain or branched,
(7) cycloheteroalkyl,
(8) aryl, unsubstituted or substituted with one to three substituents selected from $R^a$,
(9) heteroaryl, unsubstituted or substituted on a carbon or nitrogen atom with one to three substituents selected from $R^a$,
(10) aryl $C_{1-6}$alkyl, wherein alkyl is straight chain or branched, and
(11) heteroaryl $C_{1-6}$alkyl, wherein alkyl is straight chain or branched.

In a class of this embodiment, $R^{12}$ and $R^{13}$ are each independently selected from:
(1) hydrogen,
(2) $C_{1-6}$ alkyl, straight chain or branched, unsubstituted or substituted with one or two substituents selected from $R^a$,
(3) $C_{2-6}$ alkenyl, straight chain or branched,
(4) trifluoromethyl,
(5) $C_{3-7}$cycloalkyl, unsubstituted or substituted with one to three substituents selected from $R^a$,
(6) cycloalkyl-methyl,
(7) cycloheteroalkyl,
(8) phenyl, unsubstituted or substituted with one to three substituents selected from $R^a$,
(9) pyridyl, unsubstituted or substituted on a carbon or nitrogen atom with one to three substituents selected from $R^a$,
(10) benzyl, and
(11) pyridylmethyl.

In a subclass of this class, $R^{12}$ and $R^{13}$ are each independently selected from:
(1) hydrogen,
(2) $C_{1-4}$ alkyl, straight chain or branched, unsubstituted or substituted with one or two substituents selected from $R^a$,
(3) trifluoromethyl,
(4) phenyl,
(5) pyridyl, and
(6) benzyl.

In a subclass of this class, $R^{12}$ and $R^{13}$ are each independently selected from:
(1) hydrogen,
(2) methyl, and
(3) isopropyl.

In one embodiment of the present invention, $R^{14}$ is selected from: hydrogen, $C_{1-6}$alkyl, and $C_{2-6}$alkenyl, straight chain or branched, unsubstituted or substituted with one to three halogen atoms.

In one class of this embodiment, $R^{14}$ is selected from: hydrogen, and $C_{1-6}$alkyl, straight chain or branched, unsubstituted or substituted with one to three halogen atoms.

In a subclass of this class, $R^{14}$ is selected from: hydrogen, $C_{1-6}$alkyl, straight chain or branched, and trifluoromethyl.

In another subclass of this class, $R^{14}$ is selected from: hydrogen and methyl.

In yet another subclass, $R^{14}$ is hydrogen.

In one embodiment of the present invention, each $R^{15}$ is a 5-membered unsaturated heterocyclic ring selected from:

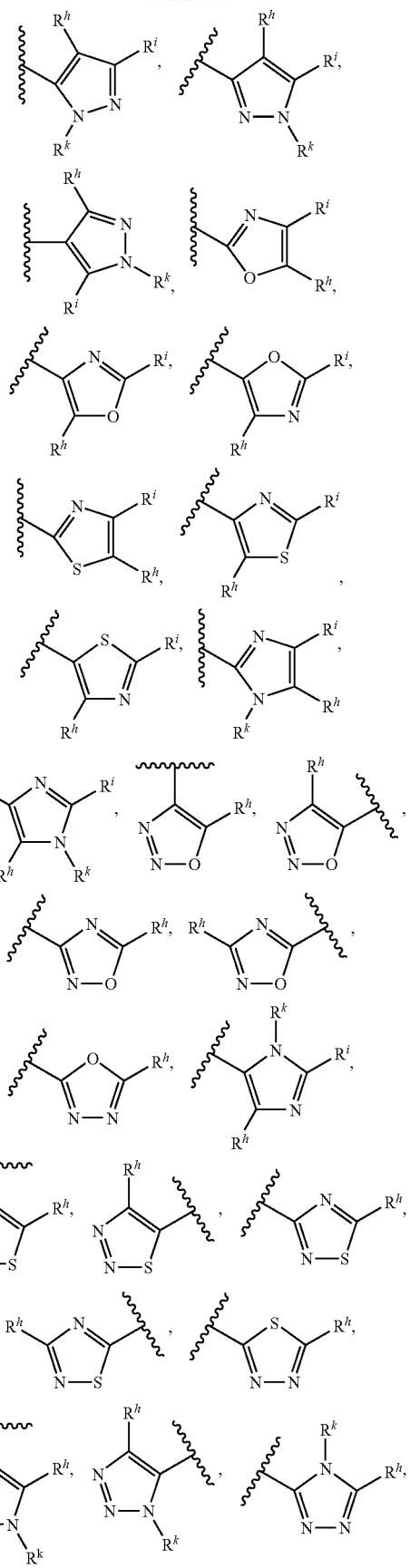

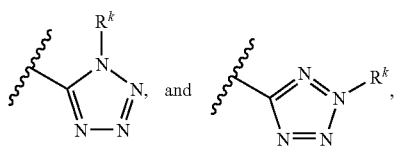, and 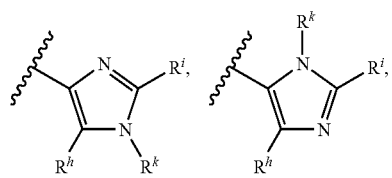

wherein: $R^h$ and $R^i$ are each independently selected from: —H, —OH, —SH, —NH$_2$, C$_{1-3}$ alkyl, —CF$_3$; and each $R^k$ is selected from: —H, and C$_{1-3}$ alkyl.

The substructures above can be considered to represent all possible tautomeric structures of the individual ring systems. For example:

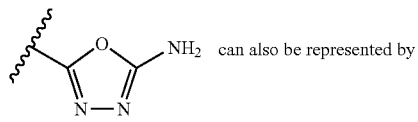 can also be represented by

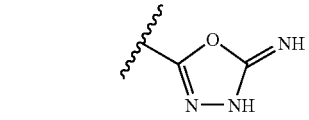

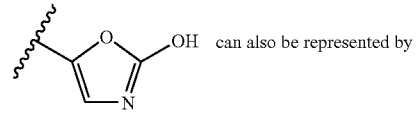 can also be represented by

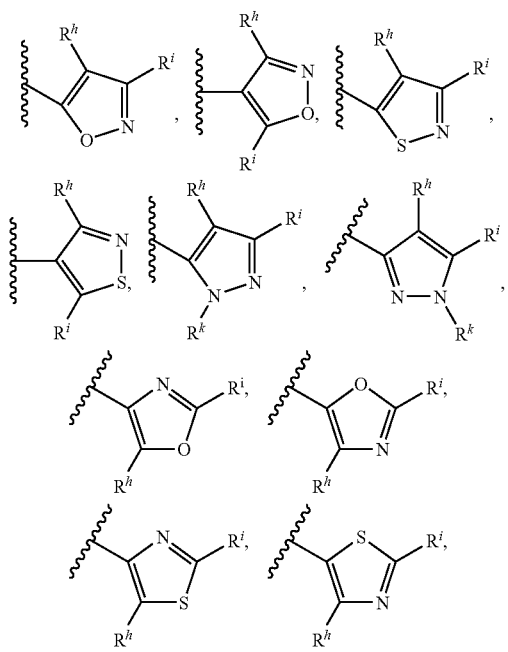

In one class of the present invention, each $R^{15}$ is independently selected from:

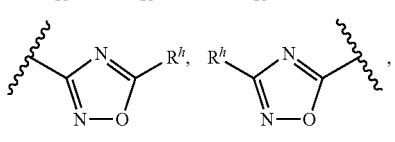

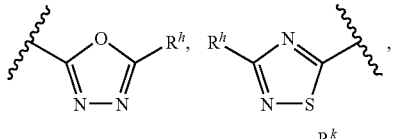

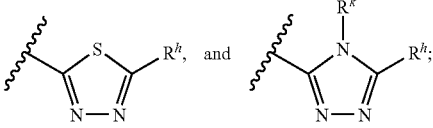

wherein $R^h$ and $R^i$ are each independently selected from: —H, —OH, —SH, —NH$_2$, C$_{1-3}$ alkyl —CF$_3$; and each $R^k$ is selected from: —H, and C$_{1-3}$ alkyl.

In another class of the present invention, each $R^{15}$ is independently selected from:

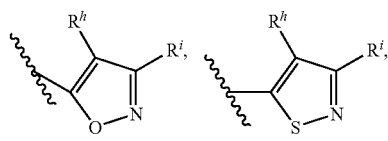

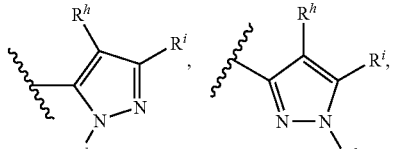

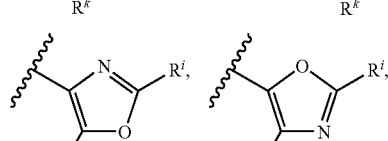

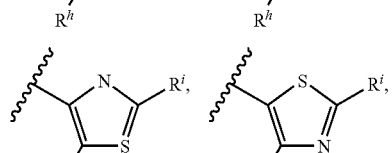

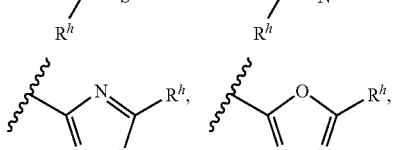

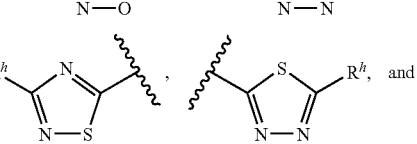

-continued

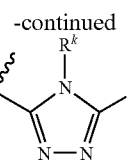

wherein $R^h$ and $R^i$ are each independently selected from: —H, —OH, —SH, —NH$_2$, methyl, and —CF$_3$; and each $R^k$ is selected from: —H, and methyl. In one subclass of the present invention, each $R^{15}$ is independently selected from:

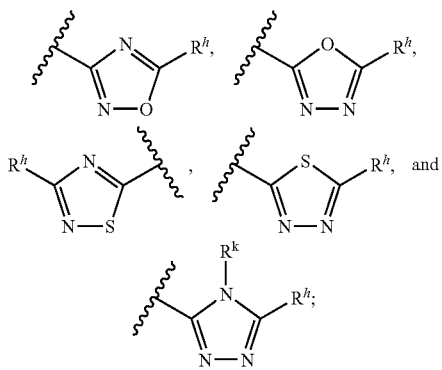

wherein $R^h$ is selected from: —H, —OH, and —NH$_2$, and each $R^k$ is selected from: —H, and methyl.

In one subclass of the present invention, each $R^{15}$ is independently selected from:

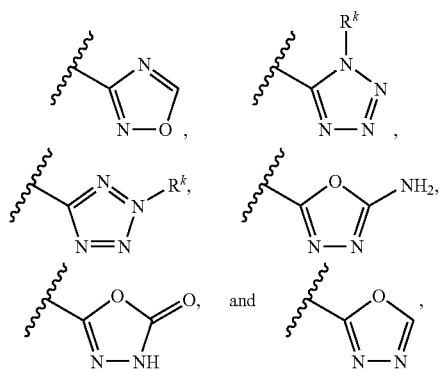

wherein $R^k$ is selected from hydrogen and methyl.

In yet another subclass of the present invention, $R^{15}$ is selected from:

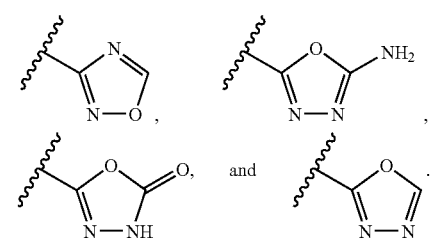

In one embodiment of the present invention, each $R^a$ is independently selected from:
(1) halogen,
(2) —N(R$^e$)(R$^f$),
(3) carboxy,
(4) C$_{1-4}$alkyl,
(5) C$_{1-4}$alkoxy,
(6) aryl,
(7) aryl C$_{1-4}$alkyl,
(8) hydroxy,
(9) CF$_3$,
(10) —OC(O)C$_{1-4}$alkyl, and
(11) aryloxy,
wherein alkyl may be straight chain or branched.

In one class of this embodiment, each $R^a$ is independently selected from:
(1) chloro,
(2) fluoro,
(3) NH$_2$,
(4) carboxy,
(5) methyl,
(6) ethyl,
(7) isopropyl,
(8) n-propyl,
(9) n-butyl,
(10) t-butyl,
(11) sec-butyl,
(12) methoxy,
(13) phenyl,
(14) benzyl,
(15) hydroxy,
(16) —CF$_3$,
(17) —OC(O)CH$_3$, and
(18) phenoxy.

In one subclass of this class, each $R^a$ is independently selected from:
(1) fluoro,
(2) chloro,
(3) methyl,
(4) methoxy,
(5) hydroxy, and
(6) —CF$_3$.

In another embodiment of the present invention, each $R^b$ is independently selected from:
(1) halogen,
(2) —OR$^{11}$,
(3) —CF$_3$,
(4) aryl,
(5) heteroaryl,
(6) cyano,
(7) C(O)R$^{11}$,
(8) —C(O)OR$^{11}$,
(9) —C(O)N(R$^e$)(R$^f$),
(10) —N(R$^{14}$)S(O)$_n$R$^{11}$,
(11) —NR$^{14}$C(O)R$^{11}$,
(12) —NR$^{14}$C(O)OR$^{11}$,
(13) —N(R$^e$)(R$^f$),
(14) —S(O)$_n$R$^{11}$,
(15) —S(O)$_2$OR$^{10}$,
(16) —OC(O)R$^{11}$,
(17) —OC(O)N(R$^e$)(R$^f$),
(18) —NO$_2$,
(19) C$_{3-7}$ cycloalkyl, and
(20) cycloheteroalkyl;
wherein cycloalkyl, cycloheteroalkyl, heteroaryl and aryl are optionally substituted with one to four substituents independently selected from R$^d$.

In one class of this embodiment, each $R^b$ is independently selected from:
(1) halogen,
(2) hydroxy,
(3) methyoxy,
(4) —$CF_3$,
(5) phenyl,
(6) cyano,
(7) —$C(O)CH_3$,
(8) —$C(O)OH$,
(9) —$C(O)OCH_3$,
(10) —$C(O)NH_2$,
(11) —$C(O)NH(CH_3)$,
(12) —$C(O)N(CH_3)_2$,
(13) —$NH_2$,
(14) —$S(O)_2CH_3$,
(15) —$S(O)_2H$,
(16) —$OC(O)R^{11}$;
(17) —$OC(O)N(CH_3)_2$,
(18) —$OC(O)NH—CH(CH_3)_2$,
(19) —$NO_2$,
(20) cyclopropyl, and
(21) cyclohexyl,
wherein cycloalkyl and phenyl are optionally substituted with one or two substituents independently selected from $R^d$.

In one subclass of this class, each $R^b$ is independently selected from:
(1) fluoro,
(2) chloro,
(3) hydroxy,
(4) methyoxy,
(5) —$CF_3$,
(6) phenyl,
(7) cyano,
(8) —$C(O)CH_3$,
(9) —$C(O)OH$,
(10) —$C(O)OCH_3$,
(11) —$C(O)NH_2$,
(12) —$C(O)NH(CH_3)$,
(13) —$C(O)N(CH_3)_2$,
(14) —$NH_2$,
(15) —$S(O)_2CH_3$,
(16) —$OC(O)N(CH_3)_2$, and
(17) —$OC(O)NH—CH(CH_3)_2$,
wherein phenyl is optionally substituted with one or two substituents independently selected from the group selected from $R^d$.

In another subclass of this class, each $R^b$ is independently selected from:
(1) fluoro,
(2) chloro,
(3) hydroxy,
(4) methyoxy,
(5) —$CF_3$,
(6) cyano,
(7) —$C(O)CH_3$,
(8) —$C(O)OH$,
(9) —$C(O)OCH_3$,
(10) —$C(O)NH_2$,
(11) —$C(O)NH(CH_3)$, and
(12) —$C(O)N(CH_3)_2$.

In one embodiment of the present invention, each $R^c$ is independently selected from:
(1) halogen,
(2) —$OR^{11}$,
(3) —$CF_3$,
(4) aryl,
(5) heteroaryl,
(6) cyano,
(7) —$C(O)R^{11}$,
(8) —$C(O)OR^{11}$,
(9) —$C(O)N(R^{12})(R^{13})$,
(10) —$N(R^{14})S(O)_nR^{11}$,
(11) —$NR^{14}C(O)R^{11}$,
(12) —$NR^{14}C(O)OR^{11}$,
(13) —$N(R^{12})(R^{13})$,
(14) —$S(O)_nR^{11}$,
(15) —$S(O)_2OR^{11}$,
(16) —$OC(O)R^{11}$,
(17) —$OC(O)N(R^{12})(R^{13})$,
(18) —$NO_2$,
(19) $C_{3-7}$ cycloalkyl,
(20) cycloheteroalkyl,
(21) $C_{1-6}$ alkyl,
(22) $C_{2-6}$ alkenyl,
(23) $C_{2-6}$ alkynyl, and
(24) aryl-$C_{1-6}$ alkyl;
wherein alkyl, alkenyl, alkynyl are straight chain or branched; alkyl, alkenyl, alkynyl, cycloalkyl, cycloheteroalkyl and aryl are optionally substituted with one to four substituents independently selected from $R^d$.

In one class of this embodiment, each $R^c$ is independently selected from:
(1) halogen,
(2) —OH,
(3) —$OCH_3$,
(4) —$CF_3$,
(5) phenyl,
(6) pyridyl,
(7) cyano,
(8) —$C(O)CH_3$,
(9) —$C(O)OR^{11}$,
(10) —$C(O)NH_2$,
(11) —$N(H)S(O)_2R^{11}$,
(12) —$NHC(O)R^{11}$,
(13) —$NHC(O)OR^{11}$,
(14) —$N(CH_3)_2$,
(15) —$NH_2$,
(16) —$S(O)_2R^{11}$,
(17) —$OC(O)CH_3$,
(18) —$OC(O)N(CH_3)_2$,
(19) —$OC(O)NH—CH(CH_3)_2$,
(20) —$NO_2$,
(21) cyclopropyl,
(22) methyl,
(23) $C_{2-6}$ alkenyl, and
(24) benzyl;
wherein alkyl, alkenyl, alkynyl are straight chain or branched; alkyl, alkenyl, alkynyl, cycloalkyl, cycloheteroalkyl and aryl are optionally substituted with one or two substituents independently selected from $R^d$.

In one subclass of this class, each $R^c$ is independently selected from:
(1) halogen,
(2) —OH,
(3) —$OCH_3$,
(4) —$CF_3$,
(5) cyano, and
(6) —$S(O)_2R^{11}$.

In another class of this embodiment, each $R^c$ is independently selected from:
(1) halogen,
(2) —OH,
(3) —$OCH_3$, (4) —CF$_3$,
(5) phenyl,
(6) pyridyl,
(7) triazolyl,
(8) azetidinyl,
(9) imidazolyl,
(10) thienyl,
(11) cyano,
(12) —C(O)CH$_3$,
(13) —C(O)OR$^{10}$,
(14) —C(O)NH$_2$,
(15) —NHS(O)$_2$R$^{11}$,
(16) —NHC(O)R$^{10}$,
(17) —NHC(O)OR$^{11}$,
(18) —N(CH$_3$)$_2$,
(19) NH$_2$,
(20) SR$^{11}$,
(21) —S(O)$_2$R$^{11}$,
(22) —OC(O)CH$_3$,
(23) —OC(O)N(CH$_3$)$_2$,
(24) —OC(O)NH—CH(CH$_3$)$_2$,
(25) —NO$_2$,
(26) cyclopropyl,
(27) methyl,
(28) C$_{2-6}$ alkenyl, and
(29) benzyl;
wherein alkyl, alkenyl, are straight chain or branched; alkyl, alkenyl, cycloalkyl, cycloheteroalkyl aryl, and heteroaryl are optionally substituted with one or two substituents independently selected from R$^d$.

In a subclass of this class, each R$^c$ is independently selected from:
(1) halogen,
(2) —H,
(3) OCH$_3$,
(4) —CF$_3$,
(5) cyano,
(6) —S(O)$_2$R$^{11}$,
(7) triazolyl
(8) azetidinyl,
(9) imidazolyl,
(10) —SCH$_3$,
(11) —SCH$_2$CH$_3$,
(12) —SCH(CH$_3$)$_2$, and
(13) —NH$_2$.

In one embodiment of the present invention, each R$^d$ is independently selected from:
(1) halogen,
(2) —NR$^{12}$R$^{13}$
(3) C$_{1-4}$alkyl,
(4) C$_{1-4}$alkoxy,
(5) aryl,
(6) aryl C$_{1-4}$alkyl,
(7) hydroxy,
(8) —CF$_3$,
(9) —OCF$_3$,
(10) —C(O)R$^{11}$,
(11) —CO$_2$R$^{11}$,
(12) —C(O)NR$^{12}$R$^{13}$,
(13) —OC(O)C$_{1-4}$alkyl,
(14) —NR$^{14}$C(O)R$^{11}$,
(15) —OC(O)NR$^{12}$R$^{13}$,
(16) —NR$^{14}$C(O)OR$^{11}$,
(17) —NR$^{14}$C(O)NR$^{12}$R$^{13}$,
(18) —OC(O)NR$^{12}$R$^{13}$, and
(19) aryloxy,
wherein alkyl is straight chain or branched.

In one class of this embodiment of the present invention, each R$^d$ is independently selected from:
(1) halogen,
(2) —NH$_2$,
(3) methyl,
(4) methoxy,
(5) phenyl,
(6) benzyl,
(7) hydroxy,
(8) —CF$_3$,
(9) —OCF$_3$,
(10) —C(O)CH$_3$,
(11) —CO$_2$H,
(12) —CO$_2$CH$_3$,
(13) —C(O)NH$_2$,
(14) —OC(O)CH$_3$,
(15) —NHC(O)CH$_3$,
(16) —OC(O)N(CH$_3$)$_2$,
(17) —NHC(O)OCH$_3$,
(18) —NHC(O)N(CH$_3$)$_2$,
(19) —OC(O)N(CH$_3$)$_2$, and
(20) phenyloxy.

In one subclass of this class of the present invention, each R$^d$ is independently selected from:
(1) halogen,
(2) methyl,
(3) methoxy,
(4) hydroxy,
(5) —CF$_3$, and
(6) —OCF$_3$.

In one embodiment of the present invention, R$^e$ and R$^f$ are each independently selected from:
(1) hydrogen,
(2) C$_{1-8}$ alkyl, straight chain or branched, unsubstituted or substituted with one to three substituents selected from halogen, hydroxyl, and C$_{1-6}$alkyloxy-,
(3) C$_{2-8}$ alkenyl, straight chain or branched,
(4) perfluoro C$_{1-6}$ alkyl, straight chain or branched,
(5) C$_{1-8}$ alkylcarbonyl-, straight chain or branched, unsubstituted or substituted on a carbon atom with one to three substituents selected from halogen, hydroxyl, and C$_{1-6}$alkyloxy-,
(6) C$_{1-8}$ alkylcarbonyloxy-, straight chain or branched, unsubstituted or substituted on a carbon atom with one to three substituents selected from halogen, hydroxyl, and C$_{1-6}$alkyloxy-,
(7) C$_{3-7}$cycloalkyl,
(8) cycloalkyl-C$_{1-6}$alkyl, wherein alkyl is straight chain or branched,
(9) cycloheteroalkyl,
(10) aryl, unsubstituted or substituted with one to three substituents selected from halogen, amino, carboxy, methyl, methoxy, hydroxy, trifluoromethyl, and methylcarbonyloxy,
(11) arylcarbonyl-, unsubstituted or substituted on a carbon atom with one to three substituents selected from halogen, amino, carboxy, methyl, methoxy, hydroxy, trifluoromethyl, and methylcarbonyloxy,
(12) arylcarbonyloxy-, unsubstituted or substituted on a carbon atom with one to three substituents selected from halogen, amino, carboxy, methyl, methoxy, hydroxy, trifluoromethyl, and methylcarbonyloxy,
(13) heteroaryl, unsubstituted or substituted on a carbon or nitrogen atom with one to three substituents selected from halogen, amino, carboxy, methyl, methoxy, hydroxy, trifluoromethyl, and methylcarbonyloxy,

(14) aryl $C_{1-6}$alkyl, wherein alkyl is straight chain or branched, and
(15) heteroaryl $C_{1-6}$alkyl, wherein alkyl is straight chain or branched, or $R^e$ and $R^f$ together with the atom(s) to which they are attached form a heterocyclic ring of 4 to 7 members containing 0-2 additional heteroatoms independently selected from oxygen, sulfur and N—$R^{14}$.

In one embodiment of the present invention, $R^e$ and $R^f$ together with the atom(s) to which they are attached form a heterocyclic ring of 4 to 7 members containing 0-2 additional heteroatoms independently selected from oxygen, sulfur and N—$R^{14}$.

In one class of this embodiment, $R^e$ and $R^f$ together with the atom(s) to which they are attached form a heterocyclic ring of 5 to 6 members.

In another embodiment of the present invention, $R^e$ and $R^f$ are each independently selected from:
 (1) hydrogen,
 (2) $C_{1-8}$ alkyl, straight chain or branched, unsubstituted or substituted with one to three substituents selected from halogen, hydroxyl, and $C_{1-6}$alkyloxy-,
 (3) $C_{2-8}$ alkenyl, straight chain or branched,
 (4) perfluoro $C_{1-6}$ alkyl, straight chain or branched,
 (5) $C_{1-8}$ alkylcarbonyl-, straight chain or branched, unsubstituted or substituted on a carbon atom with one to three substituents selected from halogen, hydroxyl, and $C_{1-6}$alkyloxy-,
 (6) $C_{1-8}$ alkylcarbonyloxy-, straight chain or branched, unsubstituted or substituted on a carbon atom with one to three substituents selected from halogen, hydroxyl, and $C_{1-6}$alkyloxy-,
 (7) $C_{3-7}$cycloalkyl,
 (8) cycloalkyl-$C_{1-6}$alkyl, wherein alkyl is straight chain or branched,
 (9) cycloheteroalkyl,
 (10) aryl, unsubstituted or substituted with one to three substituents selected from halogen, amino, carboxy, methyl, methoxy, hydroxy, trifluoromethyl, and methylcarbonyloxy,
 (11) arylcarbonyl-, unsubstituted or substituted on a carbon atom with one to three substituents selected from halogen, amino, carboxy, methyl, methoxy, hydroxy, trifluoromethyl, and methylcarbonyloxy,
 (12) arylcarbonyloxy-, unsubstituted or substituted on a carbon atom with one to three substituents selected from halogen, amino, carboxy, methyl, methoxy, hydroxy, trifluoromethyl, and methylcarbonyloxy,
 (13) heteroaryl, unsubstituted or substituted on a carbon or nitrogen atom with one to three substituents selected from halogen, amino, carboxy, methyl, methoxy, hydroxy, trifluoromethyl, and methylcarbonyloxy,
 (14) aryl $C_{1-6}$alkyl, wherein alkyl is straight chain or branched, and
 (15) heteroaryl $C_{1-6}$alkyl, wherein alkyl is straight chain or branched.

In one class of this embodiment, $R^e$ and $R^f$ are each independently selected from:
 (1) hydrogen
 (2) $C_{1-4}$ alkyl, straight chain or branched, unsubstituted or substituted with one to three substituents selected from halogen, hydroxyl, and methoxy,
 (3) allyl,
 (4) trifluoromethyl,
 (5) $C_{1-4}$ alkylcarbonyl-, straight chain or branched, unsubstituted or substituted on a carbon atom with one to three substituents selected from halogen, hydroxyl, and methoxy,
 (6) methylcarbonyloxy-,
 (7) cyclopropyl,
 (8) cyclohexyl,
 (9) phenyl, unsubstituted or substituted with one to three substituents selected from halogen, amino, carboxy, methyl, methoxy, hydroxy, trifluoromethyl, and methylcarbonyloxy,
 (10) phenylcarbonyl-, unsubstituted or substituted on a carbon atom with one to three substituents selected from halogen, amino, carboxy, methyl, methoxy, hydroxy, trifluoromethyl, and methylcarbonyloxy,
 (11) arylcarbonyloxy-, unsubstituted or substituted on a carbon atom with one to three substituents selected from halogen, amino, carboxy, methyl, methoxy, hydroxy, trifluoromethyl, and methylcarbonyloxy,
 (12) pyridyl, unsubstituted or substituted on a carbon or nitrogen atom with one to three substituents selected from halogen, amino, carboxy, methyl, methoxy, hydroxy, trifluoromethyl, and methylcarbonyloxy, and
 (13) benzyl.

In one class of this embodiment, $R^e$ and $R^f$ are each independently selected from:
 (1) hydrogen
 (2) methyl,
 (3) allyl, and
 (4) trifluoromethyl.

In one embodiment of the present invention, each $R^g$ is independently selected from:
 (4) hydrogen,
 (5) halogen,
 (6) —$OR^{11}$,
 (7) —$CF_3$,
 (8) aryl,
 (9) heteroaryl,
 (10) cyano,
 (11) —$C(O)R^{11}$,
 (12) —$C(O)OR^{11}$,
 (13) —$C(O)N(R^{12})(R^{13})$,
 (14) —$N(R^{14})S(O)nR^{11}$,
 (15) —$NR^{14}C(O)R^{11}$,
 (16) —$NR^{14}C(O)OR^{11}$,
 (17) —$N(R^{12})(R^{13})$,
 (18) —$S(O)nR^{11}$,
 (19) —$S(O)_2OR^{11}$,
 (20) —$OC(O)R^{11}$,
 (21) —$OC(O)N(R^{12})(R^{13})$,
 (22) —$NO_2$,
 (23) $C_{3-7}$ cycloalkyl,
 (24) Cycloheteroalkyl,
 (25) $C_{1-6}$ alkyl,
 (26) $C_{2-6}$ alkenyl,
 (27) $C_{2-6}$ alkynyl, and
 (28) aryl-$C_{1-6}$ alkyl;
 wherein alkyl, alkenyl, alkynyl are straight chain or branched; alkyl, alkenyl, alkynyl, cycloalkyl, cycloheteroalkyl and aryl are optionally substituted with one to four substituents selected from a group independently selected from $R^d$.

In one class of this embodiment, each $R^9$ is independently selected from:
 (1) hydrogen,
 (2) halogen,
 (3) —OH, (4) —OCH$_3$,
(5) —CF$_3$,
(6) phenyl,
(7) pyridyl,
(8) cyano,
(9) —C(O)CH$_3$,
(10) —C(O)OR$^{11}$,
(11) —C(O)NH$_2$,
(12) —N(H)S(O)$_2$R$^{11}$,
(13) —NHC(O)R$^{11}$,
(14) —NHC(O)OR$^{11}$,
(15) —N(CH$_3$)$_2$,
(16) NH$_2$,
(17) —S(O)$_2$R$^{11}$,
(18) —OC(O)CH$_3$,
(19) —OC(O)N(CH$_3$)$_2$,
(20) —OC(O)NH—CH(CH$_3$)$_2$,
(21) —NO$_2$,
(22) cyclopropyl,
(23) methyl,
(24) C$_{2-6}$ alkenyl, and
(25) benzyl;
wherein alkyl, alkenyl, alkynyl are straight chain or branched; alkyl, alkenyl, alkynyl, cycloalkyl, cycloheteroalkyl and aryl are optionally substituted with one or two substituents independently selected from R$^d$.

In one subclass of this class, each R$^g$ is independently selected from:
(1) hydrogen,
(2) halogen,
(3) —OH,
(4) —OCH$_3$,
(5) —CF$_3$,
(6) cyano, and
(7) —S(O)$_2$R$^{11}$.

In another class of this embodiment, each R$^g$ is independently selected from:
(1) hydrogen,
(2) halogen,
(3) —OH,
(4) —OCH$_3$,
(5) —CF$_3$,
(6) phenyl,
(7) pyridyl,
(8) triazolyl,
(9) azetidinyl,
(10) imidazolyl,
(11) thienyl,
(12) cyano,
(13) —C(O)CH$_3$,
(14) —C(O)OR$^{110}$,
(15) —C(O)NH$_2$,
(16) —NHS(O)$_2$R$^{11}$,
(17) —NHC(O)R$^{10}$,
(18) —NHC(O)OR$^{11}$,
(19) —N(CH$_3$)$_2$,
(20) NH$_2$,
(21) SR$^{11}$,
(22) —S(O)$_2$R$^{11}$,
(23) —OC(O)CH$_3$,
(24) —OC(O)N(CH$_3$)$_2$,
(25) —OC(O)NH—CH(CH$_3$)$_2$,
(26) —NO$_2$,
(27) cyclopropyl,
(28) methyl,
(29) C$_{2-6}$ alkenyl, and
(30) benzyl;

wherein alkyl, alkenyl, are straight chain or branched; alkyl, alkenyl, cycloalkyl, cycloheteroalkyl, aryl, and heteroaryl are optionally substituted with one or two substituents independently selected from R$^d$.

In a subclass of this class, each R$^g$ is independently selected from:
(1) hydrogen,
(2) fluoro,
(3) chloro, and
(4) cyano.

In a yet another subclass of this class, each R$^g$ is independently selected from:
(1) hydrogen, and
(2) fluoro.

In one embodiment of the present invention, each R$^h$ is independently selected from:
(1) —H,
(2) —OH,
(3) —SH,
(4) —NH$_2$,
(5) C$_{1-3}$ alkyl, and
(6) —CF$_3$.

In one class of this embodiment, each R$^h$ is independently selected from:
(1) —H,
(2) —OH,
(3) —SH,
(4) —NH$_2$,
(5) methyl, and
(6) —CF$_3$.

In one subclass of this class, each R$^h$ is independently selected from:
(1) —H,
(2) —OH, and
(3) —NH$_2$.

In one embodiment of the present invention, each R$^i$ is independently selected from:
(1) —H,
(2) —OH,
(3) —SH,
(4) —NH$_2$,
(5) C$_{1-3}$ alkyl, and
(6) —CF$_3$.

In one class of this embodiment, each R$^i$ is independently selected from:
(1) —H,
(2) —OH,
(3) —SH,
(4) —NH$_2$,
(5) methyl, and
(6) —CF$_3$.

In one subclass of this class, each R$^i$ is independently selected from:
(1) —H,
(2) —OH, and
(3) —NH$_2$.

In another subclass of this class, each R$^i$ is hydrogen.

In one embodiment, each R$^k$ is independently selected from:
(1) —H, and
(2) C$_{1-3}$ alkyl.

In one class, each R$^k$ is independently selected from:
(1) —H, and
(2) methyl.

In one embodiment of the present invention, when X is hydroxy, —NR$^{14}$C(O)R$^{11}$, —NR$^{14}$C(O)OR$^{11}$, —N(R$^{12}$)(R$^{13}$), or OR$^{11}$, then R$^2$ and R$^3$ are not:

(1) both hydrogen, nor
(2) form a carbonyl group together with the carbon to which they are attached.

In another embodiment of the present invention, when X' is hydroxy, —C(O)N($R^{12}$)$R^{13}$), —$NR^{14}$C(O)$R^{11}$, —$NR^{14}$C(O)$OR^{11}$, —N($R^{12}$)($R^{13}$), or —$OR^{11}$, then $R^2$ and $R^3$ are not:

(1) both hydrogen, nor
(2) form a carbonyl group together with the carbon to which they are attached.

In another embodiment of the present invention are compounds of structural formula IA:

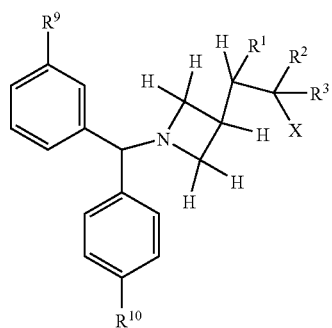

IA

In a class of this embodiment are compounds of structural formula IB:

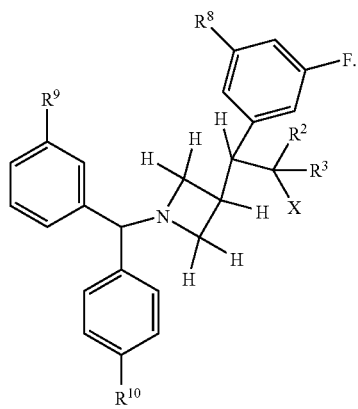

IB

In one class of this embodiment are compounds of structural formula IC:

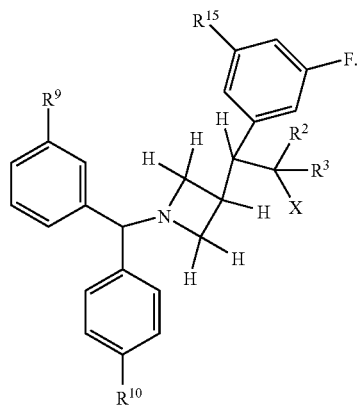

IC

In another class are compounds of structural formula ID:

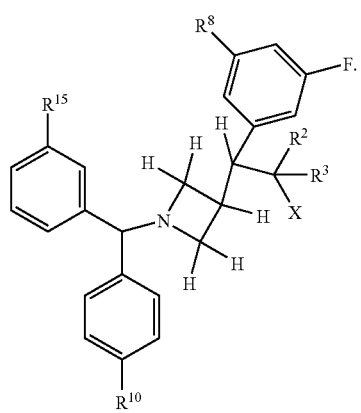

ID

In still another class are compounds of structural formula IE:

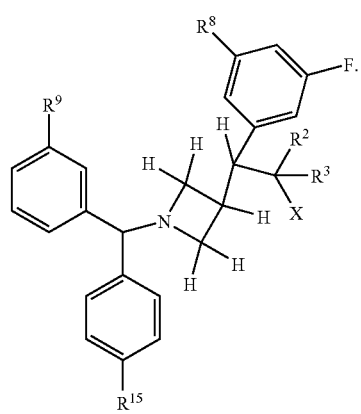

IE

In yet another class are compounds of structural formula IF:

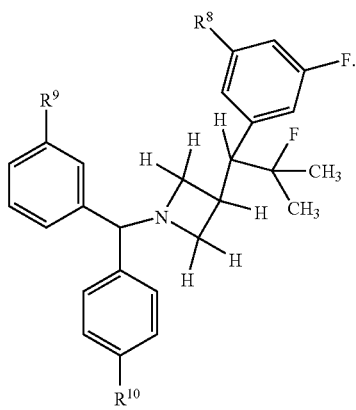

IF

In one embodiment of the present invention, only one of $R^8$, $R^9$, and $R^{10}$ is $R^{15}$.

In one class, only $R^8$ is $R^{15}$.
In another class, only $R^9$ is $R^{15}$.
In still another class, only $R^{10}$ is $R^{15}$.

"Alkyl", as well as other groups having the prefix "alk", such as alkoxy, alkanoyl, means carbon chains which may be linear or branched or combinations thereof. Examples of alkyl groups include methyl, ethyl, n-propyl, isopropyl, butyl, isobutyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-l-pentynyl, 2-heptynyl and the like.

"Cycloalkyl" means mono- or bicyclic or bridged saturated carbocyclic rings, each having from 3 to 10 carbon atoms. Examples of cycloalkyl include cyclopropyl, cyclobutyl, cyclopentyl, cyclohexyl, cycloheptyl, cyclooxtyl, tetrahydronaphthyl, decahydronaphthyl, and the like.

"Aryl" means mono- or bicyclic aromatic rings containing only carbon atoms. Examples of aryl include phenyl, naphthyl, and the like.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, benzothiazolyl, furo(2,3-b)pyridyl, quinolyl, indolyl, isoquinolyl, oxazolidinyl, and the like. The heteroaryl ring may be substituted on one or more carbon atoms. In one embodiment of the present invention, heteroaryl is pyridinyl, imidazolyl, and thienyl.

"Cycloheteroalkyl" means mono- or bicyclic or bridged saturated rings containing at least one heteroatom selected from N, S and O, each of said ring having from 3 to 10 atoms in which the point of attachment may be carbon or nitrogen. Examples of "cycloheteroalkyl" include pyrrolidinyl, piperidinyl, piperazinyl, imidazolidinyl, pyranyl, tetrahydrofuranyl, morpholinyl, dioxanyl, oxanyl, azetidinyl, perhydroazepinyl, tetrahydrofuranyl, 1-thia-4-aza-cyclohexane (thiomorpholinyl), hexahydrothieno-pyridinyl, thienopyridinyl, azacycloheptyl, and the like. The term also includes partially unsaturated monocyclic rings that are not aromatic, such as 2- or 4-pyridones attached through the nitrogen or N-substituted-(1H, 3H)-pyrimidine-2,4-diones (N-substituted uracils). The cycloheteroalkyl ring may be substituted on the ring carbons and/or the ring nitrogens.

"Halogen" includes fluorine, chlorine, bromine and iodine.

When any variable (e.g., $R^1$, $R^d$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to:

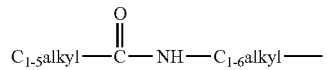

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations.

It will be understood that, as used herein, references to the compounds of Formula I are meant to also include the pharmaceutically acceptable salts.

Compounds of the present invention are modulators of the CB1 receptor. In particular, the compounds of structural formula I are antagonists or inverse agonists of the CB1 receptor.

An "agonist" is a compound (hormone, neurotransmitter or synthetic compound) which binds to a receptor and mimics the effects of the endogenous regulatory compound, such as contraction, relaxation, secretion, change in enzyme activity, etc. An "antagonist" is a compound, devoid of intrinsic regulatory activity, which produces effects by interfering with the binding of the endogenous agonist or inhibiting the action of an agonist. An "inverse agonist" is a compound which acts on a receptor but produces the opposite effect produced by the agonist of the particular receptor.

Compounds of this invention are modulators of the CB1 receptor and as such are useful as centrally acting drugs in the treatment of psychosis, memory deficits, cognitive disorders, Alzheimer's disease, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. In particular, the compounds of this invention are antagonists/inverse agonists of the CB1 receptor. The compounds are also useful for the treatment of substance abuse disorders, particularly to opiates, alcohol, marijuana, and nicotine. In particular, the compounds of the invention are useful for smoking cessation. The compounds are also useful for the treatment of obesity or eating disorders associated with excessive food intake and complications associated therewith, including left ventricular hypertrophy, as well as treating or preventing obesity in other mammalian species, including canines and felines. The compounds are also useful for the treatment of constipation and chronic intestinal pseudo-obstruction. The compounds are also useful for the treatment of cirrhosis of the liver, non-alcoholic fatty liver disease (NAFLD), non-alcoholic steatohepatitis (NASH), and asthma.

The compounds of the present invention possess a 5-membered, carbon-linked, partly or fully unsaturated, heterocylic moiety and are metabolized by both oxidative and nonoxidative mechanisms. This heterocyclic moiety is amenable to secondary metabolic processing and/or oxidative cleavage, which provides a favorable metabolic profile. The compounds of the present invention exhibit mixed mechanisms of metabolism or clearance. It is highly desirable that the clearance and/or excretion of drugs from targeted patients be mediated by more than one mechanism rather than be dependent upon a single mechanism to clear the drug from the patient. This is a desirable feature to avoid potential drug-drug interactions or genetic polymorphisms in a single clearance mechanism that might contribute to broad patient to patient variability. Likewise, mixed mechanisms of clearance may avoid undesirable rises in drug exposure in patients with compromised organ function; for example, liver function impairment or kidney disease. With multiple metabolic pathways available for clearance and/or excretion, compounds of the present invention may have more limited patient to patient variability in exposure and a greater safety profile.

The terms "administration of" and or "administering a" compound should be understood to mean providing a compound of the invention or a prodrug of a compound of the invention to the individual in need of treatment.

The administration of the compound of structural formula I in order to practice the present methods of therapy is carried out by administering an effective amount of the compound of structural formula I to the mammalian patient in need of such treatment or prophylaxis. The need for a prophylactic administration according to the methods of the present invention is determined via the use of well known risk factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature. The following are examples of such animal disease models: a) suppression of food intake and resultant weight loss in rats (Life Sciences 1998, 63, 113-117); b) reduction of sweet food intake in marmosets (Behavioural Pharm. 1998, 9, 179-181); c) reduction of sucrose and ethanol intake in mice (Psychopharm. 1997, 132, 104-106); d) increased motor activity and place conditioning in rats (Psychopharm. 1998, 135, 324-332; Psychopharmacol 2000, 151: 25-30); e) spontaneous locomotor activity in mice (J. Pharm. Exp. Ther. 1996, 277, 586-594); f) reduction in opiate self-administration in mice (Sci. 1999, 283, 401-404); g) bronchial hyperresponsiveness in sheep and guinea pigs as models for the various phases of asthma (for example, see W. M. Abraham et al., "$\alpha_4$-Integrins mediate antigen-induced late bronchial responses and prolonged airway hyperresponsiveness in sheep." J. Clin. Invest. 93, 776 (1993) and A. A. Y. Milne and P. P. Piper, "Role of VLA-4 integrin in leucocyte recruitment and bronchial hyperresponsiveness in the guinea-pig." Eur. J. Pharmacol., 282, 243 (1995)); h) mediation of the vasodilated state in advanced liver cirrhosis induced by carbon tetrachloride (Nature Medicine, 2001, 7 (7), 827-832); i) amitriptyline-induced constipation in cynomolgus monkeys is beneficial for the evaluation of laxatives (Biol. Pharm. Bulletin (Japan), 2000, 23(5), 657-9); j) neuropathology of paediatric chronic intestinal pseudo-obstruction and animal models related to the neuropathology of paediatric chronic intestinal pseudo-obstruction (Journal of Pathology (England), 2001, 194 (3), 277-88).

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 100 mg in one embodiment from about 0.01 mg to about 50 mg, and in another embodiment from 0.1 mg to 10 mg of a compound of Formula I per kg of body weight per day.

In the case where an oral composition is employed, a suitable dosage range is, e.g. from about 0.01 mg to about 1000 mg of a compound of Formula I per day. In one embodiment, the range is from about 0.1 mg to about 10 mg per day. For oral administration, the compositions are preferably provided in the form of tablets containing from 0.01 to 1,000 mg, preferably 0.01, 0.05, 0.1, 0.5, 1, 2, 2.5, 3, 4, 5, 6, 7, 8, 9, 10, 12, 12.5, 15, 20, 25, 30, 40, 50, 100, 250, 500, 750 or 1000 milligrams of the active ingredient for the symptomatic adjustment of the dosage to the patient to be treated.

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, particularly a human or companion animal such as a dog or cat, with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. By "pharmaceutically acceptable" it is meant the carrier, diluent or excipient must be compatible with the other ingredients of the formulation and not deleterious to the recipient thereof. The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers, or as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, solutions, ointments, gels, lotions, dusting powders, and the like. The topical pharmaceutical compositions containing the compounds of the present invention ordinarily include about 0.005% to 5% by weight of the active compound in admixture with a pharmaceutically acceptable vehicle. Transdermal skin patches useful for administering the compounds of the present invention include those well known to those of ordinary skill in that art. In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules (including timed release and sustained release formulations), pills, cachets, powders, granules or tablets each containing a predetermined amount of the active ingredient, as a powder or granules or as a solution or a suspension in an aqueous liquid, a non-aqueous liquid, an oil-in-water emulsion or a water-in-oil liquid emulsion, including elixirs, tinctures, solutions, suspensions, syrups and emulsions. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet cachet or capsule contains from about 0.01 to 1,000 mg, particularly 0.01, 0.05, 0.1, 0.5, 1.0, 2, 2.5, 3, 4, 5, 6, 7, 8, 9, 10, 12, 15, 25, 30, 40, 50, 75, 100, 125, 150, 175, 180, 200, 225, 250, 500, 750 and 1,000 milligrams of the active ingredient for the symptomatic adjustment of the dosage to the patient to be treated.

Additional suitable means of administration of the compounds of the present invention include injection, intravenous bolus or infusion, intraperitoneal, subcutaneous, intramuscular and topical, with or without occlusion.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

The dose may be administered in a single daily dose or the total daily dosage may be administered in divided doses of two, three or four times daily. Furthermore, based on the properties of the individual compound selected for administration, the dose may be administered less frequently, e.g., weekly, twice weekly, monthly, etc. The unit dosage will, of course, be correspondingly larger for the less frequent administration.

When administered via intranasal routes, transdermal routes, by rectal or vaginal suppositories, or through a continual intravenous solution, the dosage administration will, of course, be continuous rather than intermittent throughout the dosage regimen.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Capsule | mg/capsule |
|---|---|
| Compound of Formula I | 25 |
| Lactose Powder | 573.5 |
| Magnesium Stearate | 1.5 |
| | 600 |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Aerosol | Per canister |
|---|---|
| Compound of Formula I | 24 mg |
| Lecithin, NF Liq. Conc. | 1.2 mg |
| Trichlorofluoromethane, NF | 4.025 g |
| Dichlorodifluoromethane, NF | 12.15 g |

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I include, but are not limited to: antipsychotic agents, cognition enhancing agents, anti-migraine agents, anti-asthmatic agents, antiinflammatory agents, anxiolytics, anti-Parkinson's agents, anti-epileptics, anorectic agents, serotonin reuptake inhibitors, other anti-obesity agents, as well as antidiabetic agents, lipid lowering agents, and antihypertensive agents which may be administered separately or in the same pharmaceutical compositions.

The present invention also provides a method for the treatment or prevention of a CB1 receptor modulator mediated disease, which method comprises administration to a patient in need of such treatment or at risk of developing a CB1 receptor modulator mediated disease of an amount of a CB1 receptor modulator and an amount of one or more active ingredients, such that together they give effective relief.

In a further aspect of the present invention, there is provided a pharmaceutical composition comprising a CB1 receptor modulator and one or more active ingredients, together with at least one pharmaceutically acceptable carrier or excipient.

Thus, according to a further aspect of the present invention there is provided the use of a CB1 receptor modulator and one or more active ingredients for the manufacture of a medicament for the treatment or prevention of a CB1 receptor modulator mediated disease. In a further or alternative aspect of the present invention, there is therefore provided a product comprising a CB1 receptor modulator and one or more active ingredients as a combined preparation for simultaneous, separate or sequential use in the treatment or prevention of CB1 receptor modulator mediated disease. Such a combined preparation may be, for example, in the form of a twin pack.

It will be appreciated that for the treatment or prevention of eating disorders, including obesity, bulimia nervosa and compulsive eating disorders, a compound of the present invention may be used in conjunction with other anorectic agents.

The present invention also provides a method for the treatment or prevention of eating disorders, which method comprises administration to a patient in need of such treatment an amount of a compound of the present invention and an amount of an anorectic agent, such that together they give effective relief.

Suitable anorectic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof. A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof. Particular halogenated amphetamine derivatives of use in combination with a compound of the present invention include: fenfluramine and dexfenfluramine, and pharmaceutically acceptable salts thereof.

The present invention also provides a method for the treatment or prevention of obesity, which method comprises administration to a patient in need of such treatment an amount of a compound of the present invention and an amount of another agent useful in treating obesity and obesity-related conditions, such that together they give effective relief. Suitable agents of use in combination with a compound of the present invention, include, but are not limited to:

(a) anti-diabetic agents such as (1) PPARγ agonists such as glitazones (e.g. ciglitazone; darglitazone; englitazone; isaglitazone (MCC-555); pioglitazone (ACTOS); rosiglitazone (AVANDIA); troglitazone; rivoglitazone, BRL49653; CLX-0921; 5-BTZD, GW-0207, LG-100641, R483, and LY-300512, and the like and compounds disclosed in WO97/10813, 97/27857, 97/28115, 97/28137, 97/27847, 03/000685, and 03/027112 and SPPARMS (selective PPAR gamma modulators) such as T131 (Amgen), FK614 (Fujisawa), netoglitazone, and metaglidasen; (2) biguanides such as buformin; metformin; and phenformin, and the like; (3) protein tyrosine phosphatase-1B (PTP-1B) inhibitors such as ISIS 113715, A-401674, A-364504, IDD-3, IDD 2846, KP-40046, KR61639, MC52445, MC52453, C7, OC-060062, OC-86839, OC29796, TTP-277BC1, and those agents disclosed in WO 04/041799, 04/050646, 02/26707, 02/26743, 04/092146, 03/048140, 04/089918, 03/002569, 04/065387, 04/127570, and US 2004/167183; (4) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (5) meglitinides such as repaglinide, metiglinide (GLUFAST) and nateglinide, and the like; (6) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR 14, and the like; (7) alpha-amylase inhibitors such as tendamistat, trestatin, and A1-3688, and the like; (8) insulin secreatagogues such as linogliride nateglinide, mitiglinide (GLUFAST), ID1101 A-4166, and the like; (9) fatty acid oxidation inhibitors, such as clomoxir, and etomoxir, and the like; (10) A2 antagonists, such as midaglizole; isaglidole; deriglidole; idazoxan; earoxan; and fluparoxan, and the like; (11) insulin or insulin mimetics, such as biota, LP-100, novarapid, insulin detemir, insulin lispro, insulin glargine, insulin zinc suspension (lente and ultralente); Lys-Pro insulin, GLP-1 (17-36), GLP-1 (73-7) (insulintropin); GLP-1 (7-36)-NH$_2$) exenatide/Exendin-4, Exenatide LAR, Linaglutide, AVE0010, CJC 1131, BIM51077, CS 872, THO318, BAY-694326, GP010, ALBUGON (GLP-1 fused to albumin), HGX-007 (Epac agonist), S-23521, and compounds disclosed in WO 04/022004, WO 04/37859, and the like; (12) non-thiazolidinediones such as JT-501, and farglitazar (GW-2570/GI-262579), and the like; (13) PPARα/γ dual agonists such as AVE 0847, CLX-0940, GW-1536, GW1929, GW-2433, KRP-297, L-796449, LBM 642, LR-90, LY510919, MK-0767, ONO 5129, SB 219994, TAK-559, TAK-654, 677954 (GlaxoSmithkline), E-3030 (Eisai), LY510929 (Lilly), AK109 (Asahi), DRF2655 (Dr. Reddy), DRF8351 (Dr. Reddy), MC3002 (Maxocore), TY51501 (ToaEiyo), naveglitazar, muraglitizar, peliglitazar, tesaglitazar (GALIDA), reglitazar (JTT-501), chiglitazar, and those disclosed in WO 99/16758, WO 99/19313, WO 99/20614, WO 99/38850, WO 00/23415, WO 00/23417, WO 00/23445, WO 00/50414, WO 01/00579, WO 01/79150, WO 02/062799, WO 03/033481, WO 03/033450, WO 03/033453; and (14) other insulin sensitizing drugs; (15) VPAC2 receptor agonists; (16) GLK modulators, such as PSN105, RO 281675, RO 274375 and those disclosed in WO 03/015774, WO 03/000262, WO 03/055482, WO 04/046139, WO 04/045614, WO 04/063179, WO 04/063194, WO 04/050645, and the like; (17) retinoid modulators such as those disclosed in WO 03/000249; (18) GSK 3beta/GSK 3 inhibitors such as 4-[2-(2-bromophenyl)-4-(4-fluorophenyl-1H-imidazol-5-yl] pyridine, CT21022, CT20026, CT-98023, SB-216763, SB410111, SB-675236, CP-70949, XD4241 and those compounds disclosed in WO 03/037869, 03/03877, 03/037891, 03/024447, 05/000192, 05/019218 and the like; (19) glycogen phosphorylase (HGLPa) inhibitors, such as AVE 5688, PSN 357, GPi-879, those disclosed in WO 03/037864, WO 03/091213, WO 04/092158, WO 05/013975, WO 05/013981, US 2004/0220229, and JP 2004-196702, and the like; (20) ATP consumption promotors such as those disclosed in WO 03/007990; (21) fixed combinations of PPAR γ agonists and metformin such as AVANDAMET; (22) PPAR pan agonists such as GSK 677954; (23) GPR40 (G-protein coupled receptor 40) also called SNORF 55 such as BG 700, and those disclosed in WO 04/041266, 04/022551, 03/099793; (24) GPR119 (also called RUP3; SNORF 25) such as RUP3, HGPRBMY26, PFI 007, SNORF 25; (25) adenosine receptor 2B antagonists such as ATL-618, AT1-802, E3080, and the like; (26) carnitine palmitoyl transferase inhibitors such as ST 1327, and ST 1326, and the like; (27) Fructose 1,6-bisphospohatase inhibitors such as CS-917, MB7803, and the like; (28) glucagon antagonists such as AT77077, BAY 694326, GW 4123X, NN2501, and those disclosed in WO 03/064404, WO 05/00781, US 2004/0209928, US 2004/029943, and the like; (30) glucose-6-phosphase inhibitors; (31) phosphoenolpyruvate carboxykinase (PEPCK) inhibitors; (32) pyruvate dehydrogenase kinase (PDK) activators; (33) RXR agonists such as MC1036, CS00018, JNJ 10166806, and those disclosed in WO 04/089916, U.S. Pat. No. 6759546, and the like; (34) SGLT inhibitors such as AVE 2268, KGT 1251, T1095/RWJ 394718; (35) BLX-1002;

(b) lipid lowering agents such as (1) bile acid sequestrants such as, cholestyramine, colesevelem, colestipol, dialkylaminoalkyl derivatives of a cross-linked dextran; ColestidS; LoCholest®; and Questran®, and the like; (2) HMG-CoA reductase inhibitors such as atorvastatin, itavastatin, pitavastatin, fluvastatin, lovastatin, pravastatin, rivastatin, rosuvastatin, simvastatin, rosuvastatin (ZD-4522), and the like, particularly simvastatin; (3) HMG-CoA synthase inhibitors; (4) cholesterol absorption inhibitors such as FMVP4 (Forbes Medi-Tech), KT6-971 (Kotobuki Pharmaceutical), FM-VA12 (Forbes Medi-Tech), FM-VP-24 (Forbes Medi-Tech), stanol esters, beta-sitosterol, sterol glycosides such as tiqueside; and azetidinones such as ezetimibe, and those disclosed in WO 04/005247 and the like; (5) acyl coenzyme A -cholesterol acyl transferase (ACAT) inhibitors such as avasimibe, eflucimibe, pactimibe (KY505), SMP 797 (Sumitomo), SM32504 (Sumitomo), and those disclosed in WO 03/091216, and the like; (6) CETP inhibitors such as JTT 705 (Japan Tobacco), torcetrapib, CP 532,632, BAY63-2149 (Bayer), SC 591, SC 795, and the like; (7) squalene synthetase inhibitors; (8) anti-oxidants such as probucol, and the like; (9) PPAR(X agonists such as beclofibrate, benzafibrate, ciprofibrate, clofibrate, etofibrate, fenofibrate, gemcabene, and gemfibrozil, GW 7647, BM 170744 (Kowa), LY518674 (Lilly), GW590735 (GlaxoSmithkline), KRP-101 (Kyorin), DRF10945 (Dr. Reddy), NS-220/R1593 (Nippon Shinyaku/Roche, ST1929 (Sigma Tau) MC3001/MC3004 (MaxoCore Pharmaceuticals, gemcabene calcium, other fibric acid derivatives, such as Atromid®, Lopid® and Tricor®, and those disclosed in U.S. Pat. No. 6,548,538, and the like; (10) FXR receptor modulators such as GW 4064 (GlaxoSmithkline), SR 103912, QRX401, LN-6691 (Lion Bioscience), and those disclosed in WO 02/064125, WO 04/045511, and the like; (11) LXR receptor modulators such as GW 3965 (GlaxoSmithkline), T9013137, and XTC0179628 (X-Ceptor Therapeutics/Sanyo), and those disclosed in WO 03/031408, WO 03/063796, WO 04/072041, and the like; (12) lipoprotein synthesis inhibitors such as niacin; (13) renin angiotensin system inhibitors; (14) PPAR δ partial agonists, such as those disclosed in WO 03/024395; (15) bile acid reabsorption inhibitors, such as BAR11453, SC435, PHA384640, S8921, AZD7706, and the like; and bile acid sequesterants such as colesevelam (WELCHOL/CHOLESTAGEL), (16) PPARδ agonists such as GW 501516 (Ligand, GSK), GW 590735, GW-0742 (GlaxoSmithkline), T659 (Amgen/Tularik), LY934 (Lilly), NNC610050 (Novo Nordisk) and those disclosed in WO97/28149, WO 01/79197, WO 02/14291, WO 02/46154, WO 02/46176, WO 02/076957, WO 03/016291, WO 03/033493, WO 03/035603, WO 03/072100, WO 03/097607, WO 04/005253, WO 04/007439, and JP10237049, and the like; (17) triglyceride synthesis inhibitors; (18) microsomal triglyceride transport (MTTP) inhibitors, such as implitapide, LAB687, JTT130 (Japan Tobacco), CP346086, and those disclosed in WO 03/072532, and the like; (19) transcription modulators; (20) squalene epoxidase inhibitors; (21) low density lipoprotein (LDL) receptor inducers; (22) platelet aggregation inhibitors; (23) 5-LO or FLAP inhibitors; and (24) niacin receptor agonists including HM74A receptor agonists; (25) PPAR modulators such as those disclosed in WO 01/25181, WO 01/79150, WO 02/79162, WO 02/081428, WO 03/016265, WO 03/033453; (26) niacin-bound chromium, as disclosed in WO 03/039535; (27) substituted acid derivatives disclosed in WO 03/040114; (28) infused HDL such as LUV/ETC-588 (Pfizer), APO-A1 Milano/ETC216 (Pfizer), ETC-642 (Pfizer), ISIS301012, D4F (Bruin Pharma), synthetic trimeric ApoA1, Bioral Apo A1 targeted to foam cells, and the like; (29) IBAT inhibitors such as BARI143/HMR145A/HMR1453 (Sanofi-Aventis, PHA384640E (Pfizer), S8921 (Shionogi) AZD7806 (AstrZeneca), AK105 (Asah Kasei), and the like; (30) Lp-PLA2 inhibitors such as SB480848 (GlaxoSmithkline), 659032 (GlaxoSmithkline), 677116 (GlaxoSmithkline), and the like; (31) other agents which affect lipic composition including ETC 1001/ESP31015 (Pfizer), ESP-55016 (Pfizer), AGI1067 (AtheroGenics), AC3056 (Amylin), AZD4619 (AstrZeneca); and (c) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lermildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapnrl; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, and the like; (8) angiotensin II receptor antagonists such as candesartan, eprosartan, irbesartan, losartan, pratosartan, tasosartan, telmisartan, valsartan, and EXP-3137, F16828K, and RNH6270, and the like; (9) α/β adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XEN0 10, and the like; (11) alpha 2 agonists such as lofexidine, tiamenidine, moxonidine, rilmenidine and guanobenz, and the like; (12) aldosterone inhibitors, and the like; (13) angiopoietin-2-binding agents such as those disclosed in WO 03/030833; and (d) anti-obesity agents, such as (1) 5HT (serotonin) transporter inhibitors, such as paroxetine, fluoxetine, fenfluramine, fluvoxamine, sertraline, and imipramine, and those disclosed in WO 03/00663, as well as serotonin/noradrenaline re uptake inhibitors such as sibutramine (MERIDLA/ REDUCTIL) and dopamine uptake inhibitor/Norepenephrine uptake inhibitors such as radafaxine hydrochloride, 353162 (GlaxoSmithkline), and the like; (2) NE (norepinephrine) transporter inhibitors, such as GW 320659, despiramine, talsupram, and nomifensine; (3) CB1 (cannabinoid-1 receptor) antagonist/inverse agonists, such as rimonabant (ACCOMPLIA Sanofi Synthelabo), SR-147778 (Sanofi Synthelabo), AVE1625 (Sanofi-Aventis), BAY 65-2520 (Bayer), SLV 319 (Solvay), SLV326 (Solvay), CP945598 (Pfizer), E-6776 (Esteve), 01691 (Organix), ORG14481 (Organon), VER24343 (Vernalis), NESS0327 (Univ of Sassari/Univ of Cagliari), and those disclosed in U.S. Pat. Nos. 4,973,587, 5,013,837, 5,081,122, 5,112,820, 5,292,736, 5,532,237, 5,624,941, 6,028,084, and 6,509367; and WO 96/33159, WO97/29079, WO98/31227, WO 98/33765, WO98/37061, WO98/41519, WO98/43635, WO98/43636, WO99/02499, WO0010967, WO00/10968, WO 01/09120, WO 01/58869, WO 01/64632, WO 01/64633, WO 01/64634, WO 01/70700, WO 01/96330, WO 02/076949, WO 03/006007, WO 03/007887, WO 03/020217, WO 03/026647, WO 03/026648, WO 03/027069, WO 03/027076, WO 03/027114, WO 03/037332, WO 03/040107, WO 04/096763, WO 04/111039, WO 04/111033, WO 04/111034, WO 04/111038, WO 04/013120, WO 05/000301, WO 05/016286, WO 05/066126 and EP-658546 and the like; (4) ghrelin agonists/antagonists, such as BVT81-97 (BioVitrum), RC1291 (Rejuvenon), SRD-04677 (Sumitomo), unacylated ghrelin (TheraTechnologies), and those disclosed in WO 01/87335, WO 02/08250, WO 05/012331, and the like; (5) H3 (histamine H3) antagonist/ inverse agonists, such as thioperamide, 3-(1H-imidazol-4-yl) propyl N-(4-pentenyl)carbamate), clobenpropit, iodophenpropit, imoproxifan, GT2394 (Gliatech), and A331440, and those disclosed in WO 02/15905; and O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm.(Weinheim) 334: 45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)) and histamine H3 receptor modulators such as those disclosed in WO 03/024928 and WO 03/024929; (6) melanin-concentrating hormone 1 receptor (MCH1R) antagonists, such as T-226296 (Takeda), T71 (Takeda/Amgen), AMGN-608450, AMGN-503796 (Amgen), 856464 (GlaxoSmithkline), A224940 (Abbott), A798 (Abbott), ATC0175/Ar224349 (Arena Pharmaceuticals), GW803430 (GlaxoSmithkine), NBI-1A (Neurocrine Biosciences), NGX-1 (Neurogen), SNP-7941 (Synaptic), SNAP9847 (Synaptic), T-226293 (Schering Plough), TPI-1361-17 (Saitama Medical School/ University of California Irvine), and those disclosed WO 01/21169, WO 01/82925, WO 01/87834, WO 02/051809, WO 02/06245, WO 02/076929, WO 02/076947, WO 02/04433, WO 02/51809, WO 02/083134, WO 02/094799, WO 03/004027, WO 03/13574, WO 03/15769, WO 03/028641, WO 03/035624, WO 03/033476, WO 03/033480, WO 04/004611, WO 04/004726, WO 04/011438, WO 04/028459, WO 04/034702, WO 04/039764, WO 04/052848, WO 04/087680; and Japanese Patent Application Nos. JP 13226269, JP 1437059, JP2004315511, and the like; (7) MCH2R (melanin concentrating hormone 2R) agonist/antagonists; (8) NPY1 (neuropeptide YY1) antagonists, such as BMS205749, BIBP3226, J-115814, BIBO 3304, LY-357897, CP-671906, and GI-264879A; and those disclosed in U.S. Pat. No. 6,001,836; and WO 96/14307, WO 01/23387, WO 99/51600, WO 01/85690, WO 01/85098, WO 01/85173, and WO 01/89528; (9) NPY5 (neuropeptide Y Y5) antagonists, such as 152,804, S2367 (Shionogi), E-6999 (Esteve), GW-569180A, GW-594884A (GlaxoSmthkline), GW-587081X, GW-548118X; FR 235,208; FR226928, FR 240662, FR252384; 1229U91, GI-264879A, CGP71683A, C-75 (Fasgen) LY-377897, LY366377, PD-160170, SR-120562A, SR-120819A,S2367 (Shionogi), JCF-104, and H409/22; and those compounds disclosed in U.S. Pat. Nos. 6,140,354, 6,191,160, 6,258,837, 6,313,298, 6,326,375, 6,329,395, 6,335,345, 6,337,332, 6,329,395, and 6,340,683 ; and EP-01010691, EP-01044970, and FR252384; and PCT Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, WO 02/051806, WO 02/094789, WO 03/009845, WO 03/014083, WO 03/022849, WO 03/028726, WO 05/014592, WO 05/01493; and Norman et al., J. Med. Chem. 43:4288-4312 (2000); (10) leptin, such as recombinant human leptin (PEG-OB, Hoffinan La Roche) and recombinant methionyl human leptin (Amgen); (11) leptin derivatives, such as those disclosed in U.S. Pat. Nos. 5,552,524; 5,552,523; 5,552,522; 5,521,283; and WO 96/23513; WO 96/23514; WO 96/23515; WO 96/23516; WO 96/23517; WO 96/23518; WO 96/23519; and WO 96/23520; (12) opioid antagonists, such as nalmefene (Revex®), 3-methoxynaltrexone, naloxone, and naltrexone; and those disclosed in WO 00/21509; (13) orexin antagonists, such as SB-334867-A (GlaxoSmithkline); and those disclosed in WO 01/96302, 01/68609, 02/44172, 02/51232, 02/51838, 02/089800, 02/090355, 03/023561, 03/032991, 03/037847, 04/004733, 04/026866, 04/041791, 04/085403, and the like; (14) BRS3 (bombesin receptor subtype 3) agonists; (15) CCK-A (cholecystokinin-A) agonists, such as AR-R 15849, GI 181771, JMV-180, A-71378, A-71623, PD170292, PD 149164, SR146131, SR125180, butabindide, and those disclosed in U.S. Pat. No. 5,739,106; (16) CNTF (ciliary neurotrophic factors), such as GI-181771 (Glaxo-SmithKline); SR146131 (Sanofi Synthelabo); butabindide; and PD170,292, PD 149164 (Pfizer); (17) CNTF derivatives, such as axokine (Regeneron); and those disclosed in WO 94/09134, WO 98/22128, and WO 99/43813; (18) GHS (growth hormone secretagogue receptor) agonists, such as NN703, hexarelin, MK-0677, SM-130686, CP-424,391, L-692,429 and L-163,255, and those disclosed in U.S. Pat. No. 6,358,951, U.S. Patent Application Nos. 2002/049196 and 2002/022637; and WO 01/56592, and WO 02/32888; (19) 5HT2c (serotonin receptor 2c) agonists, such as APD3546/AR10A (Arena Pharmaceuticals), ATH88651 (Athersys), ATH88740 (Athersys), BVT933 (Biovitrum/ GSK), DPCA37215 (BMS), IK264; LY448100 (Lilly), PNU 22394; WAY 470 (Wyeth), WAY629 (Wyeth), WAY161503 (Biovitrum), R-1065, VR1065 (Vernalis/Roche) YM 348; and those disclosed in U.S. Pat. No. 3,914,250; and PCT Publications 01/66548, 02/36596, 02/48124, 02/10169, 02/44152; 02/51844; 02/40456, 02/40457, 03/057698, 05/000849, and the like; (20) Mc3r (melanocortin 3 receptor) agonists; (21) Mc4r (melanocortin 4 receptor) agonists, such as CHIR86036 (Chiron), CHIR915 (Chiron); ME-10142 (Melacure), ME-10145 (Melacure), HS-131 (Melacure), NBI72432 (Neurocrine Biosciences), NNC 70-619 (Novo Nordisk), TTP2435 (Transtech)and those disclosed in PCT Publications WO 99/64002, 00/74679, 01/991752, 01/0125192, 01/52880, 01/74844, 01/70708, 01/70337, 01/91752, 01/010842, 02/059095, 02/059107, 02/059108, 02/059117, 02/062766, 02/069095, 02/12166, 02/11715, 02/12178, 02/15909, 02/38544, 02/068387, 02/068388, 02/067869, 02/081430, 03/06604, 03/007949, 03/009847, 03/009850, 03/013509, 03/031410, 03/094918, 04/028453, 04/048345, 04/050610, 04/075823, 04/083208, 04/089951, 05/000339, and EP 1460069, and US 2005049269, and JP2005042839, and the like; (22) monoamine reuptake inhibitors, such as sibutratmine (Meridia®/Reductil®) and salts thereof, and those compounds disclosed in U.S. Pat. Nos. 4,746,680, 4,806,570, and 5,436,272, and U.S. Patent Publication No. 2002/0006964, and WO 01/27068, and WO 01/62341; (23) serotonin reuptake inhibitors, such as dexfenfluramine, fluoxetine, and those in U.S. Pat. No. 6,365,633, and WO 01/27060, and WO 01/162341; (24) GLP-1 (glucagon-like peptide 1) agonists; (25) Topiramate (Topimax®); (26) phytopharm compound 57 (CP 644,673); (27) ACC2 (acetyl-CoA carboxylase-2) inhibitors; (28)β3 (beta adrenergic receptor 3) agonists, such as rafebergron/AD9677/ TAK677 (Dainippon/Takeda), CL-316,243, SB 418790, BRL-37344, L-796568, BMS-196085, BRL-35135A, CGP12177A, BTA-243, GRC1087 (Glenmark Pharmaceuticals) GW 427353 (solabegron hydrochloride), Trecadrine, ZenecaD7114, N-5984 (Nisshin Kyorin), LY-377604 (Lilly), KT07924 (Kissei), SR 59119A, and those disclosed in US Pat. Nos. 5,705,515, US 5,451,677; and WO94/18161, WO95/29159, WO97/46556, WO98/04526 WO98/32753, WO 01/74782, WO 02/32897, WO 03/014113, WO 03/016276, WO 03/016307, WO 03/024948, WO 03/024953, WO 03/037881, WO 04/108674, and the like; (29) DGAT1 (diacylglycerol acyltransferase 1) inhibitors; (30) DGAT2 (diacylglycerol acyltransferase 2)inhibitors; (31) FAS (fatty acid synthase) inhibitors, such as Cerulenin and C75; (32) PDE (phosphodiesterase) inhibitors, such as theophylline, pentoxifylline, zaprinast, sildenafil, amrinone, milrinone, cilostamide, rolipram, and cilomilast, as well as those described in WO 03/037432, WO 03/037899; (33) thyroid hormone β agonists, such as KB-2611 (KaroBioBMS), and those disclosed in WO 02/15845; and Japanese Patent Application No. JP 2000256190; (34) UCP-1 (uncoupling protein 1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; and those disclosed in WO 99/00123; (35) acyl-estrogens, such as oleoyl-estrone, disclosed in del Mar-Grasa, M. et al., Obesity Research, 9:202-9 (2001); (36) glucocorticoid receptor antagonists, such as CP472555 (Pfizer), KB 3305, and those disclosed in WO 04/000869, WO 04/075864, and the like; (37) 11β HSD-1 (11-beta hydroxy steroid dehydrogenase type 1) inhibitors, such as BVT 3498 (AMG 331), BVT 2733, 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, 3-adamantanyl-4,5,6,7,8,9,10,11,12,3a-decahydro-1,2,4-triazolo[4,3-a][11]annulene, and those compounds disclosed in WO 01/90091, 01/90090, 01/90092, 02/072084, 04/011410, 04/033427, 04/041264, 04/027047, 04/056744, 04/065351, 04/089415, 04/037251, and the like; (38) SCD-1 (stearoyl-CoA desaturase-1) inhibitors; (39) dipeptidyl peptidase IV (DP-IV) inhibitors, such as isoleucine thiazolidide, valine pyrrolidide, saxagliptin, NVP-DPP728, LAF237 (vildagliptin), P93/01, TSL 225, TMC-2A/2B/2C, FE 999011, P9310/K364, VIP 0177, SDZ 274-444, GSK 823093, E 3024, SYR 322, TS021, SSR 162369, GRC 8200, K579, NN7201, CR 14023, PHX 1004, PHX 1149, PT-630, SK-0403; and the compounds disclosed in WO 02/083128, WO 02/062764, WO 02/14271, WO 03/000180, WO 03/000181, WO 03/000250, WO 03/002530, WO 03/002531, WO 03/002553, WO 03/002593, WO 03/004498, WO 03/004496, WO 03/005766, WO 03/017936, WO 03/024942, WO 03/024965, WO 03/033524, WO 03/055881, WO 03/057144, WO 03/037327, WO 04/041795, WO 04/071454, WO 04/0214870, WO 04/041273, WO 04/041820, WO 04/050658, WO 04/046106, WO 04/067509, WO 04/048532, WO 04/099185, WO 04/108730, WO 05/009956, WO 04/09806, WO 05/023762, US 2005/043292, and EP 1 258 476; (40) lipase inhibitors, such as tetrahydrolipstatin (orlistat/XENICAL), ATL962 (Alizyme/Takeda), GT389255 (Genzyme/Peptimmune)Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC 80267, and those disclosed in WO 01/77094, WO 04/111004, and U.S. Pat. Nos. 4,598,089, 4,452,813, 5,512,565, 5,391,571, 5,602,151, 4,405,644, 4,189,438, and 4,242,453, and the like; (41) fatty acid transporter inhibitors; (42) dicarboxylate transporter inhibitors; (43) glucose transporter inhibitors; and (44) phosphate transporter inhibitors; (45) anorectic bicyclic compounds such as 1426 (Aventis) and 1954 (Aventis), and the compounds disclosed in WO 00/18749, WO 01/32638, WO 01/62746, WO 01/62747, and WO 03/015769; (46) peptide YY and PYY agonists such as PYY336 (Nastech/Merck), AC162352 (IC Innovations/Curis/Amylin), TM30335/TM30338 (7TM Pharma), PYY336 (Emisphere Tehcnologies), pegylated peptide YY3-36, those disclosed in WO 03/026591, 04/089279, and the like; (47) lipid metabolism modulators such as maslinic acid, erythrodiol, ursolic acid uvaol, betulinic acid, betulin, and the like and compounds disclosed in WO 03/011267; (48) transcription factor modulators such as those disclosed in WO 03/026576; (49) Mc5r (melanocortin 5 receptor) modulators, such as those disclosed in WO 97/19952, WO 00/15826, WO 00/15790, US 20030092041, and the like; (50) Brain derived neutotropic factor (BDNF), (51) Mc1r (melanocortin 1 receptor modulators such as LK-184 (Proctor & Gamble), and the like; (52) 5HT6 antagonists such as BVT74316 (BioVitrum), BVT5182c (BioVitrum), E-6795 (Esteve), E-6814 (Esteve), SB399885 (GlaxoSmithkline), SB271046 (GlaxoSmithkline), RO-046790 (Roche), and the like; (53) fatty acid transport protein 4 (FATP4); (54) acetyl-CoA carboxylase (ACC) inhibitors such as CP640186, CP610431, CP640188 (Pfizer); (55) C-terminal growth hormone fragments such as AOD9604 (Monash Univ/Metabolic Pharmaceuticals), and the like; (56) oxyntomodulin; (57) neuropeptide FF receptor antagonists such as those disclosed in WO 04/083218, and the like; (58) amylin agonists such as Symlin/pramlintide/AC137 (Amylin); (59) Hoodia and trichocaulon extracts; (60) BVT74713 and other gut lipid appetite suppressants; (61) dopamine agonists such as bupropion (WELLBUTRIN/GlaxoSmithkline); (62) zonisamide (ZONEGRAN/Dainippon/Elan), and the like.

Specific NPY5 antagonists of use in combination with a compound of the present invention include: 3-oxo-N-(5-phenyl-2-pyrazinyl)-spiro[isobenzofuran-1(3H),4'-piperidine]-1'-carboxamide, 3-oxo-N-(7-trifluoromethylpyrido[3,2-b]pyridin-2-yl)spiro-[isobenzofuran-1(3H),4'-piperidine]-1'-carboxamide, N-[5-(3-fluorophenyl)-2-pyrimidinyl]-3-oxospiro-[isobenzofuran-1(3H),4'-piperidine]-1'-carboxamide, trans-3'-oxo-N-(5-phenyl-2-pyrimidinyl)spiro[cyclohexane-1,1'(3'H)-isobenzofuran]-4-carboxamide, trans-3'-oxo-N-[1-(3-quinolyl)-4-imidazolyl]spiro[cyclohexane-1,1'(3'H)-isobenzofuran]-4-carboxamide, trans-3-oxo-N-(5-phenyl-2-pyrazinyl)spiro[4-azaiso-benzofuran-1 (3H),1'-cyclohexane]-4'-carboxamide, trans-N-[5-(3-fluorophenyl)-2-pyrimidinyl]-3-oxospiro[5- azaisobenzofuran-1(3H),1'-cyclohexane]-4'-carboxamide, trans-N-[5-(2-fluorophenyl)-2-pyrimidinyl]-3-oxospiro[5-azaisobenzofuran-1(3H),1'-cyclohexane]-4'-carboxamide, trans-N-[1-(3,5-difluorophenyl)-4-imidazolyl]-3-oxospiro [7-azaisobenzofuran-1(3H),1'-cyclohexane]4'-carboxamide, trans-3-oxo-N-(1-phenyl-4-pyrazolyl)spiro[4-azaisobenzofuran-1(3H),1'-cyclohexane]-4'-carboxamide, trans-N-[1-(2-fluorophenyl)-3-pyrazolyl]-3-oxospiro[6-azaisobenzofuran-1(3H),1'-cyclohexane]4'-carboxamide, trans-3-oxo-N-(1-phenyl-3-pyrazolyl)spiro[6-azaisobenzofuran-1(3H),1'-cyclohexane]-4'-carboxamide, trans-3-oxo-N-(2-phenyl-1,2,3-triazol-4-yl)spiro[6-azaisobenzofuran-1(3H),1'-cyclohexane]-4'-carboxamide, and pharmaceutically acceptable salts and esters thereof.

Specific DP-IV inhibitors of use in combination with a compound of the present invention are selected from 7-[(3R)-3-amino-4-(2,4,5-trifluorophenyl)butanoyl]-3-(trifluoromethyl)-5,6,7,8-tetrahydro-1,2,4-triazolo[4,3-a]pyrazine. In particular, the compound of formula I is favorably combined with 7-[(3R)-3-amino-4-(2,4,5-trifluorophenyl)butanoyl]-3-(trifluoromethyl)-5,6,7,8-tetrahydro-1,2,4-triazolo[4,3-a]pyrazine, and pharmaceutically acceptable salts thereof.

"Obesity" is a condition in which there is an excess of body fat. The operational definition of obesity is based on the Body Mass Index (BMI), calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk for obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asian countries, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes, non-insulin dependent diabetes mellitus—type 2, impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

"Treatment" (of obesity and obesity-related disorders) refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

"Prevention" (of obesity and obesity-related disorders) refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and aryythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The compounds of formula I are also useful for treating or preventing obesity and obesity-related disorders in cats and dogs. As such, the term "mammal" includes companion animals such as cats and dogs.

The term "diabetes," as used herein, includes both insulin-dependent diabetes mellitus (IDDM, also known as type I diabetes) and non-insulin-dependent diabetes mellitus (NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compounds of the present invention are useful for treating both Type I and Type II diabetes. The compounds are especially effective for treating Type II diabetes. The compounds of the present invention are also useful for treating and/or preventing gestational diabetes mellitus.

It will be appreciated that for the treatment or prevention of migraine, a compound of the present invention may be used in conjunction with other anti-migraine agents, such as ergotamines or 5—HT$_1$ agonists, especially sumatriptan, naratriptan, zolmatriptan or rizatriptan.

It will be appreciated that for the treatment of depression or anxiety, a compound of the present invention may be used in conjunction with other anti-depressant or anti-anxiety agents.

Suitable classes of anti-depressant agents include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, cc-adrenoreceptor antagonists, neurokinin-1 receptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine, imipramine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677. Still further, neurokinin-1 (NK-1) receptor antagonists may be favorably employed with the CB1 receptor modulators of the present invention. NK-1 receptor antagonists of use in the present invention are fully described in the art. Specific neurokinin-1 receptor antagonists of use in the present invention include: (±)-(2R3R,2S3 S)-N-{[2-cyclopropoxy-5-(trifluoromethoxy)-phenyl]methyl}-2-phenylpiperidin-3-amine; 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine; aperpitant; CJ17493; GW597599; GW679769; R673; R067319; R1124; R1204; SSR146977; SSR240600; T-2328; and T2763.; or a pharmaceutically acceptable salts thereof.

Suitable atypical anti-depressants include: bupropion, lithium, nefazodone, trazodone and viloxazine, and pharmaceutically acceptable salts thereof.

Suitable classes of anti-anxiety agents include benzodiazepines and 5-HT$_{1A}$ agonists or antagonists, especially 5-HT$_{1A}$ partial agonists, and corticotropin releasing factor (CRF) antagonists. Suitable benzodiazepines include: alprazolam, chlordiazepoxide, clonazepam, chlorazepate, diazepam, halazepam, lorazepam, oxazepam and prazepam, and pharmaceutically acceptable salts thereof. Suitable 5-HT$_{1A}$ receptor agonists or antagonists include, in particular, the 5-HT$_{1A}$ receptor partial agonists buspirone, flesinoxan, gepirone and ipsapirone, and pharmaceutically acceptable salts thereof. Suitable corticotropin releasing factor (CRF) antagonists include those previously discussed herein.

As used herein, the term "substance abuse disorders" includes substance dependence or abuse with or without physiological dependence. The substances associated with these disorders are: alcohol, amphetamines (or amphetamine-like substances), caffeine, cannabis, cocaine, hallucinogens, inhalants, marijuana, nicotine, opioids, phencyclidine (or phencyclidine-like compounds), sedative-hypnotics or benzodiazepines, and other (or unknown) substances and combinations of all of the above.

In particular, the term "substance abuse disorders" includes drug withdrawal disorders such as alcohol withdrawal with or without perceptual disturbances; alcohol withdrawal delirium; amphetamine withdrawal; cocaine withdrawal; nicotine withdrawal; opioid withdrawal; sedative, hypnotic or anxiolytic withdrawal with or without perceptual disturbances; sedative, hypnotic or anxiolytic withdrawal delirium; and withdrawal symptoms due to other substances. It will be appreciated that reference to treatment of nicotine withdrawal includes the treatment of symptoms associated with smoking cessation.

Other "substance abuse disorders" include substance-induced anxiety disorder with onset during withdrawal; substance-induced mood disorder with onset during withdrawal; and substance-induced sleep disorder with onset during withdrawal.

In particular, compounds of structural formula I are useful for aiding in stopping consumption of tobacco and are useful in treating nicotine dependence and nicotine withdrawal. The compounds of formula I produce in consumers of nicotine, such as tobacco smokers, a total or partial abstinence from smoking. Further, withdrawal symptoms are lessened and the weight gain that generally accompanies quitting tobacco comsumption is reduced or nonexistent. For smoking cessation, the compound of form I may be used in combination with a nicotine agonist or a partial nicotine agonist, including varenicline and selective alpha-4 beta 2 nicotinic partial agonists such as SSR 591813, or a monoamine oxidase inhibitor (MAOI), or another active ingredient demonstrating efficacy in aiding cessation of tobacco consumption; for example, an antidepressant such as bupropion, doxepine, ornortriptyline; or an anxiolytic such as buspirone or clonidine.

It will be appreciated that a combination of a conventional antipsychotic drug with a CB1 receptor modulator may provide an enhanced effect in the treatment of mania. Such a combination would be expected to provide for a rapid onset of action to treat a manic episode thereby enabling prescription on an "as needed basis". Furthermore, such a combination may enable a lower dose of the antipsychotic agent to be used without compromising the efficacy of the antipsychotic agent, thereby minimizing the risk of adverse side-effects. A yet further advantage of such a combination is that, due to the action of the CB1 receptor modulator, adverse side-effects caused by the antipsychotic agent such as acute dystonias, dyskinesias, akathesia and tremor may be reduced or prevented.

Thus, according to a further aspect of the present invention there is provided the use of a CB1 receptor modulator and an antipsychotic agent for the manufacture of a medicament for the treatment or prevention of mania.

The present invention also provides a method for the treatment or prevention of mania, which method comprises administration to a patient in need of such treatment or at risk of developing mania of an amount of a CB1 receptor modulator and an amount of an antipsychotic agent, such that together they give effective relief.

In a further aspect of the present invention, there is provided a pharmaceutical composition comprising a CB1 receptor modulator and an antipsychotic agent, together with at least one pharmaceutically acceptable carrier or excipient, wherein the CB1 receptor modulator and the antipsychotic agent may be present as a combined preparation for simultaneous, separate or sequential use for the treatment or prevention of mania. Such combined preparations may be, for example, in the form of a twin pack.

In a further or alternative aspect of the present invention, there is therefore provided a product comprising a CB1 receptor modulator and an antipsychotic agent as a combined preparation for simultaneous, separate or sequential use in the treatment or prevention of mania.

It will be appreciated that when using a combination of the present invention, the CB1 receptor modulator and the antipsychotic agent may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, the antipsychotic agent may be administered as a tablet and then, within a reasonable period of time, the CB1 receptor modulator may be administered either as an oral dosage form such as a tablet or a fast-dissolving oral dosage form. By a "fast-dissolving oral formulation" is meant, an oral delivery form which when placed on the tongue of a patient, dissolves within about 10 seconds.

Included within the scope of the present invention is the use of CB1 receptor modulators in combination with an antipsychotic agent in the treatment or prevention of hypomania.

It will be appreciated that a combination of a conventional antipsychotic drug with a CB1 receptor modulator may provide an enhanced effect in the treatment of schizophrenic disorders. Such a combination would be expected to provide for a rapid onset of action to treat schizophrenic symptoms thereby enabling prescription on an "as needed basis". Furthermore, such a combination may enable a lower dose of the CNS agent to be used without compromising the efficacy of the antipsychotic agent, thereby minimizing the risk of adverse side-effects. A yet further advantage of such a combination is that, due to the action of the CB1 receptor modulator, adverse side-effects caused by the antipsychotic agent such as acute dystonias, dyskinesias, akathesia and tremor may be reduced or prevented.

As used herein, the term "schizophrenic disorders" includes paranoid, disorganized, catatonic, undifferentiated and residual schizophrenia; schizophreniform disorder; schizoaffective disorder; delusional disorder; brief psychotic disorder; shared psychotic disorder; substance-induced psychotic disorder; and psychotic disorder not otherwise specified.

Other conditions commonly associated with schizophrenic disorders include self-injurious behavior (e.g. Lesch-Nyhan syndrome) and suicidal gestures.

Suitable antipsychotic agents of use in combination with a CB1 receptor modulator include the phenothiazine, thioxanthene, heterocyclic dibenzazepine, butyrophenone, diphenylbutylpiperidine and indolone classes of antipsychotic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. Suitable examples of dibenzazepines include clozapine and olanzapine. An example of a butyrophenone is haloperidol. An example of a diphenylbutylpiperidine is pimozide. An example of an indolone is molindolone. Other antipsychotic agents include loxapine, sulpiride and risperidone. It will be appreciated that the antipsychotic agents when used in combination with a CB1 receptor modulator may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, olanzapine, haloperidol, pimozide and risperidone are commonly used in a non-salt form.

Other classes of antipsychotic agent of use in combination with a CB1 receptor modulator include dopamine receptor antagonists, especially D2, D3 and D4 dopamine receptor antagonists, and muscarinic m1 receptor agonists. An example of a D3 dopamine receptor antagonist is the compound PNU-99194A. An example of a D4 dopamine receptor antagonist is PNU-101387. An example of a muscarinic m1 receptor agonist is xanomeline.

Another class of antipsychotic agent of use in combination with a CB1 receptor modulator is the 5-$HT_{2A}$ receptor antagonists, examples of which include MDL100907 and fananserin. Also of use in combination with a CB1 receptor modulator are the serotonin dopamine antagonists (SDAs) which are believed to combine 5-$HT_{2A}$ and dopamine receptor antagonist activity, examples of which include olanzapine and ziperasidone.

Still further, NK-1 receptor antagonists may be favorably employed with the CB1 receptor modulators of the present invention. Preferred NK-1 receptor antagonists for use in the present invention are selected from the classes of compounds described previously.

It will be appreciated that a combination of a conventional anti-asthmatic drug with a CB1 receptor modulator may provide an enhanced effect in the treatment of asthma, and may be used for the treatment or prevention of asthma, which method comprises administration to a patient in need of such treatment an amount of a compound of the present invention and an amount of an anti-asthmatic agent, such that together they give effective relief.

Suitable anti-asthmatic agents of use in combination with a compound of the present invention include, but are not limited to: (a) VLA-4 antagonists such as natalizumab and the compounds described in U.S. Pat. No. 5,510,332, WO97/03094, WO97/02289, WO96/40781, WO96/22966, WO96/20216, WO96/01644, WO96/06108, WO95/15973 and WO96/31206; (b) steroids and corticosteroids such as beclomethasone, methylprednisolone, betamethasone, prednisone, dexamethasone, and hydrocortisone; (c) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, desloratadine, cetirizine, fexofenadine, descarboethoxyloratadine, and the like; (d) non-steroidal anti-asthmatics including β2-agonists (such as terbutaline, metaproterenol, fenoterol, isoetharine, albuterol, bitolterol, salmeterol, epinephrine, and pirbuterol), theophylline, cromolyn sodium, atropine, ipratropium bromide, leukotriene antagonists (such as zafirlukast, montelukast, pranlukast, iralukast, pobilukast, and SKB-106,203), and leukotriene biosynthesis inhibitors (such as zileuton and BAY-1005); (e) anti-cholinergic agents including muscarinic antagonists (such as ipratropium bromide and atropine); and (f) antagonists of the chemokine receptors, especially CCR-3; and pharmaceutically acceptable salts thereof.

It will be appreciated that a combination of a conventional anti-constipation drug with a CB1 receptor modulator may provide an enhanced effect in the treatment of constipation or chronic intestinal pseudo-obstruction, and for use for the manufacture of a medicament for the treatment or prevention of constipation or chronic intestinal pseudo-obstruction.

The present invention also provides a method for the treatment or prevention of constipation, which method comprises administration to a patient in need of such treatment an amount of a compound of the present invention and an amount of an anti-constipation agent, such that together they give effective relief.

Suitable anti-constipation agents of use in combination with a compound of the present invention include, but are not limited to, osmotic agents, laxatives and detergent laxatives (or wetting agents), bulking agents, and stimulants; and pharmaceutically acceptable salts thereof. A particularly suitable class of osmotic agents include, but are not limited to sorbitol, lactulose, polyethylene glycol, magnesium, phosphate, and sulfate; and pharmaceutically acceptable salts thereof. A particularly suitable class of laxatives and detergent laxatives, include, but are not limited to, magnesium, and docusate sodium; and pharmaceutically acceptable salts thereof. A particularly suitable class of bulking agents include, but are not limited to, psyllium, methylcellulose, and calcium polycarbophil; and pharmaceutically acceptable salts thereof. A particularly suitable class of stimulants include, but are not limited to, anthroquinones, and phenolphthalein; and pharmaceutically acceptable salts thereof.

It will be appreciated that a combination of a conventional anti-cirrhosis drug with a CB1 receptor modulator may provide an enhanced effect in the treatment or prevention of cirrhosis of the liver, and for use for the manufacture of a medicament for the treatment or prevention of cirrhosis of the liver, as well as non-alcoholic fatty liver disease (NAFLD) and non-alcoholic steatohepatitis (NASH).

The present invention also provides a method for the treatment or prevention of cirrhosis of the liver, which method comprises administration to a patient in need of such treatment an amount of a compound of the present invention and an anti-cirrhosis agent, such that together they give effective relief.

Suitable anti-cirrhosis agents of use in combination with a compound of the present invention include, but are not limited to, corticosteroids, penicillamine, colchicine, interferon-γ, 2-oxoglutarate analogs, prostaglandin analogs, and other anti-inflammatory drugs and antimetabolites such as azathioprine, methotrexate, leflunamide, indomethacin, naproxen, and 6-mercaptopurine; and pharmaceutically acceptable salts thereof.

The method of treatment of this invention comprises a method of modulating the CB1 receptor and treating CB1 receptor mediated diseases by administering to a patient in need of such treatment a non-toxic therapeutically effective amount of a compound of this invention that selectively antagonizes the CB1 receptor in preference to the other CB or G-protein coupled receptors.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans, and companion animals such as dogs and cats.

The weight ratio of the compound of the Formula I to the second active ingredient may be varied and will depend upon the effective dose of each ingredient. Generally, an effective dose of each will be used. Thus, for example, when a compound of the Formula I is combined with a β-3 agonist the weight ratio of the compound of the Formula I to the β-3 agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Abbreviations used in the following Schemes and Examples:

aq or aq.: aqueous; BOC or boc: benzyloxycarbonyl; brine: saturated sodium chloride solution; Bu: butyl; DAST: diethylaminosulfur trifluoride; DBU: 1,8-diazabicyclo[5.4.0]undec-7-ene; DIBAL-H: diisobutyl aluminum hydride; DIEA: N,N-diisopropyl ethyl amine; DMAP: 4-dimethylaminopyridine; DMF: dimethylformamide; DMSO: dimethylsulfoxide; DPPF: 1,1'-bis(diphenylphosphino)ferrocene; EDAC: 1-ethyl-3-(3,3-dimethylaminopropyl)-carbodiimide hydrochloride; Et: ethyl; g or gm: gram; h or hr: hours; HOAc: acetic acid; HOBT: 1-hydroxybenzotriazole; HPLC: high pressure liquid chromatography; HPLC/MS: high pressure liquid chromatography/mass spectroscopy; in vacuo: rotoevaporation; iPr: isopropyl; LC-MS or LCMS: liquid chromatography-mass spectrum; LHMDS: Lithium Hexamethyl Disilylamide-LiN(SiMe$_3$)$_2$; M: molar; mCPBA: 3-chloroperbenzoic acid; Me: methyl; mg: milligram; MHz: megahertz; min: minutes; mL: milliliter; mmol: millimole; MPLC: medium pressure liquid chromatography; MS or ms: mass spectrum; Ms: mesyl (methane sulfonyl); N/A: Not applicable; NaHMDS: sodium hexamethyl disilylamide; Ox-Cl: oxalyl chloride; Ph: phenyl; psi: pounds per square inch; rt or RT: room temperature; Rt: retention time; TFA: trifluoroacetic acid; THF: tetrahydrofuran; TLC: thin layer chromatography; μL, , μl, μL or μl: microliter; UV: ultra-violet.

Compounds of the present invention may be prepared by procedures illustrated in the accompanying schemes.

Compounds of the present invention may be prepared by procedures illustrated in the accompanying schemes, as well as by reference to procedures known to those of ordinary skill in the art, including those described in PCT Publication WO 05/000809.

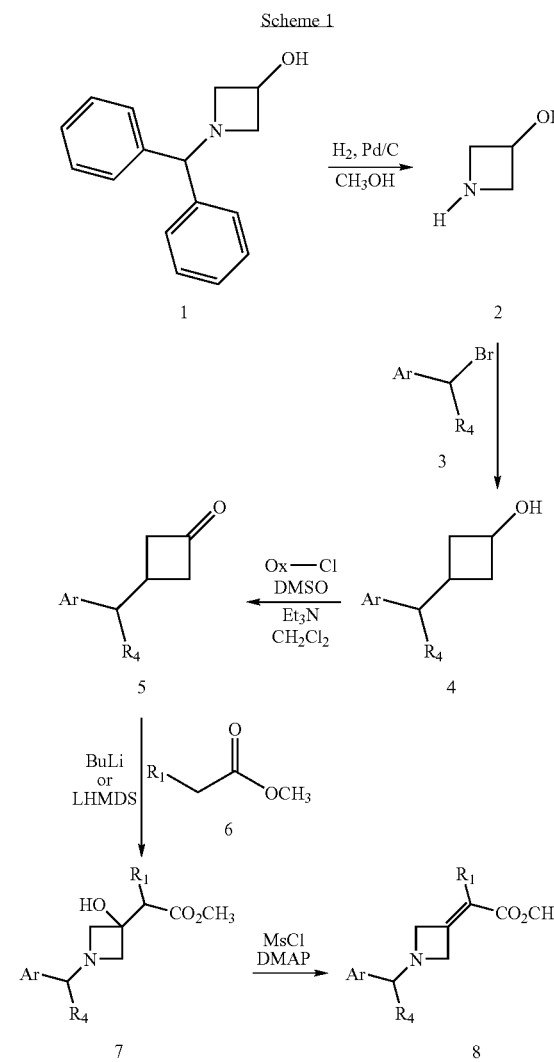

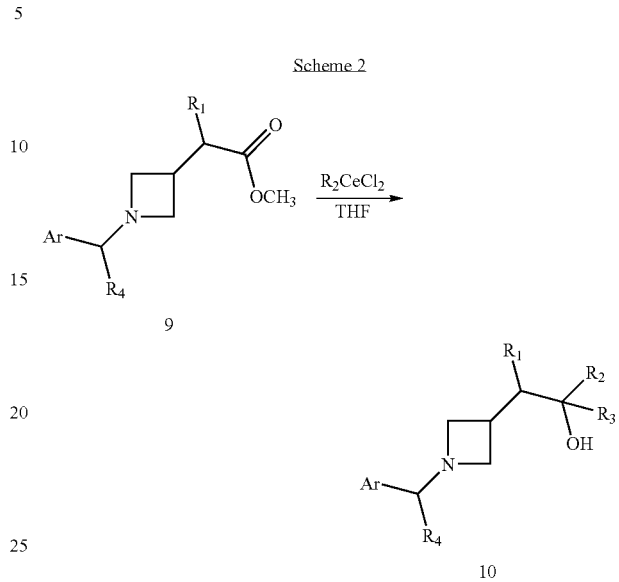

Scheme 2 illustrates the case where $R_2$ and $R_3$ are the same. Reaction of the carbonyl group of ester 9 with an excess of a carbanion such as Grignard reagent, alkyllithium reagent or an alkylcerium reagent in an aprotic solvent such as ether or THF at low temperatures affords the tertiary alcohol 10.

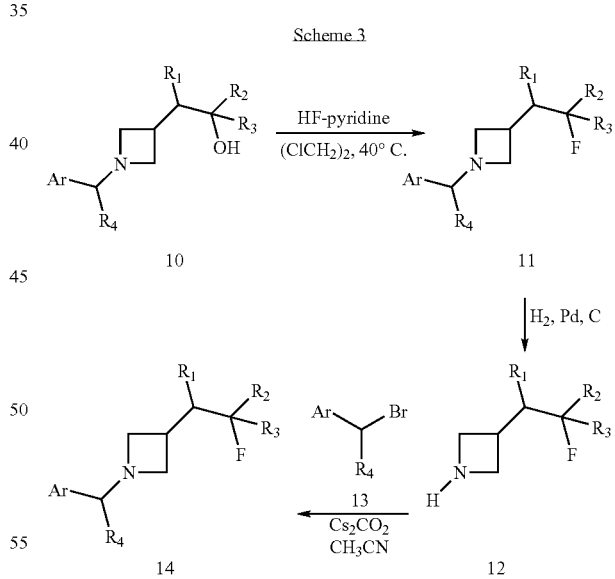

In Scheme 1, the starting material is the commercially available 1-(dimethylphenyl)-3-hyroxyazetidine (Oakwood Products, Inc.). The benzhydryl group of 1 is removed by catalytic hydrogenation in an alcoholic solvent using a palladium-charcoal catalyst and 50 psi hydrogen to afford the aminoalcohol 2. The amino group of 2 can be selectively alkylated with an appropriately substituted alkyl bromide 3 in the presence of a-base such as diisopropylethylamine in an aprotic solvent such as THF to afford 4. The hydroxy group of 4 can be oxidized under Swern conditions (oxalyl chloride, DMSO, $Et_3N$, $CH_2Cl_2$) to afford the appropriately substituted ketone 5. A ketene acetal is formed in situ by deprotonation of an appropriately substituted ester 6 with a strong base such as butyllithium or lithium hexamethyldisilamine in an aprotic solvent such as THF at −78° C. This ketene acetal adds to the carbonyl group of 5 to afford the hydroxy ester 7. Activation of the hydroxy group of 7 with methanesulfonyl chloride or methanesulfonic anhydride in the presence of a base such as DMAP or pyridine/DBU effects elimination to afford the olefin 8.

In Scheme 3, the hydroxyl group of compound 10 reacts under treatment with HF-pyridine complex in a solvent such as dichloroethane at 40° C. to form the corresponding fluoride 11. To change substitution on the azetidine nitrogen, the existing N-substituent may be removed by hydrogenation with a catalyst such as 10% Pd on charcoal to afford amine 12. In the latter case, the alkyl group may be replaced by alkylation with same or a differently substituted bromide 13 under conditions described in Scheme 3 to afford 14.

Scheme 4

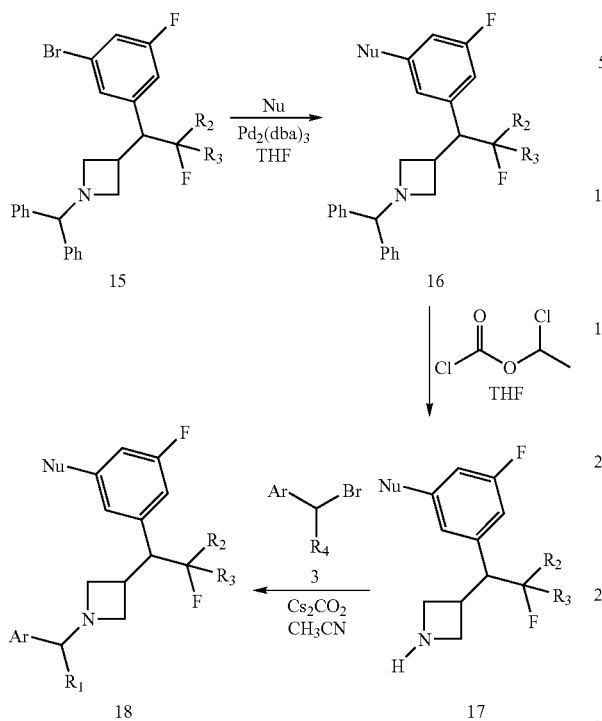

Scheme 5

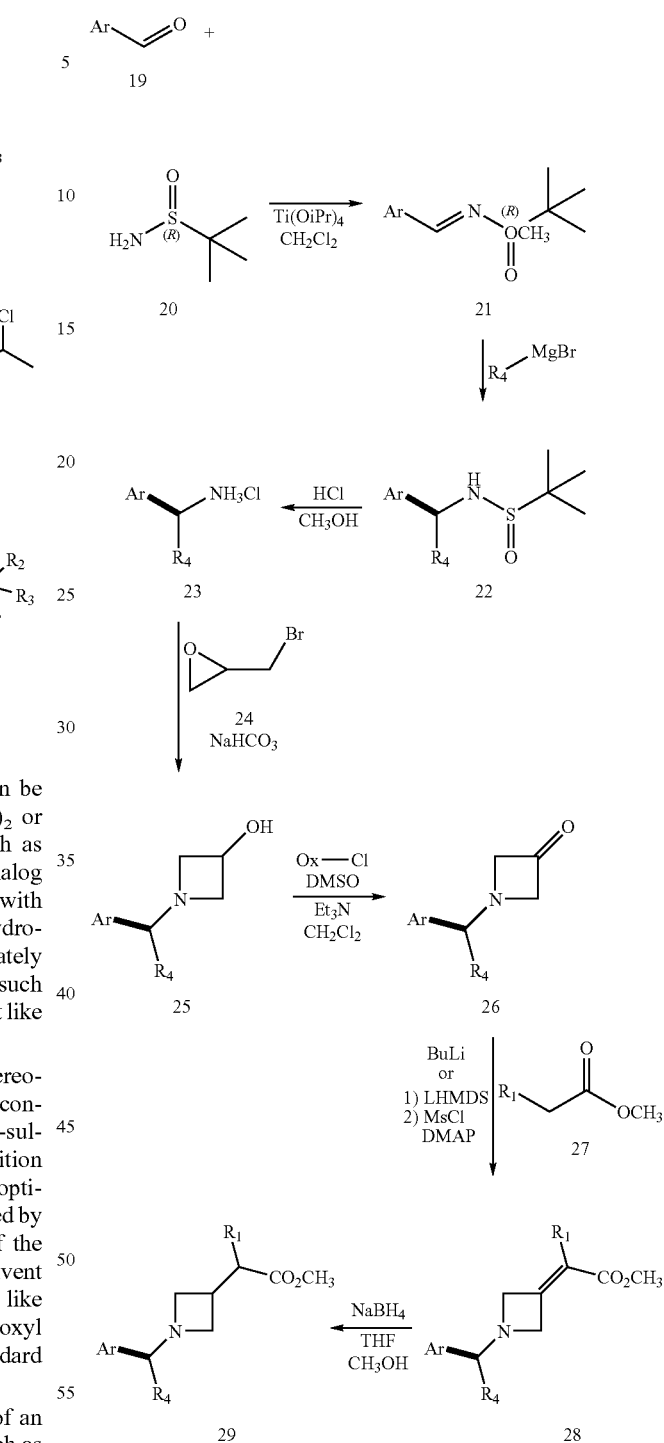

In Scheme 4, the bromo group of compound 15 can be selectively replaced by a nucleophile such as $Zn(CN)_2$ or LHMDS in the presence of a palladium catalyst such as $Pd_2(dba)_3$ to afford the corresponding aryl-substituted analog 16. The benzhydryl group of 50 is removed by treatment with 1-chloroethyl chloroformate in a solvent such as tetrahydrofuran and the resulting amine 17 reacts with an appropriately substituted alkyl bromide in the presence of a mild base such as diisopropylethylamine or $Cs_2CO_3$ in an aprotic solvent like $CH_3CN$ to afford 18.

In Scheme 5, the azetidine ketone can be prepared stereoselectively in a 5 step sequence. An aryl aldehyde 19 condenses with the optically active (R)-2-methylpropane-2-sulfinamide 20 to afford imine 21. Chelation-controlled addition of a carbanion (e.g. Grignard reagent) to 21 affords the optically active sulfonamide 22. The sulfinyl group is removed by acid-mediated solvolysis with methanol. Treatment of the amine 23 with a reagent such as epibromohydrin in an solvent such as isopropanol and in the presence of a weak base like NaHCO3 affords the azetidine alcohol 24. The hydroxyl group of 24 can be oxidized to the ketone 25 under standard Swern oxidation conditions.

A ketene acetal is formed in situ by deprotonation of an appropriately substituted ester 27 with a strong base such as butyllithium or lithium hexamethyldisilamine in an aprotic solvent such as THF at −78° C., As in Scheme 1, this ketene acetal adds to the carbonyl group of 26 to afford an intermediate hydroxy ester, whose hydroxyl group is activated in site with methanesulfonyl chloride or methanesulfonic anhydride in the presence of a base such as DMAP or pyridine/DBU effects elimination to afford the olefin 28. The olefin can be selectively reduced by conjugate addition of a hydride such as $NaBH_4$ in an alcoholic solvent mixture (e.g. THF-methanol) to afford the saturated ester, 29 as a mixture of diastereomers.

In Scheme 6, the diastereomers of 29 can be separated by silica gel chromatography. The undesired diastereomer can be epimerized in a 2-step procedure: Deprotonation with a strong base such as lithium hexamethyldisilamide in an aprotic solvent such as THF at low temperatures followed by protonation with an acid such as acetic acid. The resulting isomers can again be separated by silica gel chromatography.

Scheme 6

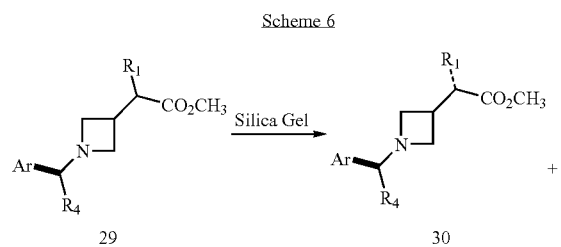

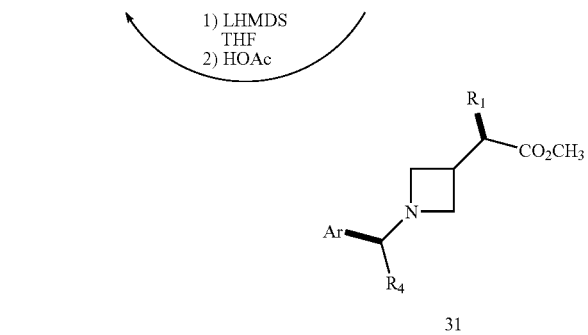

In Scheme 7, reaction of the ester 31 with an excess of a carbanion such as an alkyllithium or alkylcerium reagent in an aprotic solvent such as ether or THF at low temperatures affords the tertiary alcohol 32, where $R^2$ and $R^3$ are the same. The hydroxyl group of compound 32 reacts under treatment with HF-pyridine complex in a solvent such as dichloroethane at 40° C. to form the corresponding fluoride 33.

Scheme 7

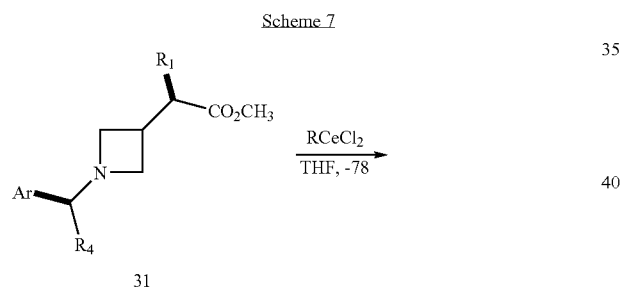

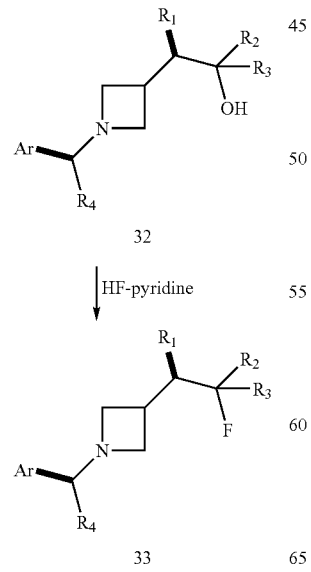

If the $R_1$, $R_4$ or Ar are aryl groups that contain a carboxy substituent or a group that can easily become a carboxy substituent (e.g. a nitrile or halogen), those substituents can be further modified to form heterocycles. For example, the nitrile of 34 can be hydrolyzed and esterified to form ester 35, which reacts with a nucleophile such as hydrazine to afford the hydrazide 36. Hydrazide 36 will react with reagents such as phosgene or carbonyl diimidazole to form the 5-oxo-4,5-dihydro-1,3,4-oxadiazole 37.

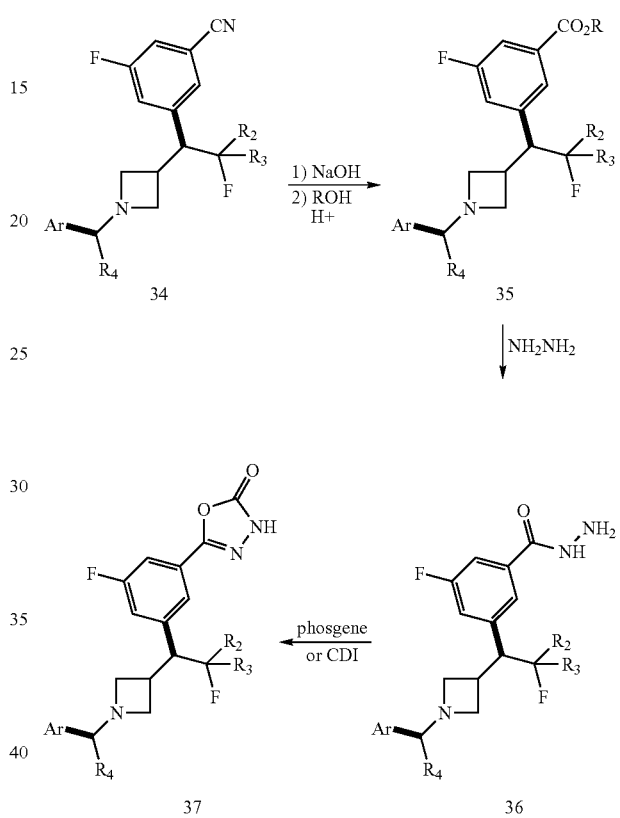

Treatment of hydrazide 36 with an orthoester such as triethyl orthoformate affords the 1,3,4-oxadizaole, 38.

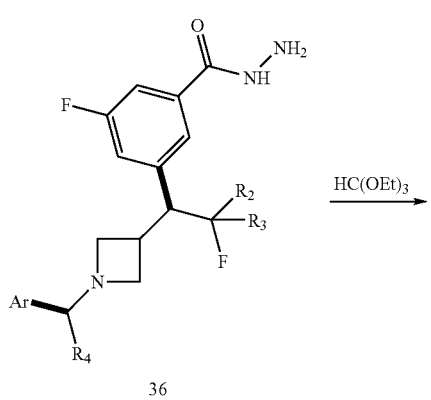

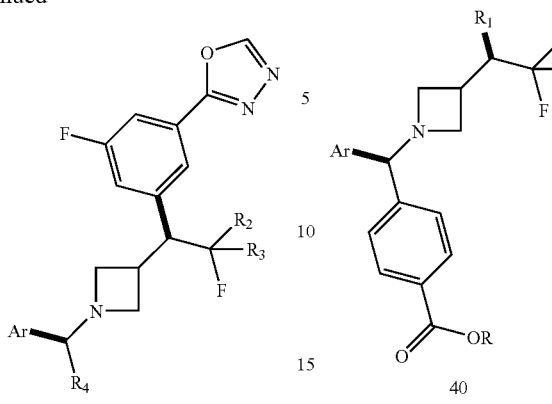

Treatment of hydrazide 36 with a reagent such as cyanogen bromide affords the 5-amino-1,3,4-oxadizaole, 39.

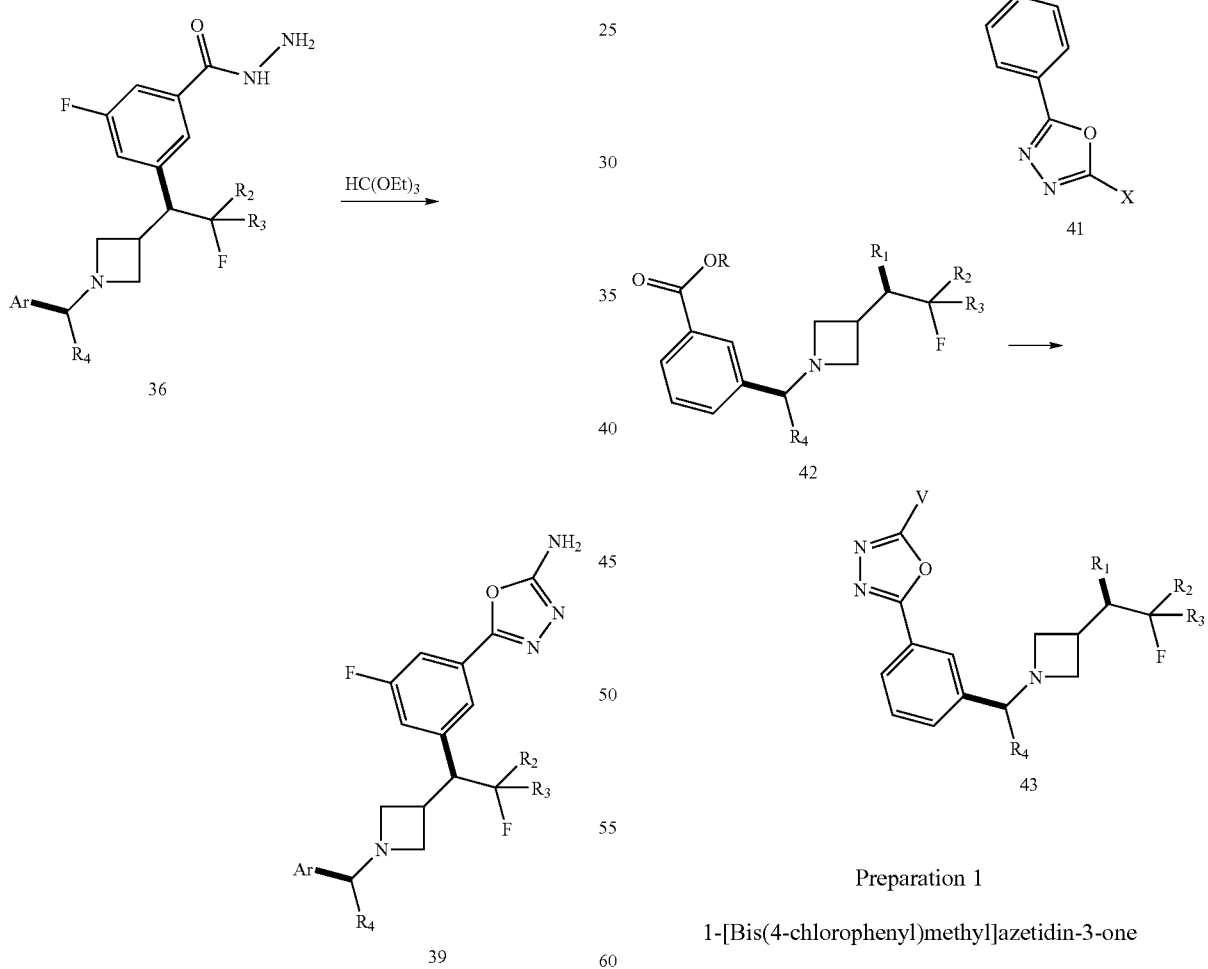

The same chemistry will work at the Ar and $R^4$ positions. For example, ester 40 would afford oxadizaole 41 and ester 42 would afford oxadizaole 43.

Preparation 1

1-[Bis(4-chlorophenyl)methyl]azetidin-3-one

This compound was prepared according to the procedures in WO 05/000809, Preparation 1.

Step 1: Azetidin-3-ol

A mixture of 15 g (62.76 mmol) of 1-benzhydrylazetan-3-ol and 3.5 g of palladium on activated carbon (10%) in 130 mL $CH_3OH$ was pressurized to 50 psi with hydrogen gas and shaken at room temperature for 48 h. After removal -of catalyst, the solution was concentrated to remove CH₃OH. The residue was washed with hexanes/ether (1/1) to afford the title compound; $^1$NMR(CD₃OD) δ 2.09 (s, 1H), 3.94 (m, 2H), 4.28 (m, 21H), 4.75 (m, 1H).

Step 2: 1-[Bromo(4-chlorophenyl)methyl]-4-chlorobenzene

To a solution of 15.14 g (59.3 mmol) of bis(4-chlorophenyl) CH₃OH in 100 mL of CH₂Cl₂ was added slowly a solution of 71.2 mL of BBr₃ (71.2 mmol, 1M in CH₂Cl₂). The solution was stirred for at 0° C. for 1 h. Then 60 mL of water was added to quench the reaction and the reaction mixture was poured into 200 mL of CH₂Cl₂. The water layer was extracted with CH₂Cl₂ (60 mL×2) and the combined organic layer was dried over Na₂SO₄ and concentrated to give the title compound; $^1$H-NMR(CDCl₃) δ 6.24 (s, 1H), 7.36 (d, 4H, J=8.7 Hz), 7.41 (d, 2H, J=8.7 Hz).

Step 3: 1-[Bis(4-chlorophenyl)methyl]azetidin-3-ol

The reaction mixture of 22.30 g (70.5 mmol) of 1-[bromo (4-chlorophenyl)methyl]-4-chlorobenzene, 5.67 g (77.6 mmol) of azetidin-3-ol (2) and 18.4 mL (105.75 mmol) of DIEA in 250 mL of acetonitrile was rapidly stirred for 1.5 h at rt to 91° C., Reaction mixture was concentrated to remove solvents and residue was purified by silica gel chromatography with hexanes/ethyl acetate/ammonia (2M in MeOH)=100/30/0.5 to afford the title compound; $^1$H-NMR(CDCl₃) δ 2.03 (br s, 1H), 2.81 (m, 2H), 3.55 (m, 2H), 4.34 (s, 1H), 4.50 (m, 1H), 7.29 (m, 4H), 7.34 (m, 4H).

Step 4: 1-[Bis(4-chlorophenyl)methyl]azetidin-3-one

To a solution of 6.3 mL (71.42 mmol) of oxalyl chloride in 250 mL of CH₂Cl₂ was added slowly 10.15 mL (142.84 mmol) of DMSO at −78° C. and stirred for 20 minutes. To this was added a solution of 11 g (35.7 mmol) of 1-[bis(4-chlorophenyl)methyl]azetidin-3-ol in 30 mL of CH₂Cl₂ and the mixture was stirred for 30 minutes at −78° C. Then 24.7 mL (178.56 mmol) of triethylamine was added at −78° C. and the mixture was stirred for 1 h at −78° C. before warming to rt. The solution was poured into 500 mL of ether and washed with 50 mL of aq NaHCO₃. The organic layer was dried over Na₂SO₄ and concentrated to afford the title compound.

Preparation 2

1-[bis(4-phenyl)methyl]azetidin-3-one

Prepared from 1-[Bis-phenylmethyl]azetidin-3-ol as described in Step 4 of Preparation 1; Mass Spectrum: m/e=238 (M+1).

Preparation 3

Methyl {1-[bis(4-chlorophenyl)methyl]azetidin-3-ylidene}(3,5-difluorophenyl)acetate Step 1: Methyl (3,5-difluorophenyl)acetate A solution of 5.0 g (29.1 mmol) of 3,5-difluorophenylacetic acid and a solution of 20 mL (80 mmol) of HCl in dioxane (4M) in 60 mL CH₃OH was heated at reflux for 6 h. After cooling, the solution was concentrated and the residue poured into 200 mL of ether/ethyl acetate (1/1). The organic layer was washed with 20 mL of water, dried over Na₂SO₄ and concentrated to afford the title compound.

Step 2: Methyl {1-[bis(4-chlorophenyl)methyl]-3-hydroxyazetidin-3-yl}(3,5-difluorophenyl) acetate A solution of 2 mL of 1.6M butyllithium in hexane and 2 mL of dry THF was cooled to −78° C. under nitrogen. To this was added a solution of 0.626 g (3.2 mmol) of methyl (3,5-difluorophenyl)acetate in 4 mL of THF and the solution was stirred at −78° C. After 20 min, a solution of 0.600 g (1.95 mmol) of 1-[bis(4-chlorophenyl)methyl]azetidin-3-one in 4 mL THF was added and the solution was stirred at −78° C. After 1 h, the reaction was quenched by addition of 10 mL of saturated NH₄CL solution and 20 mL of ether. The layers were separated and the aqueous layer was washed with ether. The combined organic layers were washed with brine, dried over magnesium sulfate and concentrated. The residue was filtered through a plug of silica gel using 25% ether-hexane to afford the title compound; $^1$H-NMR(CDCl₃) δ 2.91 (d, 1H J=8.3 Hz), 3.14 (d, 1H J=8.0 Hz), 3.17 (d, 2H, J=8.2Hz), 3.32 (d, 1H J=7.8 Hz), 3.74 (s, 3H), 4.03 (s, br, 1H), 4.42 (s, 1H), 4.42 (s, 1H), 6.76 (m, 1H), 6.6.89 (m, 2H), 7.33 (m, 4H), 7.38 (m, 4H); Mass Spectrum: m/e=492 (M+1 $^{35}$Cl, $^{35}$Cl) and 494 (M+1 $^{35}$Cl, $^{37}$Cl).

Step 3: Methyl {1-bis(4-chlorophenyl)methyl]azetidin-3-ylidene}(3,5-difluorophenyl)acetate A solution of 0.71 g (1.44 mmol) of methyl {1-[bis(4-chlorophenyl)methyl]-3-hydroxyazetidin-3-yl}(3,5-difluorophenyl)acetate, 0.295 g (1.73 mmol) of methanesulfonyl anhydride, and 0.400 mL pyridine in 5 mL of CH₂Cl₂ was stirred at room temperature overnight. To this was added 0.400 mL of diazabicycloundecane and the solution remained stirring at room temperature. The mixture was partitioned between ether and water and the aqueous layer was washed with 20 mL of ether. The organic layers were washed with brine, combined, dried over MgSO₄ and concentrated. The residue was filtered through a pad of silica gel using 20% ether-hexane to afford the title compound; $^1$H-NMR(CDCl₃) δ 3.67 (s, 3H), 3.84 (m, 2H), 4.25 (m, 2H), 4.54 (s, 1H), 6.76 (m, 1H), 6.78 (m, 2H), 7.33 (m, 4H), 7.38 (m, 4H); Mass Spectrum: m/e =474 (M+1 $^{35}$Cl, $^{35}$Cl) and 476 (M+1 $^{35}$Cl, $^{37}$Cl).

Preparation 4

Methyl {1-[bis(4-chlorophenyl)methyl]azetidin-3-ylidene}(3,5-difluorophenyl)acetate To a solution of 3.83 g (20.57 mmol) of methyl(3,5-difluorophenyl)acetate in 30 mL of THF was added a solution of 8.6 mL (21.51 mmol) of butyllithium (2.5M solution in hexanes) and stirred for 30 minutes at −78° C. A solution of 5.73 g (18.7 mmol) of 1-[bis(4-chlorophenyl)methyl]azetidin-3-one in 10 mL THF was added and the solution was stirred for 2 h at −78° C. Then 2.28 g (18.6 mmol) of 4-dimethylaminopyridine, 3.3 mL(1 8.7 mmol) of DIEA and 3.0 mL (37.4 mmol) of methanesulfonyl chloride was added and the solution was stirred for 1 h as it warmed from −78° C. to rt. The reaction mixture was then warmed to 45° C. and stirred for additional 2.5 h. The mixture was poured into 250 mL of ether and washed with 50 mL of aq NaHCO₃. The organic layer was dried over Na₂SO₄ and concentrated. The residue was purified by silica gel chromatography with hexanes/ethyl acetate=15:1 to afford the title compound; $^1$H-NMR (CDCl₃) δ 3.67 (s, 3H), 3.84 (m, 2H), 4.25 (m, 2H), 4.54 (s, 1H), 6.76 (m, 1H), 6.78 (m, 2H), 7.33 (m, 3H), 7.38 (m, 2H); Mass Spectrum: m/e=474 (M+1 $^{35}$Cl, $^{35}$Cl) and 476 (M+1 $^{35}$Cl, $^{37}$Cl).

Preparation 5

Methyl (3,5-difluorophenyl)[1-(diphenylmethyl)azetidin-3-ylidene]acetate

Prepared from 1-[bis(4-phenyl)methyl]azetidin-3-one (Preparation 2) by procedures described in Steps 1-3 of Preparation 3; Mass Spectrum: m/e=406 (M+1).

Preparation 6

Methyl {1-[bis(4-chlorophenyl)methyl]azetidin-3-yl}(3,5-difluorophenyl)acetate To a solution of 5.0 g (10.54 mmol) of methyl{1-[bis(4-chlorophenyl)methyl]azetidin-3-ylidene}(3,5-difluorophenyl)acetate in 60 mL of MeOH and 15 mL of $CH_2Cl_2$ was slowly added 798 mg (21.08 mmol) of $NaBH_4$. The solution was stirred for 5 h at 0° C., then poured into 250 mL of ether and washed with 50 mL of aq $NaHCO_3$. The organic layer was dried over $Na_2SO_4$ and concentrated. The residue was purified by silica gel chromatography with hexanes/ethyl acetate to afford the title compound; $^1$H-NMR($CDCl_3$) δ 2.68 (m, 1H), 2.92 (m, 1H), 3.10-3.15 (m, 2H), 3.44 (m, 1H), 3.69 (s, 3H), 3.86 (d, J=11 Hz, 1H), 4.30 (s, 1H), 6.74 (m, 1H), 6.85 (m, 2H), 7.24-7.34 (m, 8H); Mass Spectrum: m/e=476 (M+1 $^{35}$Cl, $^{35}$Cl) and 478 (M+1 $^{35}$Cl, $^{37}$Cl).

Preparation 7

2-{1-[Bis(4-chlorophenyl)methyl]azetidin-3-yl}(3,5-difluorophenyl)ethanol

To a solution of 1.47 g (3.09 mmol) of methyl{1-[bis(4-chlorophenyl)methyl]azetidin-3-yl}(3,5-difluorophenyl)acetate in 25 mL THF was added a solution of 3.1 mL (3.1 mmol) of $LiAlH_4$ (1M solution in THF). The solution was stirred for 10 minutes at 0° C. Then 4 g of sodium sulfate decahydrate was added to quench the reaction and the mixture was stirred for 1h at rt. The mixture was filtered and the organic layer was dried over $Na_2SO_4$ and concentrated to afford the title compound; $^1$H-NMR($CDCl_3$) δ 3.99 (s, 2H), 4.03 (s, 2H), 4.35 (s, 2H), 4.54 (s, 1H), 6.70-6.80 (m, 3H), 7.30-6-7.40(m, 8H); Mass Spectrum: m/e=446 (M+1 $^{35}$Cl, $^{35}$Cl) and 448 (M+1 $^{35}$Cl, $^{37}$Cl).

Preparation 8

{1-[Bis(4-chlorophenyl)methyl]azetidin-3-yl}(3,5-difluorophenyl)acetaldehyde To a solution of 0.92 mL (10.5 mmol) of oxalyl chloride in 60 mL of $CH_2Cl_2$ was added slowly 1.49 mL (20.96 mmol) of DMSO at –78° C. and stirred for 20 minutes. Then a solution of 2.35 g (5.24 mmol) of 2-{1-[bis(4-chlorophenyl) methyl] azetidin-3-yl}(3,5-difluorophenyl)ethanol in 10 mL of $CH_2Cl_2$ was added into above reaction mixture. The reaction mixture was stirred for 30 minutes at –78° C. Then 3.62 mL (26.2 mmol) of triethylamine was added at –78° C. and the mixture was stirred for 1 h at –78° C. to rt. This was poured into 200 mL of ether and washed with 30 mL of aq $NaHCO_3$. The organic layer was dried over $Na_2SO_4$ and concentrated to afford the title compound. $^1$H-NMR($CDCl_3$) δ 2.74 (m, 1H), 2.94 (m, 1H), 3.01 (m, 1H), 3.19 (m, 1H), 3.48 (m, 1H), 3.85 (d, J=10 Hz, 1H), 4.29 (s, 1H), 6.71-6.85 (m, 3H), 7.24-7.33 (m, 8H), 9.66 (s,1H); Mass Spectrum: m/e=446 (M+1 $^{35}$Cl, $^{35}$Cl) and 448 (M+1 $^{35}$Cl, 37Cl).

Preparation 9

3-[(S)-(4-Chlorophenyl)(3-hydroxyazetidin-1-yl)methyl]benzonitrile

This compound was prepared according to the procedures in WO 05/000809, Preparation 9.

Preparation 10

3-[(S)-(4-Chlorophenyl)(3-hydroxyazetidin-1-yl)methyl]benzonitrile, alternate preparation Step 1 N-[(1E)-(3-cyanophenyl)methylene]-2-methylpropane-2-(R)sulfinamide A solution of 19.0 g (157 mmole) of (R)-(+)-2-methylpropane-2-sulfinamide and 89.0 g (314 mmole) of titanium tetraisopropoxide in $CH_2Cl_2$ was stirred at room temperature for 10 min. Then a solution of 21.6 g (165 mmole) of 3-formylbenzonitrile in 10 mL $CH_2Cl_2$ was added, and the solution was stirred at room temperature. After 18 h, the reaction was quenched by the addition of 30 mL brine and the solution was rapidly stirred for 15 min. The mixture was filtered through a pad of CELITE and the residue was washed with 300 mL of $CH_2Cl_2$. The combined organic extracts were washed with brine, dried over $Na_2SO_4$ and concentrated. The residue was filtered through a pad of silica gel using 20% ethyl acetate-hexane to afford the title compound; $^1$H-NMR($CDCl_3$) δ 1.31 (s, 9H), 7.65 (t, 1H, J=7.8 Hz), 7.82 (d, 1H, J=7.8 Hz), 8.07 (d, 1H, J=7.8 Hz), 8.20 (s, 1H), 8.62 (s, 1H); Mass Spectrum: m/e=235 (M+1).

Step 2 N-[(S)-(4-chlorophenyl)(3-cyanophenyl)methyl]-2-methylpropane-2-(R)-sulfinamide A solution of 20 g (85.4 mmole) of N-[(1E)-(3-cyanophenyl)methylene]-2-methylpropane-2-(R)sulfonamide in 1000 mL toluene and 400 mL ether was cooled to –60° C. in a dry ice-acetone bath. Then 170 mL of a 1M solution of 4-chlorophenylmagnesium bromide in ether was added at a rate such that the temperature remained between –60° C. and –50° C. and the reaction was stirred at –60° C. for 6 h. The reaction was quenched by addition of 300 mL of saturated $NH_4Cl$ solution and the layers were separated. The organic layer was washed with 300 mL aliquots of saturated $NH_4Cl$ solution and brine, then was dried over $Na_2SO_4$ and concentrated. The residue was filtered through a pad of silica gel using 10 to 30% ethyl acetate hexane to afford the title compound with de >96% as determined by analytical ChiralPak AD column; $^1$H-NMR($CDCl_3$) δ 1.27 (s, 9H), 3.76 (s, 1H), 5.65 (d, 1H, J=2.3 Hz), 7.24-7.7 (m, 8H).

Step 3 3-[(S)-amino(4-chlorophenyl)methyl]benzonitrile hydrochloride

To a solution of 850 mg (2.45 mmole) of N-[(S)-(4-chlorophenyl)(3-cyanophenyl)methyl]-2-methylpropane-2-(R)-sulfinamide in 20 mL of $CH_3OH$ was added 2.5 mL of 4M HCL in dioxane. The solution was stirred at room temperature for 45 min, then was diluted with 40 mL ether. The solids were collected by filtration to afford the title compound as a white solid; $^1$H-NMR($CDCl_3$) δ 1.6 (s, 2H, br), 5.24 (s, 1H), 7.24-7.78 (m, 8H).

Step 4 3-[(S)-(4-chlorophenyl)(3-hydroxyazetidin-1-yl)methyl]benzonitrile

To a mixture of 20.27 g (72.6 mmole) of 3-[(S)-[(3-chloro-2-hydroxypropyl)amino](4-chlorophenyl)methyl]benzonitrile hydrochloride and 21.3 g (245 mmole) of $NaHCO_3$ in 600 mL of isopropanol was added 14.4 mL (174 mmole) of epibromohydrin . The mixture was heated to reflux for 24 h, then was cooled and concentrated. The residue was partitioned between 750 mL portions of ether and water and the aqueous layer was washed with two 500 mL portions of ether. The combined organic extracts were washed with brine, dried over $MgSO_4$ and concentrated. The residue was purified by flash chromatography using 10-20% ethyl acetate in hexane to afford the title compound as a clear oil; $^1$H-NMR($CDCl_3$) δ 1.6 (s, 2H, br), 5.24 (s, 1H), 7.24-7.78 (m, 8H).2.89 (m, 2H), 3.54 (m, 2H), 4.39 (s, 1H), 4.52 (m, 1H), 7.2-7.8 (m, 8H).

Preparation 11

1-{1-[(3-chlorophenyl)(4-chlorophenyl)methyl]azetidin-3-yl}-1-(3 5-difluorophenyl)-2-methylpropan-2-ol A solution of 0.985 g (4.0 mmole) of finely powdered CeCl$_3$ (Strem Chemical Co.) in 10 mL anhydrous THF was stirred at room temperature under N$_2$. After 1 h, the solution was cooled to −78° C. in a dry ice-acetone bath and 2.5 mL of a 1.6M solution of methyllithium in ether was added dropwise at such a rate that the solids remained dispersed. After 30 minutes, a solution of 0.485 g (1.1 mmole) of methyl {1-[(3-chlorophenyl)(4-chlorophenyl)methyl]azetidin-3-yl}(3,5-difluorophenyl)acetate in 5 mL of THF was added and the solution was left stirring at −78° C. for 1 h. The reaction was quenched by addition of 0.1 mL CH$_3$OH, diluted with 40 mL of ether and allowed to warm to −10° C. Then aqueous NH$_4$Cl solution was added dropwise until the cerium salts precipitated onto the surface of the flask. The supernatant was decanted and the solids were triturated with two 20 mL portions of CH$_2$Cl$_2$ and two 20 mL portions of ether. The combined organic extracts were washed with saturated aqueous NH$_4$Cl solution and brine, dried over Na$_2$SO$_4$ and concentrated to afford the title compound as a mixture of 4 diastereomers. The mixture was purified by flash chromatography on silica gel using a step gradient of 3 column volumenes each of 1%, then 2%, then 4%, then 6% ethyl acetate-hexane to afford two diastereomers of the title compound. The enantiomers of the faster diastereomer were separated by chromatography on an AD column chiral using 6% isopropanol in heptane. Faster diastereomer: $^1$H-NMR(CDCl$_3$) δ 1.07 (s, 3H), 1.14 (S, 3H), 2.28 (t, 1H, J=7.5Hz), 2.74 (d, 1H, J=10.7 Hz), 2.82 (t, 1H, J=7.5 Hz), 3.10-3.16 (m, 2H), 3.62 (in, 1H), 4.20 (s, 1H), 6.67-6.73 (m, 3H), 7.21-7.33(m, 8H); Mass Spectrum: m/e=476 (M+1 $^{35}$Cl, $^{35}$Cl) and 478 (M+1$^{35}$Cl, $^{37}$Cl). Slower diastereomer $^1$H-NMR(CDCl$_3$) δ 1.06 (s, 3H), 1.14 (S, 3H), 2.29 (t, 1H, J=7.5 Hz), 2.75 (d, 1H, J=10.7 Hz), 2.82 (t, 1H, J=7.5 Hz), 3.10-3.16 (m, 2H), 3.62 (m, 1H), 4.22 (s, 1H), 6.67-6.73 (m, 3H), 7.21-7.33(m, 8H); Mass Spectrum: m/e=476 (M+1 $^{35}$Cl, $^{35}$Cl) and 478 (M+1 $^{35}$Cl, $^{37}$Cl).

Preparation 12

3-((S)-(4-chlorophenyl){3-[(1S)-1-(3,5-difluorophenyl)-2-hydroxy-2-methylpropyl]azetidin-1-yl}methyl)benzonitrile Step 1: (1S)-1-(3,5-difluorophenyl)-1-[1-(diphenylmethyl)azetidin-3-yl]-2-methylpropan-2-ol
A suspension of 67.03 g (272 mmole) of CeCl$_3$ in 500 mL dry THF was stirred in a 2L three-necked flask under N$_2$ at rt. After 30 minutes, the mixture was cooled to −78° C. in a dry ice-acetone bath and 155 mL of a 1.6M solution of methyllithium in ether was added dropwise with vigorous stirring. The yellow-green mixture was stirred at −78° C. for an additional 30 minutes and then a solution of 28.75 g (70.6 mmole) of methyl (3,5-difluorophenyl)[1-(diphenylmethyl)azetidin-3-yl]acetate in 100 mL of dry THF was added over 30 minutes, at such a rate as to keep the temperature below −60° C. The mixture was left stirring at −78° C. for 1 h, then excess carbanion was decomposed by the dropwise addition of 20 mL CH$_3$OH and 1000 mL ether while the solution warmed to −40° C. The reaction was quenched by addition of saturated aqueous NH$_4$Cl until the most of the solids had precipitated to the bottom surface of the flask. The liquid layer was decanted into a 2L separatory funnel and the solids were triturated with three 200 mL portions of CH$_2$Cl$_2$. The combined organic layers were washed with two 400 mL portions of aqueous NH$_4$Cl solution and brine, then dried over Na$_2$SO$_4$ and concentrated to a white solid. The residue was purified on Chiral-Pak AD resin using 5% isopropanol-heptane. Fractions containing the faster enantiomer were pooled and concentrated to afford the title compound, which is the (+) enantiomer; $^1$H-NMR(CDCl$_3$) δ 1.07 (s, 3H), 1.14 (S, 3H), 2.28 (t, 1H, J=7.5 Hz), 2.74 (d, 1H, J=10.7 Hz), 2.82 (t, 1H, J=7.5 Hz), 3.10-3.16 (m, 2H), 3.62 (m, 1H), 4.20 (s, 1H), 6.67-6.73 (m, 3H), 7.21-7.45 (m, 10H); Mass Spectrum: m/e=408.

Step 2: (1 S)-1-azetidin-3-yl-1-(3,5-difluorophenyl)-2-methylpropan-2-ol
A 500 mL Parr flask was purged with N$_2$ and charged with 1.2 g of 10% Pd/C and 20 mL of CH$_3$OH. To this was added a solution of 4.1 g (10.1 mmole) of (1S)-1-(3,5-difluorophenyl)-1-[1-(diphenylmethyl)azetidin-3-yl]-2-methylpropan-2-ol and the mixture was shaken under 40 psi H$_2$ for 24 h. The mixture was filtered through CELITE and the filtrate was concentrated. The oily residue was applied to a silica gel column packed in 20% ethyl acetate-hexane, and the column was washed with 5 column volumes of 20% ethyl acetate-hexane, then with CH$_2$Cl$_2$, with 10% CH$_3$OH in CH$_2$Cl$_2$ and finally with 60:40:10 CH$_2$Cl$_2$—CH$_3$OH-ammonium hydroxide. Homogenous fractions were concentrated to afford the title compound, which was not further purified but was used directly in the next step; Mass Spectrum: m/e=244 (M+1).

Step 3: 3-((S)-(4-chlorophenyl){3-[(1S)-1-(3,5-difluorophenyl)-2-hydroxy-2-methylpropyl]azetidin-1-yl}methyl)benzonitrile A solution of the crude amine from Step 3 and 6.51 g (20 mmole) of Cs$_2$CO$_3$ in 30 mL dry acetonitrile was stirred at rt in a flask fitted with a small Dean-Stark trap. After 15 minutes, 4.6 g (15 mmole) 3-[bromo(4-chlorophenyl)methyl] benzonitrile was added and the mixture was heated at 60° C. After 18 h, the solution was filtered through CELITE and the residue was washed with acetonitrile. The combined filtrates were concentrated and the residue was purified by flash chromatography using a step gradient of 5 to 20 % ethyl acetate-hexane. Fractions containing the faster product diastereomer were pooled and concentrated to afford the title compound; $^1$H-NMR (CDCl$_3$) δ 1.07 (s, 3H), 1.14 (S, 3H), 2.28 (t, 1H, J=7.5 Hz), 2.74 (d, 1H, J=10.7 Hz), 2.82 (t, 1H, J=7.5 Hz), 3.10-3.16 (m, 2H), 3.62 (m, 1H), 4.29 (s, 1H), 6.67-6.73 (m, 3H), 7.21-7.4 (m, 8H); Mass Spectrum: m/e=469 (M+1, $^{35}$Cl) and 471 (M+1, $^{37}$Cl).

Preparation 13

3-((S)-(4-chlorophenyl){3-[(1S)-1-(3,5-difluorophenyl)-2-fluoro-2-methylpropyl]azetidin-1-yl}methyl) benzonitrile This compound was prepared according to the procedures of WO 05/00809, Example 75.

Preparation 14

3-((S)-(4-chlorophenyl){3-[(1S)-1-(3,5-difluorophenyl)-2-hydroxy-2-methylpropyl]azetidin-1-yl}methyl)benzonitrile Step 1: (1S)-1-(3,5-difluorophenyl)-1-[1-(diphenylmethyl)azetidin-3-yl]-2-methylpropan-2-ol
A suspension of 67.03 g (272 mmole) of CeCl$_3$ in 500 mL dry THF was stirred in a 2L three-necked flask under N2 at rt. After 30 minutes, the mixture was cooled to −78° C. in a dry ice-acetone bath and 155 mL of a 1.6M solution of methyllithium in ether was added dropwise with vigorous stirring. The yellow-green mixture was stirred at −78° C. for an additional 30 minutes and then a solution of 28.75 g (70.6 mmole) of methyl (3,5-difluorophenyl)[1-(diphenylmethyl) azetidin-3-yl]acetate in 100 mL of dry THF was added over 30 minutes, at such a rate as to keep the temperature below −60° C. The mixture was left stirring at −78° C. for 1 h, then excess carbanion was decomposed by the dropwise addition of 20 mL $CH_3OH$ and 1000 mL of ether while the solution warmed to −40° C. The reaction was quenched by addition of saturated aqueous $NH_4Cl$ until the most of the solids had precipitated to the bottom surface of the flask. The liquid layer was decanted into a 2L separatory funnel and the solids were triturated with three 200 mL portions of $CH_2Cl_2$. The combined organic layers were washed with two 400 mL portions of aqueous $NH_4Cl$ solution and brine, then dried over $Na_2SO_4$ and concentrated to a white solid. The residue was purified on ChiralPak AD resin using 5% isopropanol-heptane. Fractions containing the faster enantiomer were pooled and concentrated to afford the title compound, which is the (+) enantiomer; $^1$H-NMR(CDCl$_3$) δ 1.07 (s, 3H), 1.14 (S, 3H), 2.28 (t, 1H, J=7.5 Hz), 2.74 (d, 1H, J=10.7 Hz), 2.82 (t, 1H, J=7.5 Hz), 3.10-3.16 (m, 2H), 3.62 (m, 1H), 4.20 (s, 1H), 6.67-6.73 (m, 3H), 7.21-7.45 (m, 10H); Mass Spectrum: m/e=408.

Step 2: 3-[(1S)-1-(3,5-difluorophenyl)-2-fluoro-2-methylpropyl]-1-(diphenylmethyl)azetidine To a solution of 5.5 g (13.5 mmole) of (1S)-1-(3,5-difluorophenyl)-1-[1-(diphenylmethyl) azetidin-3-yl]-2-methylpropan-2-ol in 25 mL of $CH_2Cl_2$ was added 15 mL of hydrogen fluoride-pyridine and the two-phase mixture was stirred for 15 h at 42° C. Then the reaction mixture was poured to 100 mL of 5N NaOH, 20 mL of aq NaHCO$_3$, 150 mL of $CH_2Cl_2$ and 100 mL ice. The pH was adjusted to 8-9 with 2N NaOH. The water layer was extracted with $CH_2Cl_2$ (3×1500 mL). The combined organic layer was dried over $Na_2SO_4$ and concentrated. The residue was purified by silica gel chromatography with 10% methyl tert-butyl ether-hexane to afford the title compound as a white solid; $^1$H-NMR (CDCl$_3$) δ 1.25 (t, J=22 Hz, 6H), 2.33 (t, J=6.5 Hz, 1H), 2.83-2.89 (m, 2H), 3.09-3.11 (m, 2H), 3.60 (m, 1H), 4.30 (s, 1H), 6.68-6.71 (m, 3H), 7.21-7.8 (m, 10H); Mass Spectrum: m/e=410 (M+1)

Step 3: 3-[(1S)-1-(3,5-difluorophenyl)-2-fluoro-2-methylpropyl]azetidine

A 500 mL Parr flask was purged with N$_2$ and charged with 1.2 g of 10% Pd/C and 20 mL $CH_3OH$. To this was added a solution of 4.1 g (10.1 mmole) of 3-[(1S)-1-(3,5-difluorophenyl)-2-fluoro-2-methylpropyl]-1-(diphenylmethyl)azetidine and the mixture was shaken under 40 psi H$_2$ for 24 h. The mixture was filtered through CELITE and the filtrate was concentrated. The oily residue was applied to a silica gel column packed in 20% ethyl acetate-hexane and the column was washed with 5 column volumes of 20% ethyl acetate-hexane, then with $CH_2Cl_2$, with 10% $CH_3OH$ in $CH_2Cl_2$ and finally with 80:20:2 $CH_2Cl_2$—$CH_3OH$-ammonium hydroxide. Homogenous fractions were concentrated to afford the title compound, which was not further purified but was used directly in the next step; Mass Spectrum: m/e=244 (M+1).

Step 4: 3-((S)-(4-chlorophenyl){3-[(1S)-1-(3,5-difluorophenyl)-2-fluoro-2-methylpropyl]azetidin-1-yl}methyl)benzonitrile A solution of the crude amine from Step 3 and 6.51 g (20 mmole) of $Cs_2CO_3$ in 30 mL dry acetonitrile was stirred at rt in a flask fitted with a small Dean-Stark trap. After 15 minutes, 4.6 g (15 mmole) of 3-[bromo(4-chlorophenyl)methyl] benzonitrile was added and the mixture was heated at 60° C. After 18 h, the solution was filtered through CELITE and the residue was washed with acetonitrile. The combined filtrates were concentrated and the residue was purified by flash chromatography using a step gradient of 5 to 20 % ethyl acetate-hexane. Fractions containing the faster product diastereomer were pooled and concentrated to afford the title compound; $^1$H-NMR(CDCl$_3$) δ 1.25 (t, J=22 Hz, 6H), 2.33 (t, J=6.5 Hz, 1H), 2.83-2.89 (m, 2H), 3.09-3.11 (m, 2H), 3.60 (m, 1H), 4.24 (s, 1H), 6.68-6.71 (m, 3H), 7.21-7.8 (m, 8H); Mass Spectrum: m/e=469 (M+1, $^{35}$Cl) and 471 (M+1, $^{37}$Cl).

Preparation 15

3-((S)-(4-chlorophenyl){3-[(1s)-1-(3,5-difluorophenyl)-2-hydroxy-2-methylpropyl]azetidin-1-yl}methyl)benzonitrile Step 1: 3-[(1S)-1-(3,5-difluorophenyl)-2-fluoro-2-methylpropyl]azetidine A sample of 2.25 g (5.5 mmol) of 3-[(1S)-1-(3,5-difluorophenyl)-2-fluoro-2-methylpropyl]-1-(diphenylmethyl) azetidine(Step 2 of Preparation 14) was dissolved in 15 mL of THF and 1.1 mL (10 mmole) of 1-chloroethyl chloroformate was added. The solution was stirred at room temperature. After 2 h, the solution was concentrated under reduced pressure and the residue was dried under high vacuum for 1 h. The residue was dissolved in 20 mL of $CH_3OH$ and heated to reflux for 6 h. The solution was concentrated and the residue was partitioned between 100 mL ether and 50 mL of 1:1 saturated $Na_2CO_3$ solution-1M NaOH. The aqueous layer was washed with 3 portions of 100 mL ether, and the combined organic extracts were washed with $NaHCO_3$, then brine, then concentrated. The oily residue was applied to a silica gel column packed in 20% ethyl acetate-hexane and the column was washed with 5 column volumes of 20% ethyl acetate-hexane, then with $CH_2Cl_2$, with 10% $CH_3OH$ in $CH_2Cl_2$ and finally with 80:20:2 $CH_2Cl_2$—$CH_3OH$-ammonium hydroxide. Homogenous fractions were concentrated to afford the title compound, which was not further purified but was used directly in the next step; Mass Spectrum: m/e=244 (M+1).

Step 2: 3-((S)-(4-chlorophenyl){3-[(1S)-1-(3,5-difluorophenyl)-2-fluoro-2-methylpropyl]azetidin -1-yl}methyl)benzonitrile A solution of the crude amine from Step 1 and 3.4 g (1.1 mmole) of $Cs_2CO_3$ in 10 mL dry acetonitrile was stirred at rt in a flask fitted with a small Dean-Stark trap. After 15 minutes, 2.3 g (7.5 mmole) of 3-[bromo(4-chlorophenyl)methyl] benzonitrile was added and the mixture was heated at 60° C. After 18 h, the solution was filtered through CELITE, and the residue was washed with acetonitrile. The combined filtrates were concentrated and the residue was purified by flash chromatography using a step gradient of 5 to 20 % ethyl acetate-hexane. Fractions containing the faster product diastereomer were pooled and concentrated to afford the title compound; $^1$H-NMR(CDCl$_3$) δ 1.25 (t, J=22 Hz, 6H), 2.33 (t, J=6.5 Hz, 1H1), 2.83-2.89 (m, 2H), 3.09-3.11 (m, 2H), 3.60 (m, 1H1), 4.24 (s, 1H), 6.68-6.71 (m, 3H), 7.21-7.8 (m, 8H); Mass Spectrum: mi/e=469 (M+1, $^{35}$Cl) and 471 (M+1, $^{37}$Cl).

Preparation 16

3-((1S)-1-{1-[(S)-(4-chlorophenyl)(3-cyanophenyl) methyl]azetidin-3-yl}-2-fluoro-2-methylpropyl)-5-fluorobenzonitrile Step 1: Ethyl (2R)-(3-bromo-5-fluorophenyl)[1-(diphenylmethyl)-3-hydroxyazetidin-3-yl]acetate The title compound was prepared from ethyl 3-bromo-5-fluorophenylacetate and 1-[bis-phenylmethyl]azetidin-3-one (Preparation 2) by the procedure described in Step 2 of Preparation 3 except that lithium hexamethyldisilamide was used instead of butyllithium to form the ketene acetal; Mass Spectrum: m/e=498 (M+1, $^{79}$Br), 500 (M+1, $^{81}$Br)

Step 2: Ethyl (3-bromo-5-fluorophenyl)[1-(diphenylmethyl)azetidin-3-ylidene]acetate The title compound was prepared from ethyl (2R)-(3-bromo-5-fluorophenyl)[1-(diphenylmethyl)-3-hydroxyazetidin-3-yl]acetate according to the procedures described in Preparation 5; Mass Spectrum: m/e=480 (M+1, $^{79}$Br), 482 (M+1, $^{81}$Br)

Step 3 Ethyl (3-bromo-5-fluorophenyl)[1-(diphenylmethyl)azetidin-3-yl]acetate

The title compound was prepared from ethyl (3-bromo-5-fluorophenyl)[1-(diphenylmethyl) azetidin-3-ylidene]acetate according to the procedure described in Preparation 6 except that THF was used as the co-solvent; Mass Spectrum: m/e=482 (M+1, $^{79}$Br), 484 (M+1, $^{81}$Br).

Step 4 1-(3-Bromo-5-fluorophenyl)-1-[1-(diphenylmethyl)azetidin-3-yl]-2-methylpropan-2-ol The title compound was prepared from ethyl (3-bromo-5-fluorophenyl)[1-(diphenylmethyl) azetidin-3-yl]acetate according to the procedure described in Step 1 of Preparation 12; Mass Spectrum: m/e=468 (M+1, $^{79}$Br), 470 (M+1, $^{81}$Br).

Step 5 (1S)-1-(3-bromo-5-fluorophenyl)-1-[1-(diphenylmethyl)azetidin-3-yl]-2-methylpropan-2-ol The enantiomers of the product of Step 4 were separated by chromatography on a ChiralPak AD column using 3% isopropanol-heptane as described in Step 1 of Preparation 12; Mass Spectrum: m/e=468 (M+1).

Step 6 3-[(1S)-1-(3-bromo-5-fluorophenyl)-2-fluoro-2-methylpropyl]-1-(diphenylmethyl)azetidine The title compound was prepared from (1S)-1-(3-bromo-5-fluorophenyl)-1-[1-(diphenylmethyl) azetidin-3-yl]-2-methylpropan-2-ol according to the procedure described in Step 2 of Preparation 14; Mass Spectrum: m/e=470 (M+1, $^{79}$Br), 472 (M+1, $^{81}$Br).

Step 7 3-[(1S)-1-(3-bromo-5-fluorophenyl)-2-fluoro-2-methylpropyl]azetidine

The title compound was prepared from 3-[(1S)-1-(3-bromo-5-fluorophenyl)-2-fluoro-2-methylpropyl]-1-(diphenylmethyl)azetidine according to the procedure described in Step 1 of Preparation 15; Mass Spectrum: m/e=304 (M+1, $^{79}$Br), 306 (M+1, $^{81}$Br).

Step 8 3-[(S)-{3-[(1S)-1-(3-Bromo-5-fluorophenyl)-2-fluoro-2-methylpropyl]azetidin-1-yl}(4-chlorophenyl)methyl]benzonitrile The title compound was prepared from 3-[(1S)-1-(3-bromo-5-fluorophenyl)-2-fluoro-2-methylpropyl]azetidine according to the procedure described in Step 2 of Preparation 15 except that DIEA was used instead of $Cs_2CO_3$; Mass Spectrum: m/e=529 (M+1, $^{35}$Cl, $^{79}$Br), 531 (M+1, $^{35}$Cl, $^{81}$Br and $^{37}$Cl, $^{79}$Br), 576 (M+1, $^{35}$Cl, $^{81}$Br).

Step 9 3-((1S)-1-{1-[(S)-(4-chlorophenyl)(3-cyanophenyl)methyl]azetidin-3-yl}-2-fluoro-2-methylpropyl)-5-fluorobenzonitrile A suspension of 143 mg (0.27 mmole) of 3-[(S)-{3-[(1S)-1-(3-bromo-5-fluorophenyl)-2-fluoro-2-methylpropyl]azetidin-1-yl}(4-chlorophenyl)methyl]benzonitrile, 0.026 mg (0.216 mmole) of Zn(CN)2, 5 mg (0.005 mmole) of tris(dibenzylideneacetone)dipalladium(0) and 8 mg (0.014 mmole) of 1,1'-Bis(diphenylphosphino)ferrocene in 2.5 mL of dry DMF was degassed for 1 h at rt. Then the solution was heated at 140° C. for 17 h. The solution was concentrated under high vacuum and then was partitioned between 20 mL ether, 20 mL ethyl acetate and 10 mL water. The layers were separated and the aqueous layer was washed with two 20 mL portions of 1:1 ether-ethyl acetate. The combined organic layers were dried over $Na_2SO_4$ and concentrated. The residue was purified by preparatory TLC using 20% ethyl acetate-hexane to afford the title compound; Mass Spectrum: m/e=476 (M+1, 35Cl), 478 (M+1, $^{37}$Cl).

Preparation 17

Ethyl 3-(1-{1-[(4-chlorophenyl)(3-cyanophenyl)methyl]azetidin-3-yl}-2-fluoro-2-methylpropyl)-5-fluorobenzoate Step 1: 3-{1-[1-(diphenylmethyl)azetidin-3-yl]-2-fluoro-2-methylpropyl}-5-fluorobenzonitrile A solution of 16.19 g (34.42 mmol) of 3-[1-(3-bromo-5-fluorophenyl)-2-fluoro-2-methylpropyl]-1-(diphenylmethyl)azetidine, 3.23 g (27.53 mmol) of zinc cyanide, 1.10 g (1.2 mmol) of tris(dibenzylideneacetone)dipalladium, and 1.53 g (2.75 mmol) of DPPF in 99 mL of DMF and 1 mL of water was degassed for 1 h at rt. Then it was stirred at 140° C. After 17 h, it was concentrated to remove solvents. Then the mixture was poured into 300 mL of ether/ethyl acetate (1:1) and 100 mL aq $NaHCO_3$. The organic layer was dried over $Na_2SO_4$ and concentrated. The residue was purified by silica gel chromatography with hexanes/ethyl acetate to afford the title compound as a white solid; $^1$H-NMR(CDCl$_3$) δ 1.22(d, 3H, J=21 Hz), 1.30(d, 6H, J=21 Hz), 2.30 (t, 1H, J=7.8 Hz), 2.86-2.96 (m, 2H), 3.08-3.18 (m, 2H), 3.65 (t, 1H, J=7 Hz), 4.25 (s, 1H), 7.13-7.43 (m, 13H); Mass Spectrum: m/e=417 (M+1).

Step 2: 3-{1-[1-(diphenylmethyl)azetidin-3-yl]-2-fluoro-2-methylpropyl}-5-fluorobenzoic acid The reaction of mixture of 7.15 g (17.18 mmol) of 3-{1-[1(diphenylmethyl)azetidin-3-yl]-2-fluoro-2-methylpropyl}-5-fluorobenzonitrile (Step 1), 125 mL of EtOH, and 70 mL of 5N NaOH was refluxed for 3.5 h. Then it was adjusted to pH=4-5 with 12N HCl and concentrated to remove solvents. To the residue was added 200 mL of $CH_2Cl_2$ to dissolve the compound and it was filtered to remove the solid. The solid layer was washed with $CH_2Cl_2$ and the combined organic layers were concentrated to afford the title compound as white solid; Mass Spectrum: m/e=436 (M+1).

Step 3: Ethyl 3-{1-[1-(diphenylmethyl)azetidin-3-yl]-2-fluoro-2-methylpropyl}-5-fluorobenzoate A mixture of 7.5 g (17.15 mmol) of 3-{1-[1-(diphenylmethyl)azetidin-3-yl]-2-fluoro-2-methylpropyl}-5-fluorobenzoic acid, 25 mL of 4N HCl in dioxane, and 200 mL of EtOH was refluxed. After 10 h, it was concentrated to remove solvents. To the residue was added 150 mL of $CH_2Cl_2$ and 30 mL of H2O and pH was adjusted to 7-8 with aq $NaHCO_3$, then extracted with $CH_2Cl_2$. The combined organic layer was dried over $Na_2SO_4$ and concentrated. The residue was purified by silica gel chromatography with hexanes/ethyl acetate to afford the title compound as an white solid; $^1$H-NMR (CDCl$_3$) δ 1.25(d, 3H, J=22 Hz), 1.30(d, 3H, J=22 Hz), 1.42 (t, 3H, J=7.1 Hz), 2.35 (t, 1H, J=8 Hz), 2.89 (t, 1H, J=8 Hz), 2.97 (m, 1H), 3.12 (m, 1H), 3.24 (m, 1H), 3.68 (t, 1H, J=6 Hz), 4.27 (s, 1H), 4.38 (q, 2H, J$_1$=14, J$_2$=7 Hz), 7.103-7.66 (m, 13H); Mass Spectrum: m/e=464 (M+1).

Step 4: Ethyl 3-(1-azetidin-3-yl-2-fluoro-2-methylpropyl)-5-fluorobenzoate

Ethyl 3-{1-[1-(diphenylmethyl)azetidin-3-yl]-2-fluoro-2-methylpropyl}-5-fluorobenzoate (7.6 g, 16.40 mmol) was hydrogenated in 150 mL of EtOH in the presence 3.4 g of Pd(OH)$_2$ under 50 Psi pressure hydrogen for 24 h. Then it was filtered to remove the solid and washed with $CH_2Cl_2$. The combined organic layer was concentrated and washed with hexanes/ether to afford the title compound as an white solid. Mass Spectrum: m/e=298 (M+1).

Step 5: Ethyl 3-(1-{1-[(4-chlorophenyl)(3-cyanophenyl)methyl]azetidin-3-yl}-2-fluoro-2-methylpropyl)-5-fluorobenzoate The mixture of 4.90 g (16.40 mmol) of ethyl 3-(1-azetidin-3-yl-2-fluoro-2-methylpropyl)-5-fluorobenzoate, 8.17 g of 3-[bromo(4-chlorophenyl)methyl]benzonitrile, 6 mL(34.36 mmol) of DIEA in 40 mL of acetonitrile was refluxed for 4 h, then concentrated in vacuo. The mixture was poured into 150 mL of $CH_2Cl_2$ and 30 mL of aq $NaHCO_3$. The organic layer was dried over $Na_2SO_4$ and concentrated. Two pairs of racemic compounds were separated by silica gel chromatography. Single diastereomers were separated by a chiral AD column; Mass Spectrum: m/e=523 (M+1, $^{35}Cl$), 525 (M+1, 37Cl).

Preparation 18

Ethyl 3-(1-{1-[(4-cyanophenyl)(3-cyanophenyl)methyl]azetidin-3-yl}-2-fluoro-2-methylpropyl)-5-fluorobenzoate Prepared from ethyl 3-(1-azetidin-3-yl-2-fluoro-2-methylpropyl)-5-fluorobenzoate and 3-[bromo(4-cyanophenyl)methyl]benzonitrile as described in Preparation 17, Part 5; Mass Spectrum: m/e=514.

Preparation 19

3-((1S)-1-{1-[(S)-(4-chlorophenyl)(3-cyanophenyl)methyl]azetidin-3-yl}-2-fluoro-2-methylpropyl)-5-fluorobenzohydrazide A mixture of 523 mg (0.41 mmol) of ethyl 3-(1-{1-[(4-chlorophenyl)(3-cyanophenyl)methyl] azetidin-3-yl}-2-fluoro-2-methylpropyl)-5-fluorobenzoate (Preparation 17), 0.6 mL(1 6.36 mmol) of hydrazine, and 4 mL of EtOH was heated to reflux. After 8 h, the mixture was concentrated to remove solvents to afford the of title compound as an white solid. $^1$H-NMR(CDCl$_3$) δ 1.20(d, 3H, J=21 Hz), 1.29(d, 3H, J=21 Hz), 2.32 (t, 3H, J=7.1 Hz), 2.85 (t, 1H, J=8 Hz), 2.94 (m, 1H), 3.06 (m, 1H), 3.20 (m, 1H), 3.51 (s, 2H), 3.63 (t, 1H, J=5 Hz), 4.26 (s, 1H), 7.06-7.71 (m, 11H); Mass Spectrum: m/e=509 (M+1, $^{35}Cl$), 511 (M+1, $^{37}Cl$).

Preparation 20

3-[(4-chlorophenyl)(3-{2-fluoro-1-[3-fluoro-5-(hydroxymethyl)phenyl]-2-methylpropyl}azetidin-1-yl)methyl]benzonitrile To the mixture of 42 mg (0.08 mmol) of ethyl 3-(1-{1-[(4-chlorophenyl)(3-cyanophenyl)methyl]azetidin-3-yl}-2-fluoro-2-methylpropyl)-5-fluorobenzoate in 3 mL of THF was added 0.18 mL (0.36 mmol) of 2 M LiBH$_4$ solution in THF and the solution was stirred overnight at rt. Then it was poured into 20 mL of $CH_2Cl_2$ and 5 mL of water. The water layer was extracted with $CH_2Cl_2$ and the combined organic layer was concentrated. The residue was purified by silica gel chromatography with hexane/ethyl acetate to afford the title compound as a white solid; Mass Spectrum: m/e=481 (M+1, $^{35}Cl$), 483 (M+1, $^{37}Cl$).

Preparation 21

3-(1-{1-[(4-chlorophenyl)(3-cyanophenyl)methyl]azetidin-3-yl}-2-fluoro-2-methylpropyl)-5-fluorobenzoic acid A mixture of 112 mg (0.214 mmol) of ethyl 3-(1-{1-[(4-chlorophenyl)(3-cyanophenyl)methyl]azetidin-3-yl}-2-fluoro-2-methylpropyl)-5-fluorobenzoate and 1.2 mL of 1M LiOH in 5 mL of EtOH was stirred for 2.5 h at rt. The solution was adjusted to pH=5-6 with 6N HCl and concentrated to remove solvents. The residue was dissolve in 10 mL of $CH_2Cl_2$ and solids were removed by filtration. The solution was concentrated to afford the title compound as a white solid; Mass Spectrum: m/e=495 (M+1, $^{35}Cl$), 497 (M+1, $^{37}Cl$).

Preparation 22

3-{1-1-[(4-chlorophenyl)(3-cyanophenyl)methyl]azetidin-3-yl}-2-fluoro-2-methylpropyl)-5-fluoro-N-methylbenzamide A solution of 46 mg (0.093 mmol) of 3-(1-{1-[(4-chlorophenyl)(3-cyanophenyl)methyl]azetidin-3-yl}-2-fluoro-2-methylpropyl)-5-fluorobenzoic acid, 39.2 mg (0.204 mmol) of N-(3-dimethyl-aminopropyl)-N-ethylcarbodiimide hydrochloride, 6.2 mg (0.046 mmol) of HOBT, 120 uL (0.23 mmol) of methyl amine (2M in THF), 48 uL (0.28 mmol) of DIEA in 2 mL of $CH_2Cl_2$ was stirred overnight at rt. Then it was concentrated. The residue was purified by silica gel chromatography with hexane/acetone to afford the title compound as a white solid; Mass Spectrum: m/e=508 (M+1, $^{35}Cl$), 510 (M+1, $^{37}Cl$).

Preparation 23

3-(1-{1-[(4-chlorophenyl)(3-cyanophenyl)methyl]azetidin-3-yl}-2-fluoro-2-methylpropyl)-5-fluoro-N,N-dimethylbenzamide Prepared from 3-(1-{1-[(4-chlorophenyl)(3-cyanophenyl)methyl]azetidin-3-yl}-2-fluoro-2-methylpropyl)-5-fluorobenzoic acid and dimethylamine according to the procedure described in Preparation 22; Mass Spectrum: m/e=522 (M+1, $^{35}Cl$), 524 (M+1, $^{37}Cl$).

Preparation 24

3-(1-{1-[(4-chlorophenyl)(3-cyanophenyl)methyl]azetidin-3-yl}-2-fluoro-2-methylpropyl)-5-fluorobenzamide Prepared from 3-(1-{1-[(4-chlorophenyl)(3-cyanophenyl)methyl]azetidin-3-yl}-2-fluoro-2-methylpropyl)-5-fluorobenzoic acid and ammonia according to the procedure described in Preparation 22; Mass Spectrum: m/e=494 (M+1, $^{35}Cl$), 496 (M+1, $^{37}Cl$).

Preparation 25

Isopropyl 3-(1-{1-[(4-chlorophenyl)(3-cyanophenyl)methyl]azetidin-3-yl}-2-fluoro-2-methylpropyl)-5-fluorobenzoate Prepared from 3-(1-{1-[(4-chlorophenyl)(3-cyanophenyl)methyl]azetidin-3-yl}-2-fluoro-2-methylpropyl)-5-fluorobenzoic acid and isopropanol according to the procedure described in Preparation 21; Mass Spectrum: m/e=537 (M+1, $^{35}Cl$), 539 (M+1, $^{37}Cl$).

Preparation 26

Methyl 4-((R)-(3-cyanophenyl){3-[(1S)-1-(3,5-difluorophenyl)-2-fluoro-2-methylpropyl]azetidin-1-yl}methyl)benzoate Step 1 Methyl 4-[(3-cyanophenyl)(hydroxy)methyl]benzoate A solution of 3.0 g (15 mmole) of methyl 4-(chlorocarbonyl)benzoate and 183 mg (0.2 mmole) of tris(dibenzylideneacetone)dipalladium(0) was cooled to 0° C. under $N_2$. After 5 min, 32 mL of a 0.5 M solution of (3-cyanophenyl)(iodo)zinc in THF was added dropwise and the solution was stirred at rt. After 4 h, the reaction was quenched by addition of saturated $NH_4Cl$ solution and 30 mL ether. The layers were separated and the aqueous layer was washed with three 30 mL portions of ether. The combined organic extracts were washed with 30 mL of saturated $NaHCO_3$ solution and 30 mL brine before being dried over $MgSO_4$ and concentrated. The residue was dissolved in 50 mL of 1:5 $CH_3OH$-THF and cooled to 0° C. To this was added 500 mg (13.5 mmole) of $NaBH_4$ in two portions over 10 minutes. After 20 min, the reaction was quenched by addition of 1 mL saturated $Na_2SO_4$ solution and concentrated. The resulting slurry was diluted with ether and filtered. The solid residue was washed with ether and the combined filtrates were washed with brine, dried over $Na_2SO_4$ and concentrated to an oil that was purified by silica gel chromatography using a step-gradient of 10 to 25% EtOAc-hexane. Homogeneous fractions were combined and concentrated to afford the title compound as a white solid.

Step 2: Methyl 4-[(3-cyanophenyl)(hydroxy)methyl]benzoate

To a solution of 267 mg (1 mmole) of methyl 4-[(3-cyanophenyl)(hydroxy)methyl]benzoate in 3 mL of $CH_2Cl_2$ was added 66 uL (107 mg, 0.9 mmole) of $SOCl_2$. The solution was stirred under $N_2$ at rt for 1 h, then was cooled to 0° C. in an ice bath. To this was added 140 uL (327 mg, 1.8 mmole) of $SOBr_2$ and the solution was stirred at 0° C. for 2 h. The reaction was quenched by dropwise addition of saturated aqueous $NaHCO_3$ solution. The layers were separated and the aqueous layer was washed with two 20 mL portions of ether. The combined organic extracts were washed with brine, dried over $MgSO_4$ and concentrated. The resulting oil was used directly in the next step.

Step 3: Methyl 4-((S)-(3-cyanophenyl){3-[(1S)-1-(3,5-difluorophenyl)-2-fluoro-2-methylpropyl]azetidin-1-yl}methyl)benzoate The title compound was prepared methyl 4-[bromo(3-cyanophenyl)methyl]benzoate and 3-[(1S)-1-(3,5-difluorophenyl)-2-fluoro-2-methylpropyl]azetidine (Step 1, Preparation 15) by the procedure described in Step 2 of Preparation 15. The product was purified by chromatography on an AD column using 30% isopropanol-heptane to afford the title compound; $^1$H-NMR(CDCl$_3$) δ 1.25 (t, J=22 Hz, 6H), 2.33 (t, J=6.5 Hz, 1H), 2.83-2.89 (m, 2H), 3.05-3.22 (m, 2H), 3.65 (m, 1H), 3.92 (s, 3H), 4.34 (s, 1H), 6.68-6.71 (m, 3H), 7.21-7.8 (m, 8H); Mass Spectrum: m/e=493 (M+1).

Preparation 27

Methyl 4-((S)-(3-cyanophenyl){3-[(1S)-1-(3,5-difluorophenyl)-2-fluoro-2-methylpropyl]azetidin-1-yl}methyl)benzoate Further elution of the AD column from Example Preparation 26, Step 3, afforded the title compound; $^1$H-NMR (CDCl$_3$) δ 1.25 (t, J=22 Hz, 6H), 2.33 (t, J=6.5 Hz, 1H), 2.83-2.89 (m, 2H), 3.05-3.22 (m, 2H), 3.65 (m, 1H), 4.02 (s, 3H), 4.34 (s, 1H), 6.68-6.71 (m, 3H), 7.21-7.8 (m, 8H); Mass Spectrum: m/e=493 (M+1).

Preparation 28

Isopropyl 4-((S)-(3-cyanophenyl){3-[(1S)-1-(3,5-difluorophenyl)-2-fluoro-2-methylpropyl]azetidin-1-yl}methyl)benzoate A solution of 10 mg (0.02 mmole) of methyl 4-((S)-(3-cyanophenyl){3-[(1S)-1-(3,5-difluorophenyl)-2-fluoro-2-methylpropyl]azetidin-1-yl}methyl)benzoate in 2 mL isopropanol was cooled to 0° C., To this was added 2 drops of a 1.6M solution of butyllithium in hexane and the solution was allowed to warm to room temperature over 3 h. The reaction was quenched by addition of 2 drops of saturated $NaHCO_3$ solution and the solution was concentrated. The residue was triturated with $CH_2Cl_2$, and the solution concentrated. The residue was filtered through a plug of silica gel using 35% EtOAc-hexane to afford the title compound; $^1$H-NMR (CDCl$_3$) δ 1.21 (t, J=10 Hz, 6H), 1.36 (t, J=22 Hz, 3H), 1.3 (t, J=22 Hz, 3H), 2.37 (t, J=6.5 Hz, 1H), 2.83-2.89 (m, 2H), 3.05-3.22 (m, 2H), 3.65 (m, 1H), 4.02 (s, 3H), 4.34 (s, 1H), 6.68-6.71 (m, 3H), 7.21-7.8 (m, 8H); Mass Spectrum: m/e=521 (M+1).

Preparation 29

Ethyl 4-((S)-(3-cyanophenyl)){3-[(1S)-1-(3,5-difluorophenyl)-2-fluoro-2-methylpropyl]azetidin-1-yl}methyl)benzoate The title compound was prepared from methyl 4-((S)-(3-cyanophenyl){3-[(1S)-1-(3,5-difluorophenyl)-2-fluoro-2-methylpropyl]azetidin-1-yl}methyl)benzoate according to the procedures described in Preparation 28 except that ethanol was used instead of isopropanol as the solvent; Mass Spectrum: m/e=507 (M+1)

Preparation 30

3-((S)-(4-chlorophenyl){3-[(1S)-1-(3,5-difluorophenyl)-2-fluoro-2-methylpropyl]azetidin-1-yl}methyl)benzohydrazide The title compound was prepared from methyl 4-((S)-(3-cyanophenyl){3-[(S1)-1-(3,5-difluorophenyl)-2-fluoro-2-methylpropyl]azetidin-1-yl}methyl)benzoate according to the procedure listed in Preparation 19; Mass Spectrum: m/e=493 (M+1).

Preparation 31

Methyl (2S)-(3-bromo-5-fluorophenyl){1-[(S)-(4-chlorophenyl)(3-cyanophenyl)methyl]azetidin-3-yl}acetate Step 1 Methyl (2R)-(3-bromo-5-fluorophenyl){1-[(S)-(4-chlorophenyl)(3-cyanophenyl)methyl]azetidin-3-yl}acetate Further elution of the column in Example 26, Step 7 afforded methyl (2R)-(3-bromo-5-fluorophenyl){1-[(S)-(4-chlorophenyl)(3-cyanophenyl)methyl]azetidin-3-yl}acetate; $^1$H-NMR(CDCl$_3$) δ 2.67(t, 1H, J=6.2 Hz), 2.90(dd, 1H, J$_1$=7.3 Hz, J$_2$=5.5 Hz ), 3.09-3.13(m, 2H), 3.43(t, 1H, J=7.3 Hz), 3.68(s, 3H), 3.82(d, 1H, J=10.7 Hz), 4.34(s, 1H), 6.96 (d, 1H, J=8.9 Hz), 7.17(d, 1H, J=8.1 Hz), 7.20 (d, 1H, J=12 Hz), 7.26-7.32 (m, 5H), 7.40 (t, 1H, J=7.6 Hz), 7.50 (d, 1H, J=7.7 Hz), 7.60 (d, 1H, J=8.0 Hz), 7.70 (s, 1H); Mass Spectrum: m/e=527 527(M+1, $^{35}$Cl $^{79}$Br), 529 (M+1, $^{37}$Cl $^{79}$Br/$^{35}$Cl $^{81}$Br), 531 (M+1, $^{37}$Cl $^{81}$Br).

Step 2 Methyl (2S)-(3-bromo-5-fluorophenyl){1-[(S)-(4-chlorophenyl)(3-cyanophenyl)methyl]azetidin-3-yl}acetate To a solution of 20.56 g (38.95 mmol) of methyl (2R)-(3-bromo-5-fluorophenyl){1-[(S)-(4-chlorophenyl)(3-cyanophenyl)methyl]azetidin-3-yl}acetate in 250 mL of THF, A solution of 40.90 mL (40.9 mmol) of lithium bis(trimethylsilyl)amide(1M in THF) was added and the reaction mixture was stirred for 50 min. at −78° C. Then the reaction was quenched with 1N HCl (PH=7-8) at 0° C. The mixture was transferred into 200 mL ether and the water layer was extracted with CH$_2$Cl$_2$ (100 mL×2). The combined organic layer was dried over Na$_2$SO$_4$ and concentrated. The residue was separated by silica gel chromatography with cyclohexane/ethyl acetate to afford the title compound, methyl (2S)-(3-bromo-5-fluorophenyl){1-[(S)-(4-chlorophenyl)(3-cyanophenyl)methyl]azetidin-3-yl}acetate; $^1$H-NMR(CDCl$_3$) δ 2.66(t, 1H, J=6.2 Hz), 2.92(dd, 1H, J$_1$=7.5 Hz, J$_2$=5.7 Hz), 3.08-3.16(m, 2H), 3.41(t, 1H, J=7.2 Hz), 3.69(s, 3H), 3.83(d, 1H, J=10.7 Hz), 4.34(s, 1H), 6.96 (d, 1H, J=8.9 Hz), 7.17(d, 1H, J=8.0 Hz), 7.20 (d, 1H, J=12 Hz), 7.27-7.32 (m, 5H), 7.39 (t, 1H, J=7.6 Hz), 7.50 (d, 1H, J=7.5 Hz), 7.60 (d, 1H, J=7.5 Hz), 7.70 (s, 1H); Mass Spectrum: m/e=527(M+1, $^{35}$Cl$^{79}$Br), 529 (M+1, $^{37}$Cl$^{79}$Br/$^{35}$Cl $^{81}$Br), 531 (M+1, $^{37}$Cl $^{81}$Br). Further elution of the column afforded methyl (2R)-(3-bromo-5-fluorophenyl){1-[(S)-(4-chlorophenyl)(3-cyanophenyl)methyl]azetidin-3-yl}acetate; $^1$H-NMR(CDCl$_3$) δ 2.67(t, 1H, J=6.2 Hz), 2.90(dd,1H, J$_1$=7.3 Hz, J$_2$=5.5 Hz), 3.09-3.13(m, 2H), 3.43(t, 1H, J=7.3 Hz), 3.68(s, 3H), 3.82(d, 1H, J=10.7 Hz), 4.34(s, 1H), 6.96 (d, 1H, J=8.9 Hz), 7.17(d, 1H, J=8.1 Hz), 7.20 (d, 1H, J=12 Hz), 7.26-7.32 (m, 5H), 7.40 (t, 1H, J=7.6 Hz), 7.50 (d, 1H, J=7.7 Hz), 7.60 (d, 1H, J=8.0 Hz), 7.70 (s, 1H); Mass Spectrum: m/e=527 (M+1, $^{35}$Cl $^{79}$Br), 529 (M+1, $^{37}$Cl$^{79}$Br/$^{35}$Cl $^{81}$Br), 531 (M+1, $^{37}$Cl $^{81}$Br).

EXAMPLE 1

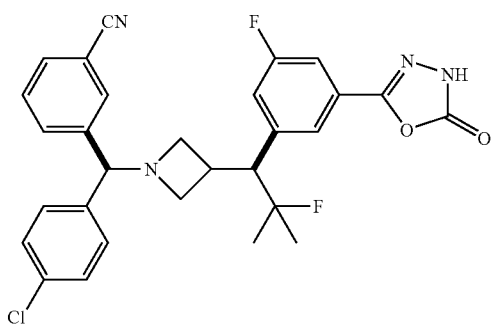

3-[(S)-(4-chlorophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile To a solution of 44 mg (0.86 mmol) of 3-((1S)-1-{1-[(S)-(4-chlorophenyl)(3-cyanophenyl) methyl]azetidin-3-yl}-2-fluoro-2-methylpropyl)-5-fluorobenzohydrazide (Preparation 19) in 2 mL CH$_2$Cl$_2$ was added 11.3 uL(0.215 mmol) of phosgene solution (20% in toluene) at 0° C., followed by stirring at rt. After 1.5 h, the solution was concentrated in vacuo to remove solvents and 2 mL of 2N NH$_3$ in MeOH was added and the solution was concentrated again. The residue was purified by silica gel chromatography with CH$_2$Cl$_2$/acetone to afford the title compound as a white solid; $^1$H-NMR (CDCl$_3$) δ 1.22(d, 3H, J=22 Hz), 1.28(d, 3H, J=22 Hz), 2.36 (t, 1H, J=8 Hz), 2.91 (t, 1H, J=8 Hz), 2.96 (m, 1H), 3.12 (t, 1H, J=7 Hz), 3.27 (m, 1H), 3.64 (t, 1H, J=6 Hz), 4.30 (s, 1H), 7.06-7.71 (m, 12H); Mass Spectrum: m/e=535 (M+1, $^{35}$Cl), 537 (M+1, $^{37}$Cl).

EXAMPLE 2

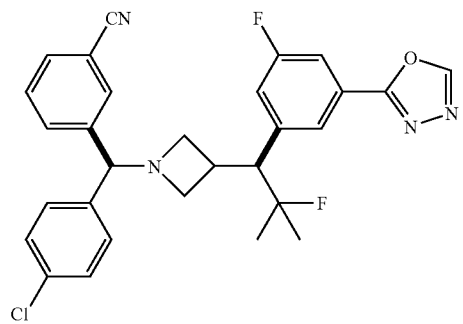

3-[(S)-(4-chlorophenyl)(3-{(1S)-2-fluoro-1-[3-fluoro-5-(1,3,4-oxadiazol-2-yl)phenyl]-2-methylpropyl}azetidin-1-yl)methyl]benzonitrile A solution of 41 mg (0.081 mmol) of 3-((1S)-1-{1-[(S)-(4-chlorophenyl)(3-cyanophenyl)methyl]azetidin-3-yl}-2-fluoro-2-methylpropyl)-5-fluorobenzohydrazide and 1.5 mL triethyl orthoformate in 2 mL of xylene was stirred for 3.5 at 125° C., followed by concentration to remove solvents. The residue was purified by silica gel chromatography with hexane/ethyl acetate/ammonia in MeOH to afford the title compound as a white solid; $^1$H-NMR(CDCl$_3$) δ 1.23(d, 3H, J=22 Hz), 1.29(d, 3H, J=22 Hz), 2.34 (t, 1H, J=8 Hz), 2.89 (t, 1H, J=8 Hz), 2.98 (m, 1H), 3.02 (t, 1H, J=11 Hz), 3.25 (m, 1H), 3.63 (t, 1H, J =6 Hz), 4.23 (s, 1H), 7.11-7.73 (m, 11H), 8.51(s, 1H); Mass Spectrum: m/e=519 (M+1, $^{35}$Cl), 521 (M+1, $^{37}$Cl).

EXAMPLE 3

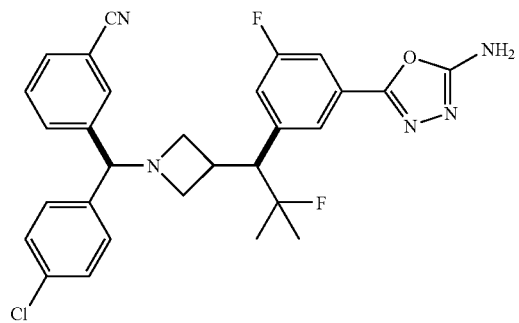

3-[(S)-(3-{(1S)-1-[3-(5-amino-1,3,4-oxadiazol-2-yl)-5-fluorophenyl]-2-fluoro-2-methylpropyl}azetidin-1-yl)(4-chlorophenyl)methyl]benzonitrile To a mixture of 53 mg (0.104 mmol) of 3-((1S)-1-{1-[(S)-(4-chlorophenyl)(3-cyanophenyl) methyl]azetidin-3-yl}-2-fluoro-2-methylpropyl)-5-fluorobenzohydrazide in 3 mL of dioxane, 11.4 mg (0.135 mmol) of NaHCO$_3$ in 1 mL of water was added 13 mg (0.125 mmol) cyanogen bromide and the solution was stirred at rt. After 2.5 h, it was concentrated to remove solvents. The residue was dissolved in 20 mL of CH$_2$Cl$_2$ and 5 mL of water and the pH was adjusted to 7-8 with aq NaHCO$_3$. The aqueous layer was extracted with CH$_2$Cl$_2$, and the combined organic layer was concentrated. The residue was purified by silica gel chromatography with CH$_2$Cl$_2$/acetone to afford the title compound as a white solid; $^1$H-NMR (CDCl$_3$) δ 1.22(d, 3H, J=22 Hz), 1.28(d, 3H, J=22 Hz), 2.34 (br, 1H) 2.88 (br, 1H), 2.96 (m, 1H), 3.10 (dr, 1H), 3.24 (m, 1H), 3.63 (br, 1H), 4.2 (s, 1H), 5.50(s, 2H), 7.01-7.66 (m, 11H); Mass Spectrum: m/e=534 (M+1, $^{35}$Cl), 536 (M+1, $^{37}$Cl).

EXAMPLE 4

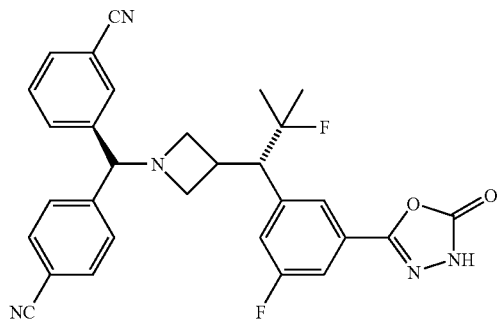

3-[(S)-(4-cyanophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile Prepared from ethyl 3-(1-{1-[(4-cyanophenyl)(3-cyanophenyl)methyl]azetidin-3-yl}-2-fluoro-2-methylpropyl)-5-fluorobenzoate (Preparation 18) according to the procedures in Preparation 19 and Example 1; Mass Spectrum: m/e=526 (M+1).

EXAMPLE 5

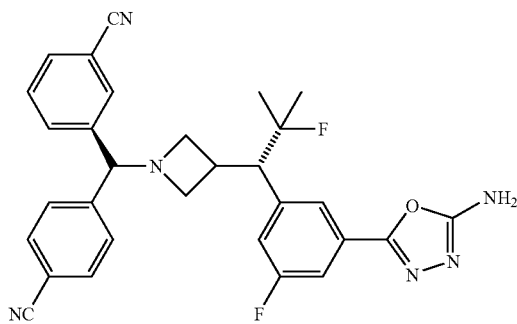

3-[(S)-(3-{(1S)-1-[3-(5-amino-1,3,4-oxadiazol-2-yl)-5-fluorophenyl]-2-fluoro-2-methylpropyl}azetidin-1-yl)(4-cyanophenyl)methyl]benzonitrile Prepared from ethyl 3-(1-{1-[(4-cyanophenyl)(3-cyanophenyl)methyl]azetidin-3-yl}-2-fluoro-2-methylpropyl)-5-fluorobenzoate (Preparation 18) according to the procedures in Preparation 19 and Example 3; Mass Spectrum: m/e=525 (M+1).

EXAMPLE 6

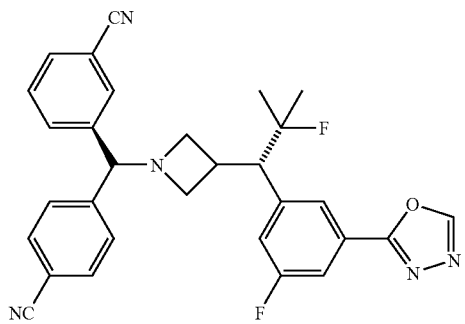

3-[(S)-(4-cyanophenyl)(3-{(1S)-2-fluoro-1-[3-fluoro-5-(1,3,4-oxadiazol-2-yl)phenyl]-2-methylpropyl}azetidin-1-yl)methyl]benzonitrile Prepared from ethyl 3-(1-{1-[(4-cyanophenyl)(3-cyanophenyl)methyl]azetidin-3-yl}-2-fluoro-2-methylpropyl)-5-fluorobenzoate (Preparation 18) according to the procedures in Preparation 19 and Example 2; Mass Spectrum: m/e=510 (M+1).

EXAMPLE 7

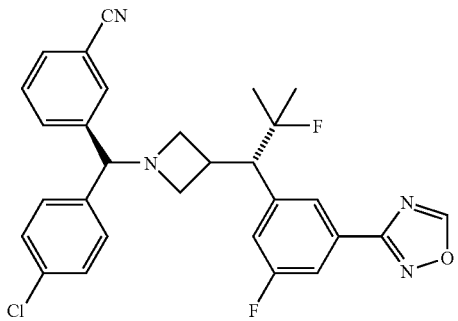

3-[(S)-(4-chlorophenyl)(3-{(1S)-2-fluoro-1-[3-fluoro-5-(1,2,4-oxadiazol-3-yl)phenyl]-2-methylpropyl}azetidin-1-yl)methyl]benzonitrile Step 1: 3-[(S)-{3-[(1S)-1-(3-bromo-5-fluorophenyl)-2-fluoro-2-methylpropyl]azetidin-1-yl}(4-chlorophenyl)methyl]-N'-hydroxybenzenecarboximidamide The mixture of 240 mg (0.45 mmol) of 3-[(S)-{3-[(1S)-1-(3-bromo-5-fluorophenyl)-2-fluoro-2-methylpropyl]azetidin-1-yl}(4-chlorophenyl)methyl]benzonitrile, 47.2 mg (0.68 mmol) of hydroxylamine hydrochloride, 0.124 mL (0.9 mmol) of triethylamine, and 5 mL of ethanol was heated to reflux for 4 h. The solution was concentrated and the residue was poured into 20 mL of $CH_2Cl_2$ and 5 mL of aq $NaHCO_3$ (PH>7). The aqueous layer was extracted with two 10 mL portions of $CH_2Cl_2$. The combined organic layer was dried over $Na_2SO_4$ and concentrated to afford the title compound as a white solid; Mass Spectrum: m/e=562 (M+1, $^{35}Cl$), 564 (M+1, $^{37}Cl$).

Step 2: 3-{3-[(S)-{3-[(1S)-1-(3-bromo-5-fluorophenyl)-2-fluoro-2-methyl propyl]azetidin-1-yl}(4-chlorophenyl)methyl]phenyl}-1,2,4-oxadiazole A mixture of 70 mg (0.125 mmol) of 3-[(S)-{3-[(1S)-1-(3-bromo-5-fluoro phenyl)-2-fluoro-2-methylpropyl]azetidin-1-yl}(4-chlorophenyl)methyl]-N-hydroxybenzenecarboximidamide, 1.5 mL of triethyl orthoformate, and 2 mL of xylene was stirred for 4 h at 125-130° C. Then it was concentrated, and the residue was purified by silica gel chromatography with hexanes/acetone to afford the title compound as a white solid; Mass Spectrum: m/e=572 (M+1, $^{35}Cl$), 574 (M+1, $^{37}Cl$).

Step 3: 3-[(1S)-1-(1-{(S)-(4-chlorophenyl)[3-(1,2,4-oxadiazol-3-yl)phenyl]-methyl}azetidin-3-yl)-2-fluoro-2-methylpropyl]-5-fluorobenzonitrile A mixture of 60 mg (0.104 mmol) of 3-{3-[(S)-{3-[(1S)-1-(3-bromo-5-fluorophenyl)-2-fluoro-2-methyl propyl]azetidin-1-yl}(4-chlorophenyl)methyl]phenyl}-1,2,4-oxadiazole, 48.5 mg (0.84 mmol) of zinc cyanide, 4 mg (0.004 mmol) of tris(dibenzylideneacetone)-dipalladium, and 5 mg (0.009 mmol) of DPPF in 3 mL of $DMF/H_2O$ (99/1) was degassed with $N_2$ for 1 h at rt. Then it was stirred at 135° C. After 14 h, the reaction mixture was concentrated to remove solvents. Then the mixture was poured into 20 mL of $CH_2Cl_2$ and 5 mL of aq $NaHCO_3$ (pH>7). The aqueous layer was extracted with $CH_2Cl_2$ and the combined organic layer was dried over $Na_2SO_4$ and concentrated. The residue was purified by silica gel chromatography with hexanes/acetone to afford the title compound as a white solid; Mass Spectrum: m/e=519 (M+1, $^{35}Cl$), 521 (M+1, $^{37}Cl$).

EXAMPLE 8

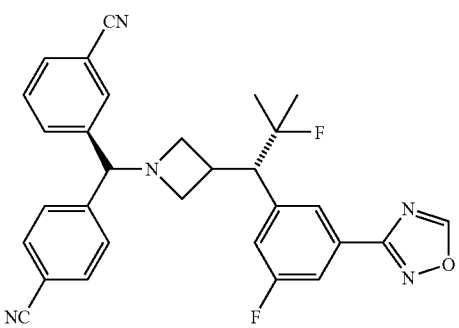

3-[(1S)-1-(1-{(S)-(4-cyanophenyl)[3-(1,2,4-oxadiazol-3-yl)phenyl]-methyl}azetidin-3-yl)-2-fluoro-2-methylpropyl]-5-fluorobenzonitrile Further elution of the column in Example 7, Step 3 afforded the title compound; Mass Spectrum: m/e=510 (M+1).

EXAMPLE 9

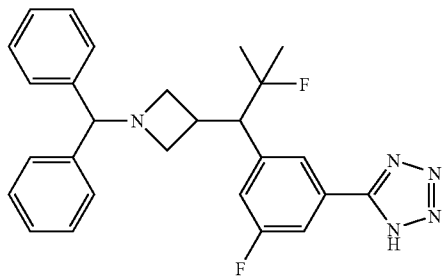

5-(3-{1-[1-(diphenylmethyl)azetidin-3-yl]-2-fluoro-2-methylpropyl}-5-fluorophenyl)-1H-tetrazole A mixture of 1.17 g (2.81 mmol) of 3-{1-[(diphenylmethyl)azetidin-3-yl]-2-fluoro-2-methylpropyl}-5-fluorobenzonitrile, 914 mg (14.06 mmol) of sodium azide, and 715 mg (14.05 mmol) of ammonium chloride in 15 mL of DMF was stirred for 16 h. Then it was concentrated to remove solvents. The residue was purified by silica gel chromatography with $CH_2Cl_2/MeOH/NH_3$ (2M) in MeOH to afford the title compound as a white solid;

$^1$H-NMR($CDCl_3$) δ 1.26(s, 3H), 1.30(s, 3H), 3.80 (br, 1H) 4.12 (br, 1H), 6.90-7.93 (m, 13H), 8.21(d, 1H, J=14 Hz); Mass Spectrum: m/e=460 (M+1).

EXAMPLE 10

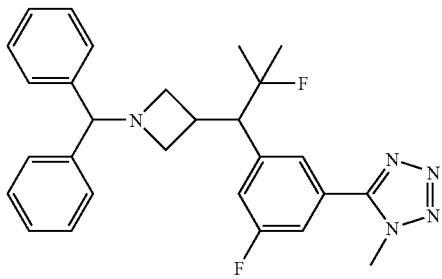

5-(3-{1-[1-(diphenylmethyl)azetidin-3-yl]-2-fluoro-2-methylpropyl}-5-fluorophenyl)-1-methyl-1H-tetrazole The reaction of mixture of 1.31 g (2.85 mmol) 5-(3-{1-[1-(diphenylmethyl)azetidin-3-yl]-2-fluoro-2-methylpropyl}-5-fluorophenyl)-1H-tetrazole, 0.36 mL (5.70 mmol) methyl iodide, and 1.77 mL (9.97 mmol) DIEA in 8 mL MeCN was heated to reflux for 2.5 h. Then it was concentrated to remove the solvents. Then it was added 20 mL of $CH_2Cl_2$ and 5 mL of water and adjust pH=7-8 with aq $NaHCO_3$. The water layer was extracted with $CH_2Cl_2$, and the combined organic layer was concentrated. The residue was separated by silica gel chromatography with $CH_2Cl_2$/MeOH/$NH_3$ (2M) in MeOH to afford the title compound; $^1$H-NMR($CDCl_3$) δ 1.22(d, 3H, J=22 Hz), 1.29(d, 3H, J=22 Hz), 2.37 (t, 1H, J=8 Hz), 2.90 (t, 1H, J=8 Hz), 3.00 (m, 1H), 3.14 (m, 1H), 3.22 (m, 1H), 3.68 (J, 1H, J=6 Hz), 4.19 (s, 3H), 4.26 (s, 1H), 7.12-7.43 (m, 13H); Mass Spectrum: m/e=474 (M+1).

EXAMPLE 11

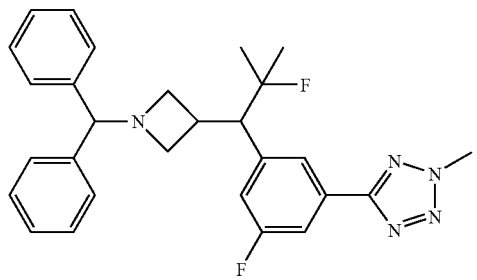

5-(3-{1-[1-(diphenylmethyl)azetidin-3-yl]-2-fluoro-2-methylpropyl}-5-fluorophenyl)-2-methyl-2H-tetrazole Further elution of the column in Example 10 afforded the title compound; $^1$H-NMR($CDCl_3$) δ 1.24(d, 3H, J=20 Hz), 1.29(d, 3H, J=20 Hz), 2.40 (t, 1H, J=8 Hz), 2.90 (t, 1H, J=8 Hz), 3.00 (m, 1H), 3.15 (m, 1H), 3.24 (m, 1H), 3.68 (m, 1H), 4.27 (s, 1H), 4.42 (s, 3H), 7.01-7.44 (m, 11H), 7.70 (m, 1H), 7.77(s, 1H); Mass Spectrum: m/e=474 (M+1).

EXAMPLE 12

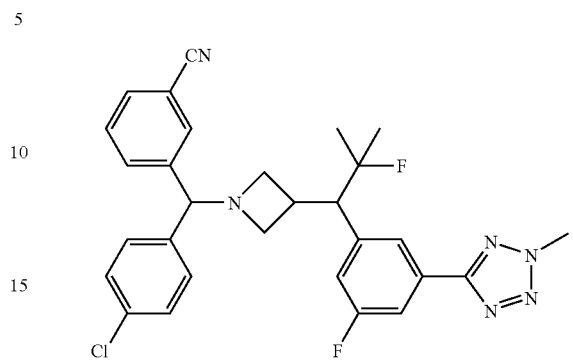

Step 1: 5-[3-(1-azetidin-3-yl-2-fluoro-2-methylpropyl)-5-fluorophenyl]-2-methyl-2H-tetrazole A solution of 370 mg (0.78 mmol) of 5-(3-{1-[1-(diphenylmethyl)azetidin-3-yl]-2-fluoro-2-methylpropyl}-5-fluorophenyl)-2-methyl-2H-tetrazole in 20 mL of EtOH was shaken in presence 200 mg of Pd(OH)$_2$ under 50 Psi pressure hydrogen for 24 h. Then it was filtered to remove the solid and washed with $CH_2Cl_2$. The combined organic layer was concentrated and washed with hexanes/ethyl ether to afford the title compound as a white solid; Mass Spectrum: m/e=308 (M+1).

Step 2: 3-[(4-chlorophenyl)(3-{2-fluoro-1-[3-fluoro-5-(2-methyl-2H-tetrazol-5-yl)phenyl]-2-methylpropyl}azetidin-1-yl)methyl]benzonitrile A mixture of 240 mg (0.78 mmol) of 5-[3-(1-azetidin-3-yl-2-fluoro-2-methylpropyl)-5-fluorophenyl]-2-methyl-2H-tetrazole, 530 mg (1.56 mmol) of 3-[bromo(4-chlorophenyl)methyl]benzonitrile, 1.1 mL(6.26 mmol) of DIEA in 8 mL of acetonitrile was heated to reflux for 4 h. Then, it was concentrated. The mixture was poured into 30 mL of $CH_2Cl_2$ and 5 mL of aq $NaHCO_3$. The organic layer was dried over $Na_2SO_4$ and concentrated. The compounds were purified by silica gel chromatography. Single diastereomers were separated by a chiral AD column; Mass Spectrum: m/e=533 (M+1, $^{35}$Cl), 535 (M+1, $^{37}$Cl).

EXAMPLE 13

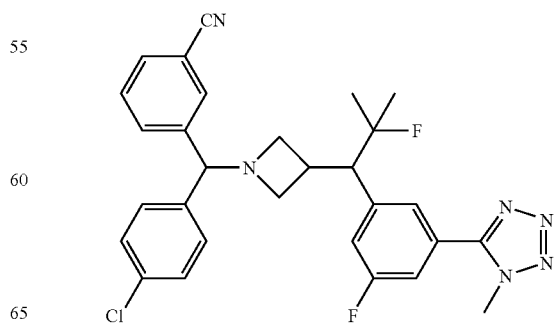

3-[(4-chlorophenyl)(3-{2-fluoro-1-[3-fluoro-5-(1-methyl-1H-tetrazol-5-yl)phenyl]-2-methylpropyl}azetidin-1-yl)methyl]benzonitrile The title compound was prepared from 5-(3-{1-[1-(diphenylmethyl)azetidin-3-yl]-2-fluoro-2-methylpropyl}-5-fluorophenyl)-1-methyl-1H-tetrazole according to the procedures described in Example 12; Mass Spectrum: m/e=533 (M+1, $^{35}$Cl), 535 (M+1, $^{37}$Cl).

EXAMPLE 14

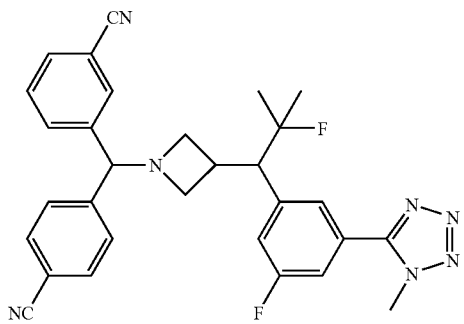

3-[(4-cyanophenyl)(3-{2-fluoro-1-[3-fluoro-5-(1-methyl-1H-tetrazol-5-yl)phenyl]-2-methylpropyl}azetidin-1-yl)methyl]benzonitrile The title compound was prepared from 5-(3-{1-[1-(diphenylmethyl)azetidin-3-yl]-2-fluoro-2-methylpropyl}-5-fluorophenyl)-1H-tetrazole according to the procedures described in Examples 10 and 13; Mass Spectrum: m/e=524 (M+1).

EXAMPLE 15

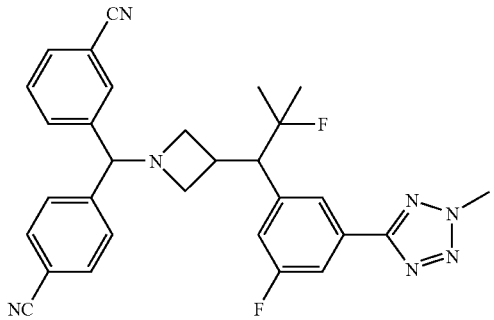

3-[(4-cyanophenyl)(3-{2-fluoro-1-[3-fluoro-5-(2-methyl-2H-tetrazol-5-yl)phenyl]-2-methylpropyl}azetidin-1-yl)methyl]benzonitrile The title compound was prepared from 5-(3-{1-[1-(diphenylmethyl)azetidin-3-yl]-2-fluoro-2-methylpropyl}-5-fluorophenyl)-1H-tetrazole according to the procedures described in Examples 11 and 12; Mass Spectrum: m/e=524 (M+1).

EXAMPLE 16

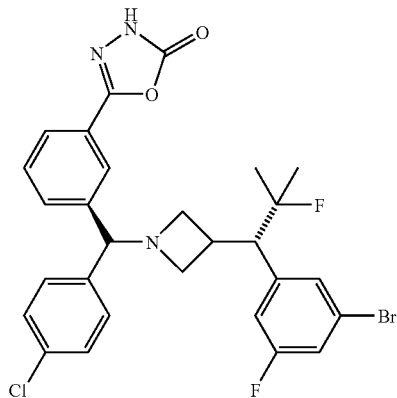

5-{3-[(S)-{3-[(1S)-1-(3-bromo-5-fluorophenyl)-2-fluoro-2-methylpropyl]azetidin-1-yl}(4-chlorophenyl)methyl]phenyl}-1,3,4-oxadiazol-2(3H)-one The title compound was prepared from 3-[{3-[1-(3-bromo-5-fluorophenyl)-2-fluoro-2-methylpropyl]azetidin-1-yl}(4-chlorophenyl)methyl]benzonitrile according to the procedures in Preparation 19 and Example 1; Mass Spectrum: m/e=588 (M+1, $^{35}$Cl $^{79}$Br), 590 (M+1, $^{37}$Cl $^{79}$Br/$^{35}$Cl $^{81}$Br), 592 (M+1, $^{37}$Cl $^{81}$Br).

EXAMPLE 17

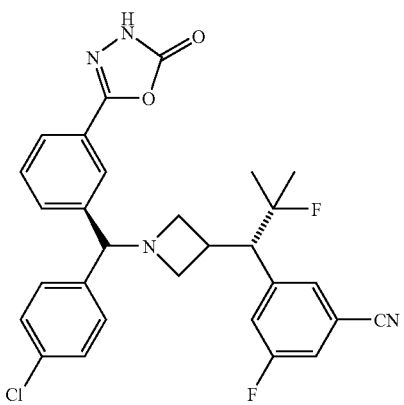

3-[(1S)-1-(1-{(S)-(4-chlorophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile The title compound was prepared from 5-{3-[(S)-{3-[(1S)-1-(3-bromo-5-fluorophenyl)-2-fluoro-2-methylpropyl]azetidin-1-yl}(4-chlorophenyl)methyl]phenyl}-1,3,4-oxadiazol- 2(3H)-one according to the procedure listed in Preparation 16, Step 9; Mass Spectrum: m/e=535 (M+1, $^{35}$Cl), 537 (M+1, $^{37}$Cl).

EXAMPLE 18

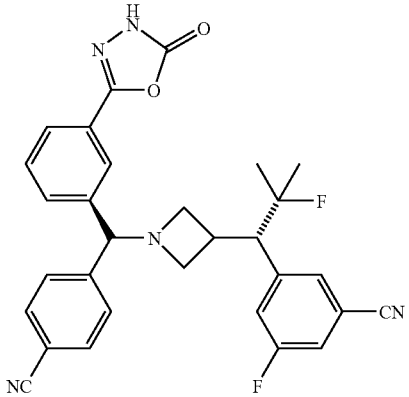

3-[(1S)-1-(1-{(S)-(4-cyanophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile The title compound was prepared from 3-[{3-[1-(3-bromo-5-fluorophenyl)-2-fluoro-2-methylpropyl]azetidin-1-yl}(4-cyanophenyl)methyl]benzonitrile according to the procedures described in Preparation 19 and Example 1 and in Preparation 16, Step 9; Mass Spectrum: m/e=525 (M+1).

EXAMPLE 19

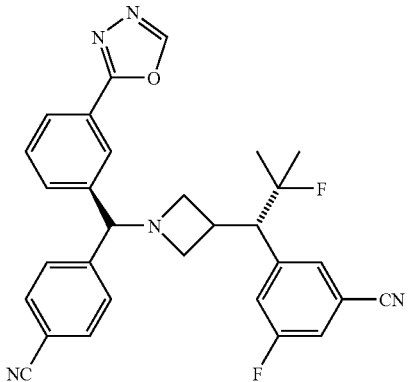

3-[(1S)-1-(1-{(S)-(4-cyanophenyl)[3-(1,3,4-oxadiazol-2-yl)phenyl]methyl}azetidin-3-yl)-2-fluoro-2-methylpropyl]-5-fluorobenzonitrile The title compound was prepared from 3-[{3-[1-(3-bromo-5-fluorophenyl)-2-fluoro-2-methylpropyl]azetidin-1-yl}(4-cyanophenyl)methyl]benzonitrile according to the procedures described in Preparation 19, in Example 2, and in Preparation 16, Step 9; Mass Spectrum: m/e=510 (M+1).

EXAMPLE 20

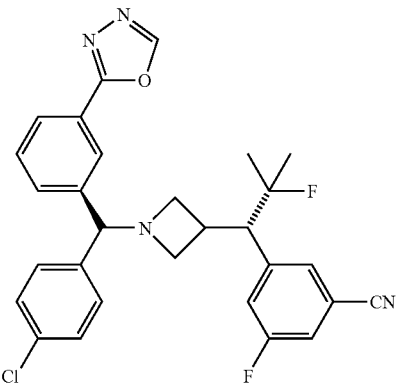

3-[(1S)-1-(1-{(S)-(4-chlorophenyl)[3-(1,3,4-oxadiazol-2-yl)phenyl]methyl}azetidin-3-yl)-2-fluoro-2-methylpropyl]-5-fluorobenzonitrile The title compound was prepared from 5-{3-[(S)-{3-[(1S)-1-(3-bromo-5-fluorophenyl)-2-fluoro-2-methylpropyl]azetidin-1-yl}(4-chlorophenyl)methyl]phenyl}-1,3,4-oxadiazol-2(3H)-one according to the procedure listed in Preparation 19, Example 2, and in Preparation 16, Step 9; Mass Spectrum: m/e=519 (M+1, $^{35}$Cl), 537 (M+1, $^{37}$Cl).

EXAMPLE 21

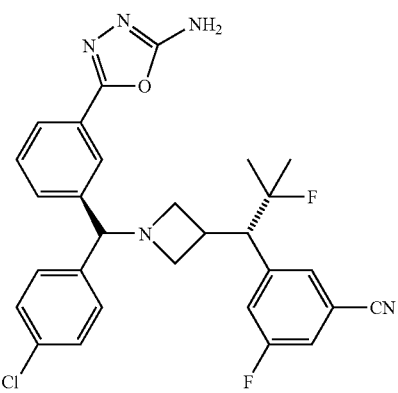

3-((1S)-1-{1-[(S)-[3-(5-amino-1,3,4-oxadiazol-2-yl)phenyl](4-chlorophenyl)methyl]azetidin-3-yl}-2-fluoro-2-methylpropyl)-5-fluorobenzonitrile The title compound was prepared from 5-{3-[(S)-{3-[(1S)-1-(3-bromo-5-fluorophenyl)-2-fluoro-2-methylpropyl]azetidin-1-yl}(4-chlorophenyl)methyl]phenyl}-1,3,4-oxadiazol-2(3H)-one according to the procedure listed in Preparation

EXAMPLE 22

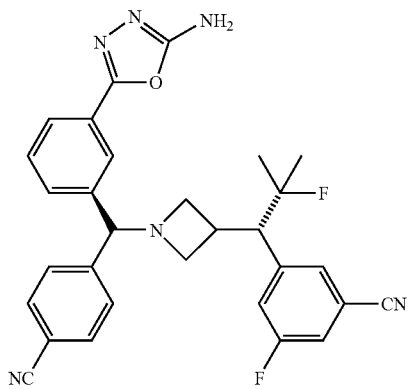

3-((1S)-1-{1-[(S)-[3-(5-amino-1,3,4-oxadiazol-2-yl)phenyl](4-cyanphenyl)methyl]azetidin-3-yl}-2-fluoro-2-methylpropyl)-5-fluorobenzonitrile The title compound was prepared from 3-[{3-[1-(3-bromo-5-fluorophenyl)-2-fluoro-2-methylpropyl]azetidin-1-yl}(4-cyanophenyl)methyl]benzonitrile according to the procedures described in Preparation 19, in Example 2, and in Preparation 16, Step 9; Mass Spectrum: m/e=525 (M+1).

EXAMPLE 23

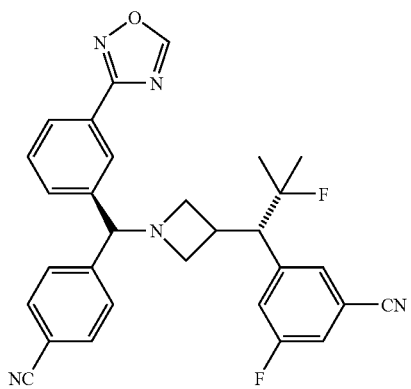

3-[(1S)-1-(1-{(S)-(4-cyanophenyl)[3-(1,2,4-oxadiazol-3-yl)phenyl]methyl}azetidin-3-yl)-2-fluoro-2-methylpropyl]-5-fluorobenzonitrile The title compound was prepared from 3-[{3-[1-(3-bromo-5-fluorophenyl)-2-fluoro-2-methylpropyl]azetidin-1-yl}(4-cyanophenyl)methyl]benzonitrile according to the procedures described in Example 7 and Preparation 16, Step 9; Mass Spectrum: m/e=510 (M+1).

EXAMPLE 24

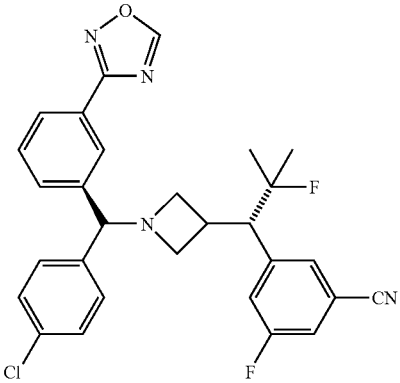

3-[(1S)-1-(1-{(S)-(4-chlorophenyl)[3-(1,2,4-oxadiazol-3-yl)phenol]methyl}azetidin-3-yl)-2-fluoro-2-methylpropyl]-5-fluorobenzonitrile The title compound was prepared from 5-{3-[(S)-{3-[(1S)-1-(3-bromo-5-fluorophenyl)-2-fluoro-2-methylpropyl]azetidin-1-yl}(4-chlorophenyl)methyl]phenyl}-1,3,4-oxadiazol-2(3H)-one according to the procedure listed in Example 8 and in Preparation 16, Step 9; Mass Spectrum: m/e=519 (M+1, $^{35}$Cl), 521 (M+1, $^{37}$Cl).

EXAMPLE 25

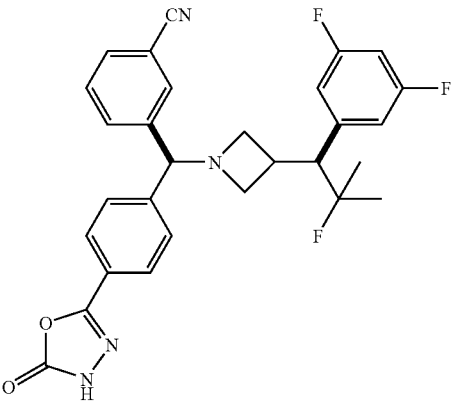

5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one The title compound was prepared from 3-((S)-(4-chlorophenyl){3-[(1S)-1-(3,5-difluorophenyl)-2-fluoro-2-methylpropyl]azetidin-1-yl}methyl)benzohydrazide according to the procedure listed in Example 1; Mass Spectrum: m/e=518 (M+1).

EXAMPLE 26

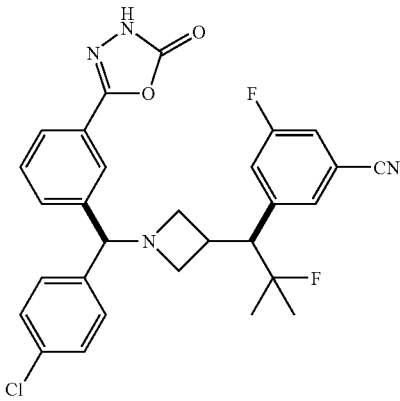

3-[(1S)-1-(1-{(S)-(4-chlorophenyl)[3-(5-oxo-4,5-dihydro-1,3,4-oxadiazol-2-yl)phenol]methyl}azetidin-3-yl)-2-fluoro-2-methylpropyl]-5-fluorobenzonitrile3-[(S)-(4-Chlorophenyl)(3-hydroxyazetidin-1-yl)methyl]benzonitrile Step 1 N-[(1E)-(3-cyanophenyl)methylene]-2-methylpropane-2-(R)sulfinamide A solution of 19.0 g (157 mmole) of (R)-(+)-2-methylpropane-2-sulfinamide and 89.0 g (314 mmole) of titanium tetraisopropoxide in $CH_2Cl_2$ was stirred at room temperature for 10 min. Then a solution of 21.6 g (165 mmole) of 3-formylbenzonitrile in 10 mL $CH_2Cl_2$ was added, and the solution was stirred at room temperature. After 18 h, the reaction was quenched by the addition of 30 mL brine and the solution was rapidly stirred for 15 min. The mixture was filtered through a pad of CELITE and the residue was washed with 300 mL of $CH_2Cl_2$. The combined organic extracts were washed with brine, dried over $Na_2SO_4$ and concentrated. The residue was filtered through a pad of silica gel using 20% ethyl acetate-hexane to afford the title compound; $^1$H-NMR($CDCl_3$) δ 1.31 (s, 9H), 7.65 (t, 1H, J=7.8 Hz), 7.82 (d, 1H, J=7.8 Hz), 8.07 (d, 1H, J=7.8 Hz), 8.20 (s, 1H), 8.62 (s, 1H); Mass Spectrum: m/e=235 (M+1).

Step 2 N-[(S)-(4-chlorophenyl)(3-cyanophenyl)methyl]-2-methylpropane-2-(R)-sulfinamide A solution of 20 g (85.4 mmole) of N-[(1E)-(3-cyanophenyl)methylene]-2-methylpropane-2-(R)sulfonamide in 1000 mL toluene and 400 mL ether was cooled to −60° C. in a dry ice-acetone bath. Then 170 mL of a 1M solution of 4-chlorophenylmagnesium bromide in ether was added at a rate such that the temperature remained between −40° C. and −30° C. and the reaction was stirred at −30° C. for 6 h. The reaction was quenched by addition of 300 mL of saturated $NH_4Cl$ solution and the layers were separated. The organic layer was washed with three 300 mL aliquots of saturated $NH_4Cl$ solution and brine, then was dried over $Na_2SO_4$ and concentrated. The residue was filtered through a pad of silica gel using 10 to 30% ethyl acetate hexane to afford the title compound with de >99% as determined by analytical ChiralPak AD column;; $^1$H-NMR($CDCl_3$) δ 1.27 (s, 9H), 3.76 (s, 1H), 5.65 (d, 1H, J=2.3 Hz), 7.24-7.7 (m, 8H).

Step 3 3-[(S)-amino(4-chlorophenyl)methyl]benzonitrile hydrochloride

To a solution of 850 mg (2.45 mmole) of N-[(S)-(4-chlorophenyl)(3-cyanophenyl)methyl]-2-methylpropane-2-(R)-sulfinamide in 20 mL of $CH_3OH$ was added 2.5 mL of 4M HCL in dioxane. The solution was stirred at room temperature for 45 min, then was diluted with 40 mL ether. The solids were collected by filtration to afford the title compound as a white solid; $^1$H-NMR($CDCl_3$) δ 1.6 (s, 2H, br), 5.24 (s, 1H), 7.24-7.78 (m, 8H).

Step 4 3-[(S)-(4-chlorophenyl)(3-hydroxyazetidin-1-yl)methyl]benzonitrile

To a mixture of 20.27 g (72.6 mmole) of 3-[(S)-[(3-chloro-2-hydroxypropyl)amino](4-chlorophenyl)methyl]benzonitrile hydrochloride and 21.3 g (245 mmole) of $NaHCO_3$ in 600 mL of isopropanol was added 14.4 mL (174 mmole) of epibromohydrin. The mixture was heated to reflux for 24 h, then was cooled and concentrated. The residue was partitioned between 750 mL portions of ether and water and the aqueous layer was washed with two 500 mL portions of ether. The combined organic extracts were washed with brine, dried over $MgSO_4$ and concentrated. The residue was purified by flash chromatography using 10-20% ethyl acetate in hexane to afford the title compound as a clear oil; $^1$H-NMR($CDCl_3$) δ 1.6 (s, 2H, br), 5.24 (s, 1H), 7.24-7.78 (m, 8H).2.89 (m, 2H), 3.54 (m, 2H), 4.39 (s, 1H), 4.52 (m, 1H), 7.2-7.8 (m, 8H).

Step 5: 3-[(S)-(4-chlorophenyl)(3-oxoazetidin-1-yl)methyl]benzonitrile

To a solution of 21.1 mL (0.24 mol) of oxalyl chloride in 500 mL $CH_2Cl_2$, a solution of 34.2 mL (0.48 mol) of DMSO in 50 mL $CH_2Cl_2$ was added slowly at −78° C. After the reaction mixture was stirred for 30 min., a solution of 36.02 g (0.12 mol) of 3-[(S)-(4-chlorophenyl)(3-hydroxyazetidin-1-yl)methyl]benzonitrile in 50 mL of $CH_2Cl_2$ was added and stirred for another 45 min. Then 82.8 mL (0.60 mol) of triethylamine was added and the mixture was stirred for 30 min. at −78° C. The mixture was warmed to rt and stirring continued for 30 min. Then the mixture was poured into 1000 mL of ether and 200 mL of aq $NaHCO_3$. The water layer was extracted with two 200 mL portions of ether. The combined organic layers were dried over $Na_2SO_4$ and concentrated. The residue was purified by silica gel chromatography with hexanes/ethyl acetate to afford the title compound as a white solid; $^1$H-NMR($CDCl_3$) δ 4.03-4.07(m, 4H), 4.65(s, 1H), 7.33-7.43 (m, 4H), 7.45 (t, 1H, J=7.8 Hz), 7.56 (d, 1H, J=7.5 Hz), 7.72 (d, 1H, J=7.5 Hz), 7.81 (s, 1H); Mass Spectrum: m/e=297, (M+1, $^{35}$Cl), 299 (M+1, $^{37}$Cl).

Step 6 Methyl (3-bromo-5-fluorophenyl){1-[(S)-(4-chlorophenyl)(3-cyanophenyl)methyl]azetidin-3-ylidene}acetate To a solution of 14.55 g (58.87 mmol) of methyl (3-bromo-5-fluorophenyl)acetate in 200 mL of THF at −78° C., was added a solution of 56.80 mL (56.80 mmol) (1M in THF) of LHMDS. After the reaction mixture was stirred for 30 min., a solution of 15.60 g (52.57 mmol) of 3-[(S)-(4-chlorophenyl)(3-oxoazetidin-1-yl)methyl]benzonitrile in 50 mL of THF was added and the mixture was stirred for 2.5 h at −78° C. Then 8.35 g (68.33 mmol) of DMAP, 14.65 mL (84.09 mmol) of DEA, and 8.72 mL (110.38 mmol) of methanesulfonyl chloride were added, and the mixture was stirred for 1 h at −78° C. The mixture was then allowed to warm to rt and was stirred at rt for 12 h. The mixture was poured into 300 mL of ether and 100 mL of water. The water layer was extracted with ether (100 mL×2). The combined organic layer was dried over $Na_2SO_4$ and concentrated. The residue was purified by silica gel chromatography with hexanes/ethyl acetate to afford the title compound as a white solid; $^1$H-NMR($CDCl_3$) δ 3.75(s, 3H), 3.87(s, 2H), 4.23-4.29(m, 2H), 4.59(s, 1H), 6.92 (d, 1H, J=12 Hz), 7.18(s, 1H), 7.20 (d, 1H, J=12 Hz), 7.31-7.38 (dd, 4H, J J$_1$=28.4 Hz, J$_2$=8.5 Hz), 7.42 (t, 1H, J=7.7 Hz), 7.54 (d, 1H, J=7.6 Hz), 7.66 (d, 1H, J=7.6 Hz), 7.76 (s, 1H); Mass Spectrum: m/e=525, (M+1, $^{35}$Cl$^{79}$Br), 527 (M+1, $^{37}$Cl$^{79}$Br/$^{35}$Cl$^{81}$Br), 529 (M+1, $^{37}$Cl$^{81}$Br).

Step 7 methyl (2S)-(3-bromo-5-fluorophenyl){1-[(S)-(4-chlorophenyl)(3-cyanophenyl)methyl]azetidin-3-yl}acetate To a solution of 27.15 g (51.64 mmol) of methyl (3-bromo-5-fluorophenyl){1-[(S)-(4-chlorophenyl)(3-cyanophenyl)methyl]azetidin-3-ylidene}acetate in 120 mL of THF and 220 mL of MeOH, were added small portions of sodium borohydride (total: 740 mg, 31.05 mmol) at −5-0° C. The mixture stirred at −5-0° C. and the reaction was followed by HPLC. Then the reaction was quenched with 2N HCl at 0° C. (to pH=7-7.5) and concentrated to remove the organic solvents. The residue was dissolved in 300 mL of CH$_2$Cl$_2$ and 300 mL water, and the layers were separated. The aqueous layer was extracted with CH$_2$Cl$_2$ (100 mL×2). The combined organic layer was dried over Na$_2$SO$_4$ and concentrated. The residue was separated by silica gel chromatography with cyclohexane/ethyl acetate to afford the methyl (2S)-(3-bromo-5-fluorophenyl){1-[(S)-(4-chlorophenyl)(3-cyanophenyl)methyl]azetidin-3-yl}acetate; $^1$H-NMR(CDCl$_3$) δ 2.66(t, 1H, J=6.2 Hz), 2.92(dd, 1H, J$_1$=7.5 Hz, J$_2$=5.7 Hz), 3.08-3.16(m, 2H), 3.41(t, 1H, J=7.2 Hz), 3.69(s, 3H), 3.83(d, 1H, J=10.7 Hz), 4.34(s, 1H), 6.96 (d, 1H, J=8.9 Hz), 7.17(d, 1H, J=8.0 Hz), 7.20 (d, 1H, J=12 Hz), 7.27-7.32 (m, 5H), 7.39 (t, 1H, J=7.6 Hz), 7.50 (d, 1H, J=7.5 Hz), 7.60 (d, 1H, J=7.5 Hz), 7.70 (s, 1H); Mass Spectrum: m/e=527(M+1, $^{35}$Cl$^{79}$Br), 529 (M+1, $^{37}$Cl$^{79}$Br/$^{35}$Cl$^{81}$Br), 531 (M+1, $^{37}$Cl$^{81}$Br).

Further elution of the column afforded methyl (2R)-(3-bromo-5-fluorophenyl){1-[(S)-(4-chlorophenyl)(3-cyanophenyl)methyl]azetidin-3-yl}acetate; $^1$H-NMR(CDCl$_3$) δ 2.67(t, 1H, J=6.2 Hz), 2.90(dd, 1H, J$_1$=7.3 Hz, J$_2$=5.5 Hz), 3.09-3.13(m, 2H), 3.43(t, 1H, J=7.3 Hz), 3.68(s, 3H), 3.82(d, 1H, J=10.7 Hz), 4.34(s, 1H), 6.96 (d, 1H, J=8.9 Hz), 7.17(d, 1H, J=8.1 Hz), 7.20 (d, 1H, J=12 Hz), 7.26-7.32 (m, 5H), 7.40 (t, 1H, J=7.6 Hz), 7.50 (d, 1H, J=7.7 Hz), 7.60 (d, 1H, J=8.0 Hz), 7.70 (s, 1H); Mass Spectrum: m/e=527 (M+1, $^{35}$Cl$^{79}$Br), 529 (M+1, $^{37}$Cl$^{79}$Br/$^{35}$Cl$^{81}$Br), 531 (M+1, $^{37}$Cl $^{81}$Br).

Step 8 3-[(S)-{3-[(1S)-1-(3-bromo-5-fluorophenyl)-2-hydroxy-2-methylpropyl]azetidin-1-yl}(4-chlorophenyl)methyl]benzonitrile A portion of 7.84 g (31.80 mmol) of cerium (III) chloride (anhydrous) was stirred for 30 min under N$_2$ at rt. Then 120 mL of THF (anhydrous) was added, and the slurry was stirred for another 30 min at rt. Then the reaction mixture was cooled to −78° C. and a solution of 14.9 mL (23.80 mmol) methyllithium (1.6M in ether) was added dropwise. After addition was complete, the mixture was stirred for 30 min at −78° C., Then a solution of 6.0 g (11.36 mmol) of methyl (2S)-(3-bromo-5-fluorophenyl){1-[(s)-(4-chlorophenyl)(3-cyanophenyl)methyl]azetidin-3-yl}acetate in 30 mL of THF was added, and the reaction mixture was stirred for 1.5 h at −78° C. The reaction was quenched by dropwise addition of 20 mL water and warmed slowly to rt. The pH was adjusted to 7-8 with aq NaHCO$_3$. The solid residue was washed with CH$_2$Cl$_2$ (300 mL×4). The combined organic layer was dried over Na$_2$SO$_4$ and concentrated. The residue was purified by silica gel chromatography with hexane/ethyl acetate to afford the title compound as a white solid; $^1$H-NMR(CDCl$_3$) δ 1.10 (s, 3H), 1.15 (s, 3H), 2.28(t, 1H, J=7.8 Hz), 2.71(d, 1H, J$_1$=11 Hz), 2.84 (t, 1H, J=7.5 Hz), 3.09-3.18(m, 2H), 3.60 (m, 1H), 4.25(s, 1H), 6.86 (d, 1H, J=9.4 Hz), 7.10-7.13(m, 2H), 7.28-7.34 (m, 4H), 7.36 (t, 1H, J=7.8 Hz), 7.46 (d, 1H, J=7.5 Hz), 7.57 (d, 1H, J=7.5 Hz), 7.67 (s, 1H); Mass Spectrum: m/e=527, (M+1, $^{35}$Cl $^{79}$Br), 529 (M+1, $^{37}$Cl$^{79}$Br/$^{35}$Cl $^{81}$Br), 531 (M+1, $^{37}$Cl $^{81}$Br).

Step 9 3-[(S)-{3-[(1S)-1-(3-bromo-5-fluorophenyl)-2-fluoro-2-methylpropyl]azetidin-1-yl}(4-chlorophenyl)methyl]benzonitrile A mixture of 6.90 g (13.07 mmol) of 3-[(S)-{3-[(1S)-1-(3-bromo-5-fluorophenyl)-2-hydroxy-2-methylpropyl]azetidin-1-yl}(4 chlorophenyl)methyl]benzonitrile, 50 mL of hydrogen fluoride pyridine (HF 70%), and 60 mL of 1,2-dichloroethane was stirred at 40-42° C. for 16 h. Then the reaction mixture was poured slowly to a mixture of 250 mL of water, 74 g of NaOH, 300 mL of aq NaHCO$_3$, 300 g of ice and 500 mL of CH$_2$Cl$_2$ with rapid stirring. The pH of the mixture was adjusted to 7-8, and the mixture was filtered to remove solids. The aqueous layer was extracted with three 300 mL portions of CH$_2$Cl$_2$. The combined organic layer was dried over Na$_2$SO$_4$ and concentrated. The residue was purified by silica gel chromatography with hexane/ethyl acetate to afford the title compound as a white solid; $^1$H-NMR(CDCl$_3$) δ 1.25 (t, 6H, J=11.8 Hz), 2.32(t, 1H, J=7.5 Hz), 2.83-2.89(m, 2H), 3.09-3.17(m, 2H), 3.59 (m, 1H), 4.26(s, 1H), 6.85 (d, 1H, J=9.1 Hz), 7.10-7.14(m, 2H), 7.28-7.33 (m, 4H), 7.36 (t, 1H, J=7.2 Hz), 7.46 (d, 1H, J=7.8 Hz), 7.56 (d, 1H, J=7.7 Hz), 7.67 (s, 1H); Mass Spectrum: m/e=529, (M+1, $^{35}$Cl $^{79}$Br), 531 (M+1, $^{37}$Cl$^{79}$Br/$^{35}$Cl $^{81}$Br), 533 (M+1, $^{37}$Cl$^{81}$Br).

Step 10 3-[(S)-{3-[(1S)-1-(3-bromo-5-fluorophenyl)-2-fluoro-2-methylpropyl]azetidin-1-yl}(4-chlorophenyl)methyl]benzoic acid A mixture of 5.52 g (10.4 mmol) of 3-[(S)-{3-[(1S)-1-(3-bromo-5-fluorophenyl)-2-fluoro-2-methylpropyl]azetidin-1-yl}(4-chlorophenyl)methyl]benzonitrile, 65 mL of EtOH, and 40 mL of 5N NaOH was heated to reflux for 4 h (with monitoring by HPLC). Then the pH solution was adjusted to 4-5 with 12N HCl and the solution was concentrated to remove organic solvents. The residue was dissolved in 200 mL of CH$_2$Cl$_2$ and filtered to remove undissolved solid. The solid residue was triturated with two 200 mL portions of CH$_2$Cl$_2$ and the combined organic layers were concentrated to the title compound as white solid; Mass Spectrum: m/e=548, (M+1, $^{35}$Cl $^{79}$Br), 550 (M+1, $^{37}$Cl$^{79}$Br/$^{35}$Cl $^{81}$Br), 552 (M+1, $^{37}$Cl $^{81}$Br).

Step 11: Ethyl 3-[(S)-{3-[(1S)-1-(3-bromo-5-fluorophenyl)-2-fluoro-2-methylpropyl]azetidin-1-yl}(4-chlorophenyl)methyl]benzoate To a mixture of 5.72 g (10.4 mmol) of 3-[(S)-{3-[(1S)-1-(3-bromo-5-fluorophenyl)-2-fluoro-2-methylpropyl]azetidin-1-yl}(4-chlorophenyl)methyl]benzoic acid in 230 mL of EtOH, was added a solution of 25 mL of 4N HCl in dioxane. After 7.5 h at reflux, the solution was cooled and concentrated to remove solvents. To the residue were added 150 mL of CH$_2$Cl$_2$ and 30 mL of H$_2$O and the pH was adjusted to 7-8 with aq NaHCO$_3$. The aqueous layer was extracted with three 100 mL portions of CH$_2$Cl$_2$ and the combined organic layer was dried over Na$_2$SO$_4$ and concentrated. The residue was purified by silica gel chromatography with hexanes/ethyl acetate to afford the title compound as a white solid; $^1$H-NMR (CDCl$_3$) δ 1.25 (d, 3H, J$_1$=22 Hz), 1.27 (d, 3H, J$_1$=22 Hz), 1.40(t, 3H, J=7.1 Hz), 2.34(t, 1H, J=7.5 Hz), 2.83-2.89(m, 2H), 3.10-3.15(m, 2H), 3.62 (m, 1H), 4.30(s, 1H), 4.38 (q, 2H, $J_1$=14.2 Hz, $J_2$=7.1 Hz), 6.85 (d, 1H, J=9.4 Hz), 7.10-7.11(m, 2H), 7.26-7.38 (m, 5H), 7.55 (d, 1H, J=7.8 Hz), 7.86 (d, 1H, J=7.7 Hz), 8.05 (s, 1H); Mass Spectrum: m/e=576, (M+1, $^{35}$Cl $^{79}$Br), 578 (M+1, $^{37}$Cl$^{79}$Br/$^{35}$Cl $^{81}$Br), 580 (M+1, $^{37}$Cl $^{81}$Br).

Step 12: Ethyl 3-((S)-(4-chlorophenyl){3-[(1S)-1-(3-cyano-5-fluorophenyl)-2-fluoro-2-methyl-propyl]azetidin-1-yl}methyl)benzoate A mixture of 5.64 g (9.77 mmol) of ethyl 3-[(S)-{3-[(1S)-1-(3-bromo-5-fluorophenyl)-2-fluoro-2-methylpropyl]azetidin-1-yl}(4-chlorophenyl)methyl]benzoate, 700 mg (5.96 mmol) of zinc cyanide, 179 mg (0.195 mmol) of tris(dibenzylideneacetone)dipalladium, and 270 mg (0.489 mmol) of DPPF in 99 mL of DMF and 1 mL of water was degassed with $N_2$ for 1 h at rt. Then it was stirred at 125° C. After 12 h, the reaction mixture was concentrated to remove solvents. The residue was poured into 200 mL of $CH_2Cl_2$ and 50 mL of aq $NaHCO_3$ (pH=7-8). The aqueous layer was extracted with $CH_2Cl_2$ and the combined organic layer was dried over $Na_2SO_4$ and concentrated. The residue was purified by silica gel chromatography with hexanes/ethyl acetate to afford the title compound as a white solid; $^1$H-NMR(CDCl$_3$) δ 1.23 (d, 3H, $J_1$=21.7 Hz), 1.28 (d, 3H, $J_1$=21.7 Hz), 1.40(t, 3H, J=7.1 Hz), 2.29(t, 1H, J=7.5 Hz), 2.85-2.95(m, 2H), 3.05(m, 1H), 3.18(m, 1H), 3.64 (t, 1H, J=6.7 Hz), 4.29(s, 1H), 4.37 (q, 2H, $J_1$=14.2 Hz, $J_2$=7.1 Hz), 7.16 (d, 1H, J=9.3 Hz), 7.23 (d, 1H, J=7.8 Hz), 7.27-7.38(m, 6H), 7.55 (d, 1H, J=7.8 Hz), 7.86 (d, 1H, J=7.7 Hz), 8.0 (s, 1H); Mass Spectrum: m/e=523, (M+1, $^{35}$Cl), 525 (M+1, $^{37}$Cl).

Step 13 3-((S)-(4-chlorophenyl){3-[(1S)-1-(3-cyano-5-fluorophenyl)-2-fluoro-2-methylpropyl]azetidin-1-yl}methyl)benzohydrazide A mixture of 3.06 g (5.85 mmol) of ethyl 3-(S)-(4-chlorophenyl){3-[(1S)-1-(3-cyano-5-fluorophenyl)-2-fluoro-2-methylpropyl]azetidin-1-yl}methyl)benzoate, 13 mL (16.36 mmol) of hydrazine, and 85 mL of EtOH was heated to reflux. After 8 h, the solvents were removed to afford the title compound as a white solid.; $^1$H-NMR(CDCl$_3$) δ 1.22 (d, 3H, $J_1$=21.7 Hz), 1.28 (d, 3H, $J_1$=21.7 Hz), 2.29(t, 1H, J=7.5 Hz), 2.85-2.94(m, 2H), 3.07(m, 1H), 3.15(m, 1H), 3.62 (t, 1H, J=6.6 Hz), 4.29(s, 11H), 7.16 (d, 1H, J=9.1 Hz), 7.22 (d, 1H, J=7.5 Hz), 7.25-7.36(m, 6H), 7.50-7.54 (m, 2H), 7.77 (s, 1H); Mass Spectrum: m/e=509, (M+1, $^{35}$Cl), 511 (M+1, $^{37}$Cl).

Step 14 3-[(1S)-1-(1-{(S)-(4-chlorophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile To a solution of 3.0 g (5.85 mmol) of 3-((S)-(4-chlorophenyl){3-[(1S)-1-(3-cyano-5-fluorophenyl)-2-fluoro-2-methylpropyl]azetidin-1-yl}methyl)benzohydrazide in 100 mL of $CH_2Cl_2$ was added 3.73 mL (7.1 mmol) of phosgene solution (20% in toluene). The solution was stirred for 1.5 h at 0° C., The solution was concentrated, and to the residue was added 6 mL of 2N $NH_3$ in MeOH, and the mixture was concentrated again. The residue was purified by silica gel chromatography with $CH_2Cl_2$/acetone to afford the title compound as a white solid; $^1$H-NMR(CDCl$_3$) δ 1.26 (d, 3H, $J_1$=22.1 Hz), 1.30 (d, 3H, $J_1$=21.7 Hz), 2.39(t, 1H, J=8.0 Hz), 2.93-3.0(m, 2H), 3.12(t, 1H, J=7.3 Hz), 3.33(m, 1H), 3.69 (t, 1H, J=6.8 Hz), 4.35(s, 1H), 7.20 (d, 1H, J=9.7 Hz), 7.23 (d, 1H, J=7.3 Hz), 7.29-7.40(m, 7H), 7.48 (d, 1H, J=7.8 Hz), 7.68 (d, 1H, J=7.8 Hz), 7.97 (s, 1H); Mass Spectrum: m/e=535, (M+1, $^{35}$Cl), 537 (M+1, $^{37}$Cl).

EXAMPLES 27 AND 28

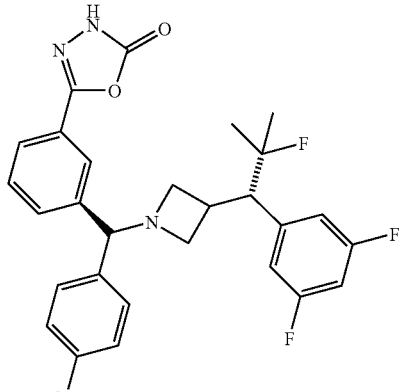

27

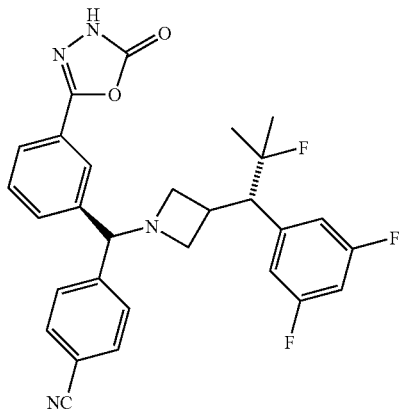

28

The following compounds were prepared according to procedures outlined above, and applying skill of one ordinarily skilled in the art.

Example 27

5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one Mass Spectrum: m/e=528, 530 (M+1).

Example 28

4-{(S)-{3-[(1S)-1-(3,5-difluorophenyl)-2-fluoro-2-methylpropyl]azetidin-1-yl}[3-(5-oxo-4,5-dihydro-1,3,4-oxadiazol-2-yl)phenyl]methyl}-benzonitrile Mass Spectrum: m/e=519 (M+1).

BIOLOGICAL EXAMPLE 1

Cannabinoid Receptor-1 (CB1) Binding Assay

Binding affinity determination is based on recombinant human CB1 receptor expressed in Chinese Hamster Ovary (CHO) cells (Felder et al, Mol. Pharmacol. 48: 443-450, 1995). Total assay volume is 250 μL (240 μL CB1 receptor membrane solution plus 5 μL test compound solution plus 5

µL [3H]CP-55940 solution). Final concentration of [3H]CP-55940 is 0.6 nM. Binding buffer contains 50 mM Tris-HCl, pH7.4, 2.5 mM EDTA, 5 mM $MgCl_2$, 0.5 mg/mL fatty acid free bovine serum albumin and protease inhibitors (Cat#P8340, from Sigma). To initiate the binding reaction, 5 µL of radioligand solution is added, the mixture is incubated with gentle shaking on a shaker for 1.5 hours at 30° C. The binding is terminated by using 96-well harvester and filtering through GF/C filter presoaked in 0.05% polyethylenimine. The bound radiolabel is quantitated using scintillation counter. Apparent binding affinities for various compounds are calculated from $IC_{50}$ values (DeBlasi et al., Trends Pharmacol Sci 10: 227-229, 1989).

The binding assay for CB2 receptor is done similarly with recombinant human CB2 receptor expressed in CHO cells.

CB1 antagonist/inverse agonist compounds of the present invention have $IC_{50}$s of less than 1 micromolar in the CB1 binding assay. Selective CB1 antagonist/inverse agonist compounds have $IC_{50}$s 100-fold greater in the CB2 binding assay than in the CB1 assay, and generally have $IC_{50}$s of greater than one micromolar in the CB2 binding assay.

BIOLOGICAL EXAMPLE 2

Cannabinoid Receptor-1 (CB1) Functional Activity Assay

The functional activation of CB1 receptor is based on recombinant human CB1 receptor expressed in CHO cells (Felder et al, Mol. Pharmacol. 48: 443-450, 1995). To determine the agonist activity or inverse agonist activity of any test compound, 50 µL of CB1-CHO cell suspension are mixed with test compound and 70 uL assay buffer containing 0.34 mM 3-isobutyl-1-methylxanthine and 5.1 µM of forskolin in 96-well plates. The assay buffer is comprised of Earle's Balanced Salt Solution supplemented with 5 mM $MgCl_2$, 1 mM glutamine, 10 mM HEPES, and 1 mg/mL bovine serum albumin. The mixture is incubated at room temperature for 30 minutes, and terminated by adding 30 µl/well of 0.5M HCl. The total intracellular cAMP level is quantitated using the New England Nuclear Flashplate and cAMP radioimmunoassay kit.

To determine the antagonist activity of test compound, the reaction mixture also contains 0.5 nM of the agonist CP55940, and the reversal of the CP55940 effect is quantitated. Alternatively, a series of dose response curves for CP55940 is performed with increasing concentration of the test compound in each of the dose response curves.

The functional assay for the CB2 receptor is done similarly with recombinant human CB2 receptor expressed in CHO cells.

CB1 antagonist/inverse agonist compounds of the present invention generally have EC50s of less than 1 micromolar in the CB1 functional assay and selective CB1 antagonist/inverse agonists have generally have $EC_{50}$s of greater than 1 micromolar in the CB2 functional assay.

BIOLOGICAL EXAMPLE 3

Acute Food Intake Studies in Rats or Mice: General Procedure

Adult rats or mice are used in these studies. After at least 2 days of acclimation to the vivarium conditions (controlled humidity and temperature, lights on for 12 hours out of 24 hours) food is removed from rodent cages. Experimental compounds or their vehicles are administered orally, intraperitoneally, subcutaneously or intravenously before the return of a known amount of food to cage. The optimal interval between dosing and food presentation is based on the half-life of the compound based on when brain concentrations of the compound is the highest. Food remaining is measured at several intervals. Food intake is calculated as grams of food eaten per gram of body weight within each time interval and the appetite-suppressant effect of the compounds are compared to the effect of vehicle. In these experiments many strains of mouse or rat, and several standard rodent chows can be used.

BIOLOGICAL EXAMPLE 4

Chronic Weight Reduction Studies in Rats or Mice: General Procedure

Adult rats or mice are used in these studies. Upon or soon after weaning, rats or mice are made obese due to exclusive access to diets containing fat and sucrose in higher proportions than in the control diet. The rat strains commonly used include the Sprague Dawley bred through Charles River Laboratories. Although several mouse strains may be used, c57B1/6 mice are more prone to obesity and hyperinsulinemia than other strains. Common diets used to induce obesity include: Research Diets D12266B (32% fat) or D12451 (45% fat) and BioServ S3282 (60% fat). The rodents ingest chow until they are significantly heavier and have a higher proportion of body fat than control diet rats, often 9 weeks. The rodents receive injections (1 to 4 per day) or continuous infusions of experimental compounds or their vehicles either orally, intraperitoneally, subcutaneously or intravenously. Food intake and body weights are measured daily or more frequently. Food intake is calculated as grams of food eaten per gram of body weight within each time interval and the appetite-suppressant and weight loss effects of the compounds are compared to the effects of vehicle.

BIOLOGICAL EXAMPLE 5

Tail Suspension Test

The tail suspension test has been widely used for screening antidepressant-like effects of compounds in mice (Steru et al., 1987), rats (Izumi et al, 1997) and gerbils (Varty et al., 2003). It is based on the principle that helplessness takes place when the animal is exposed to a sustained aversive situation. Briefly, when the animal is suspended by its tail it exhibits several escape-oriented behaviors intercalated with bouts of immobility that evolve with time into complete immobility. Pretreatment with a wide range of antidepressants, such as tricyclic compounds, monoamine uptake blockers, or serotonin reuptake inhibitors (SSRIs), significantly decrease duration of immobility throughout the test, while anxiolytics or antipsychotics do not (Wong et al., 2000; Oxenkrug 1999).

Subjects

Male mice are housed in a colony room maintained at constant temperature (22° C.) and humidity (30-70%), with food (Harlan Teklad Diet #7012, 5% fat; 3.75 kcal/gm) and water available ad libitum. For the behavioral experiments, mice are group housed (10/cage) under a reversed light/dark cycle (lights on at 21:00 h, off at 09:00 h) and tests occurred between 10:00 h and 14:00 h.

Drugs

The compounds of formula (I) are solubilized into 1% Tween80-saline solution, addition of DMSO may be employed to increase solubility. Compounds are dosed intraperitonieally in a volume of 0.1 mL.

Tail Suspension Test

An automated tail-suspension apparatus (TSE Systems, Bad Homburg, Germany) with a tail hanger connected to a precision linear load cell is used. One centimeter of the mouse's tail is inserted into the tail hanger and secured with non-irritating adhesive tape. Mice are suspended by the tail, at a height of 35 cm from the tabletop for 6 minutes. During this time the load cell records the mouse's movements and transmits the information to a central computer, which then records the rate of immobility within the course of the session, and calculates total duration of immobility.

Total duration of immobility is used as the dependent variable in one-way Analysis of Variance (ANOVA) on treatment.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of structural formula I:

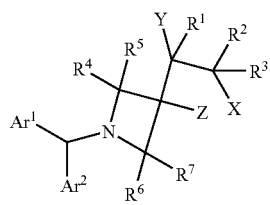

(I)

wherein:

Ar$^1$ is:

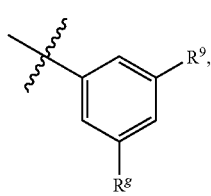

wherein R$^g$ is hydrogen, and R$^9$ is selected from R$^{15}$, hydrogen, and cyano;

Ar$^2$ is:

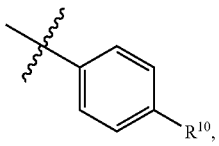

wherein R$^{10}$ is selected from: R$^{15}$, hydrogen, halogen, and cyano;

X is selected from:
(1) hydroxy,
(2) NH$_2$,
(3) methyl, and
(4) methoxy;

R$^4$, R$^5$, R$^6$, R$^7$, Y, and Z are each hydrogen;

R$^1$ is:

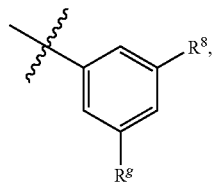

wherein R$^8$ is selected from R$^{15}$, fluoro, and cyano, and R$^g$ is halogen;

R$^2$ is selected from:
(1) hydrogen,
(2) fluoro,
(3) methyl, and
(4) hydroxyl;

R$^3$ is selected from methyl, and hydroxyl;

R$^8$ is selected from:
(1) R$^{15}$,
(2) hydrogen,
(3) halogen,
(4) methyl,
(5) —CF$_3$,
(6) cyano, and
(7) SO$_2$CH$_3$;

provided that at least one of R$^8$, R$^9$, and R$^{10}$ is R$^{15}$;

each R$^{15}$ is independently selected from:

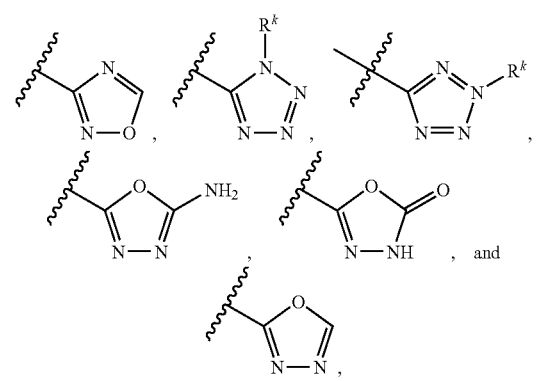

wherein R$^k$ is selected from hydrogen and methyl;

or a pharmaceutically acceptable salt thereof.

2. The compound according to claim 1, of structural formula IF:

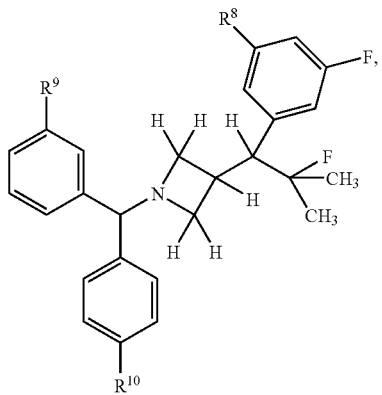

wherein only one of $R^8$, $R^9$, and $R^{10}$ is $R^{15}$, or a pharmaceutically acceptable salt thereof.

3. The compound according to claim 1, selected from:

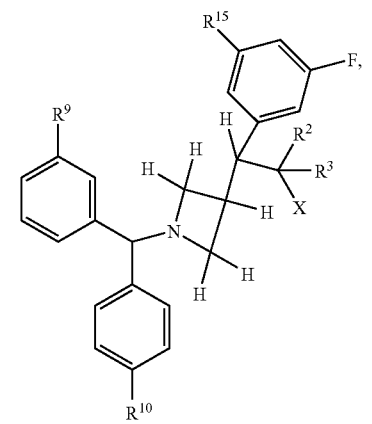

(a)

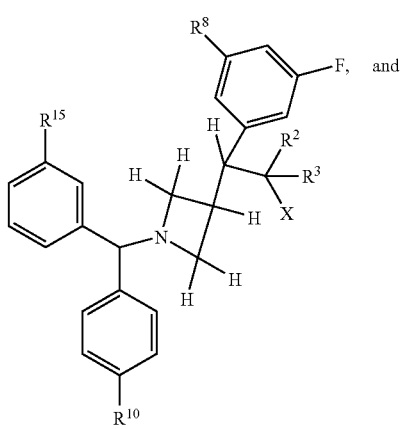

(b) and

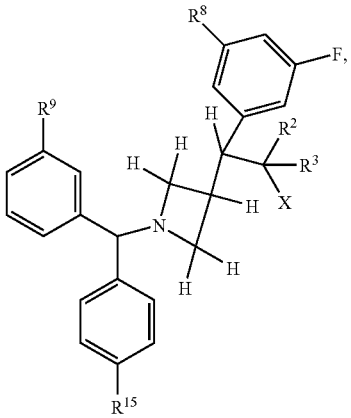

(c)

or a pharmaceutically acceptable salt thereof.

4. A compound according to claim 1, selected from:
  (1) 3-[(S)-(4-chlorophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile,
  (2) 3-[(S)-(4-chlorophenyl)(3-{(1S)-2-fluoro-1-[3-fluoro-5-(1,3,4-oxadiazol-2-yl)phenyl]-2-methylpropyl}azetidin-1-yl)methyl]benzonitrile,
  (3) 3-[(S)-(3-{(1S)-1-[3-(5-amino-1,3,4-oxadiazol-2-yl)-5-fluorophenyl]-2-fluoro-2-methylpropyl}azetidin-1-yl)(4-chlorophenyl)methyl]benzonitrile,
  (4) 3-[(S)-(4-cyanophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile,
  (5) 3-[(S)-(3-{(1S)-1-[3-(5-amino-1,3,4-oxadiazol-2-yl)-5-fluorophenyl]-2-fluoro-2-methylpropyl}azetidin-1-yl)(4-cyanophenyl)methyl]benzonitrile,
  (6) 3-[(S)-(4-cyanophenyl)(3-{(1S)-2-fluoro-1-[3-fluoro-5-(1,3,4-oxadiazol-2-yl)phenyl]-2-methylpropyl}azetidin-1-yl)methyl]benzonitrile,
  (7) 3-[(S)-(4-chlorophenyl)(3-{(1S)-2-fluoro-1-[3-fluoro-5-(1,2,4-oxadiazol-3-yl)phenyl]-2-methylpropyl}azetidin-1-yl)methyl]benzonitrile,
  (8) 3-[(1S)-1-(1-{(S)-(4-cyanophenyl)[3-(1,2,4-oxadiazol-3-yl)phenyl]-methyl}azetidin-3-yl)-2-fluoro-2-methylpropyl]-5-fluorobenzonitrile,
  (9) 5-(3-{1-[1-(diphenylmethyl)azetidin-3-yl]-2-fluoro-2-methylpropyl}-5-fluorophenyl)-1H-tetrazole,
  (10) 5-(3-{1-[1-(diphenylmethyl)azetidin-3-yl]-2-fluoro-2-methylpropyl}-5-fluorophenyl)-1-methyl-1H-tetrazole,
  (11) 5-(3-{1-[1-(diphenylmethyl)azetidin-3-yl]-2-fluoro-2-methylpropyl}-5-fluorophenyl)-2-methyl-2H-tetrazole,
  (12) 3-[(4-chlorophenyl)(3-{2-fluoro-1-[3-fluoro-5-(2-methyl-2H-tetrazol-5-yl)phenyl]-2-methylpropyl}azetidin-1-yl)methyl]benzonitrile,
  (13) 3-[(4-chlorophenyl)(3-{2-fluoro-1-[3-fluoro-5-(1-methyl-1H-tetrazol-5-yl)phenyl]-2-methylpropyl}azetidin-1-yl)methyl]benzonitrile,
  (14) 3-[(4-cyanophenyl)(3-{2-fluoro-1-[3-fluoro-5-(1-methyl-1H-tetrazol-5-yl)phenyl]-2-methylpropyl}azetidin-1-yl)methyl]benzonitrile,
  (15) 3-[(4-cyanophenyl)(3-{2-fluoro-1-[3-fluoro-5-(2-methyl-2H-tetrazol-5-yl)phenyl]-2-methylpropyl}azetidin-1-yl)methyl]benzonitrile,

(16) 5-{3-[(S)-{3-[(1S)-1-(3-bromo-5-fluorophenyl)-2-fluoro-2-methylpropyl]azetidin-1-yl}(4-chlorophenyl)methyl]phenyl}-1,3,4-oxadiazol-2(3H)-one,

(17) 3-[(1S)-1-(1-{(S)-(4-chlorophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile,

(18) 3-[(1S)-1-(1-{(S)-(4-cyanophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile,

(19) 3-[(1S)-1-(1-{(S)-(4-cyanophenyl)[3-(1,3,4-oxadiazol-2-yl)phenyl]methyl}azetidin-3-yl)-2-fluoro-2-methylpropyl]-5-fluorobenzonitrile,

(20) 3-[(1S)-1-(1-{(S)-(4-chlorophenyl)[3-(1,3,4-oxadiazol-2-yl)phenyl]methyl}azetidin-3-yl)-2-fluoro-2-methylpropyl]-5-fluorobenzonitrile,

(21) 3-((1S)-1-{1-[(S)-[3-(5-amino-1,3,4-oxadiazol-2-yl)phenyl](4-chlorophenyl)methyl]azetidin-3-yl}-2-fluoro-2-methylpropyl)-5-fluorobenzonitrile,

(22) 3-((1S)-1-{1-[(S)-[3-(5-amino-1,3,4-oxadiazol-2-yl)phenyl](4-cyanophenyl)methyl]azetidin-3-yl}-2-fluoro-2-methylpropyl)-5-fluorobenzonitrile,

(23) 3-[(1S)-1-(1-{(S)-(4-cyanophenyl)[3-(1,2,4-oxadiazol-3-yl)phenyl]methyl}azetidin-3-yl)-2-fluoro-2-methylpropyl]-5-fluorobenzonitrile,

(24) 3-[(1S)-1-(1-{(S)-(4-chlorophenyl)[3-(1,2,4-oxadiazol-3-yl)phenyl]methyl}azetidin-3-yl)-2-fluoro-2-methylpropyl]-5-fluorobenzonitrile,

(25) 5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one,

(26) 5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one,

(27) 4-{(S)-{3-[(1S)-1-(3,5-difluorophenyl)-2-fluoro-2-methylpropyl]azetidin-1-yl}[3-(5-oxo-4,5-dihydro-1,3,4-oxadiazol-2-yl)phenyl]methyl}-benzonitrile, or a pharmaceutically acceptable salt thereof.

5. A composition comprising a compound according to claim 1 and a pharmaceutically acceptable carrier.

6. A composition comprising a compound according to claim 1, or a pharmaceutically acceptable salt thereof, and a compound selected from simvastatin, ezetimibe, and 7-[(3R)-3-amino-4-(2,4,5-trifluorophenyl)butanoyl)-3-(trifluoromethyl)-5,6,7,8-tetrahydro-1,2,4-triazolo[4,3-a]pyrazine, or a pharmaceutically acceptable salt thereof, and a pharmaceutically acceptable carrier.

7. The compound according to Claim 1, wherein $R^8$ is selected from:
(1) fluoro, and
(2) cyano;
or a pharmaceutically acceptable salt thereof.

8. The compound according to claim 1, wherein
X is methyl;
$R^2$ is fluoro and $R^3$ is methyl;
$R^{15}$ is selected from:

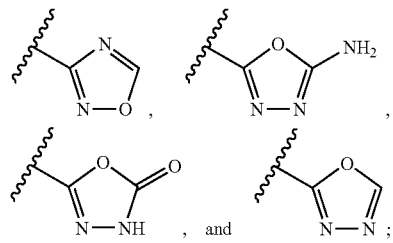

or a pharmaceutically acceptable salt thereof.

9. The compound according to claim 1 which is: 3-[(1S)-1-(1-{(S)-(4-chlorophenyl)[3-(5-oxo-4,5-dihydro-1,3,4-oxadiazol-2-yl)phenyl]methyl}-azetidin-3-yl)-2-fluoro-2-methylpropyl]-5-fluorobenzonitrile; or a pharmaceutically acceptable salt thereof.

* * * * *